United States Patent
Brown et al.

(10) Patent No.: US 12,419,954 B2
(45) Date of Patent: Sep. 23, 2025

(54) TARGETED CHIMERIC ANTIGEN RECEPTOR MODIFIED T CELLS FOR TREATMENT OF IL13Rα2 POSITIVE MALIGNANCIES

(71) Applicants: City of Hope, Duarte, CA (US); The Board of Trustees of the Leland Stanford Junior University, Stanford, CA (US)

(72) Inventors: Christine E. Brown, Duarte, CA (US); Lawrence Stern, Duarte, CA (US); Xin Yang, Duarte, CA (US); K. Christopher Garcia, Duarte, CA (US); Ignacio Moraga Gonzalez, Duarte, CA (US)

(73) Assignees: City of Hope, Duarte, CA (US); The Board of Trustees of the Leland Stanford Junior University, Stanford, CA (US)

( * ) Notice: Subject to any disclaimer, the term of this patent is extended or adjusted under 35 U.S.C. 154(b) by 429 days.

(21) Appl. No.: 17/796,349

(22) PCT Filed: Jan. 19, 2021

(86) PCT No.: PCT/US2021/014008
§ 371 (c)(1),
(2) Date: Jul. 29, 2022

(87) PCT Pub. No.: WO2021/154543
PCT Pub. Date: Aug. 5, 2021

(65) Prior Publication Data
US 2023/0372483 A1 Nov. 23, 2023

Related U.S. Application Data

(60) Provisional application No. 62/968,975, filed on Jan. 31, 2020.

(51) Int. Cl.
| | | |
|---|---|---|
| *A61K 40/31* | (2025.01) | |
| *A61K 40/11* | (2025.01) | |
| *A61K 40/42* | (2025.01) | |
| *A61P 35/00* | (2006.01) | |
| *C12N 15/86* | (2006.01) | |

(52) U.S. Cl.
CPC .............. *A61K 40/31* (2025.01); *A61K 40/11* (2025.01); *A61K 40/4217* (2025.01); *A61P 35/00* (2018.01); *C12N 15/86* (2013.01); *A61K 2239/31* (2023.05); *A61K 2239/38* (2023.05); *A61K 2239/47* (2023.05)

(58) Field of Classification Search
CPC ................................. A61K 40/31; C12N 15/86
See application file for complete search history.

(56) References Cited

U.S. PATENT DOCUMENTS

2012/0148552 A1 6/2012 Jensen
2017/0224733 A1 8/2017 Badie et al.

FOREIGN PATENT DOCUMENTS

| JP | 2017-534262 A | 11/2017 |
| JP | 2019-504105 A | 2/2019 |
| WO | WO 2019/239213 | 12/2012 |
| WO | WO 2017/015490 | 1/2017 |
| WO | WO 2018/112266 A1 | 6/2018 |

OTHER PUBLICATIONS

Beard et al., "Gene expression profiling using Nanostring digital RNA counting to identify potential target antigens for melanoma immunotherapy," Clinical Cancer Research, Sep. 2013, 19(18):4941-4950.
Boder et al., "Yeast surface display for screening combinatorial polypeptide libraries," Nature biotechnology, Jun. 1997, 15(6):553-557.
Boyiadzis et al., Chimeric antigen receptor (CAR) T therapies for the treatment of hematologic malignancies: clinical perspective and significance. Journal for immunotherapy of cancer, Dec. 2018, 6(1): 27 pages.
Brombacher et al., "IL-13-Mediated Regulation of Learning and Memory." J Immunol, 2017, 198(7): 2681-2688. (10 pages).
Brown et al., "Bioactivity and Safety of IL13Ralpha2-Redirected Chimeric Antigen Receptor CD8+ T Cells in Patients with Recurrent Glioblastoma." Clin Cancer Res, 2015, 21(18): 4062-4072.
Brown et al., "Glioma IL13Ralpha2 is associated with mesenchymal signature gene expression and poor patient prognosis." PLoS One, 2013, 8(10): e77769 (14 pages).
Brown et al., "Regression of Glioblastoma after Chimeric Antigen Receptor T-Cell Therapy." N Engl J Med, Dec. 29, 2016, 375(26): 2561-2569.
Brown et al., "Stem-like tumor-initiating cells isolated from IL13Ralpha2 expressing gliomas are targeted and killed by IL13-zetakine-redirected T Cells." Clin Cancer Res, 2012, 18(8): 2199-2209.
Chiu et al., "Engineering antibody therapeutics." Curr Opin Struct Biol, 2016, 38:163-173.
Debinski et al., "Molecular Expression Analysis of Restrictive Receptor for Interleukin 13, a Brain Tumor-associated Cancer/Testis Antigen." Molecular Medicine, 2000, 6(5): 440-449.
Donnelly et al., "Analysis of the aphthovirus 2A/2B polyprotein 'cleavage' mechanism indicates not a proteolytic reaction, but a novel translational effect: a putative ribosomal 'skip'." J Gen Virol, 2001, 82(Pt 5): 1013-1025.
Grupp et al., "Chimeric antigen receptor-modified T cells for acute lymphoid leukemia." N Engl J Med, 2013, 368(16): 1509-1518.

(Continued)

*Primary Examiner* — Prema M Mertz
(74) *Attorney, Agent, or Firm* — Fish & Richardson P.C.

(57) ABSTRACT

Chimeric antigen receptor molecules that include a variant IL-13. The variant IL-13 are more selective for IL13Rα2 than IL13Rα1 by virtue of weaker binding to IL13Rα1. The chimeric antigen receptors can be used to treat IL13Rα2 expressing cancers.

20 Claims, 24 Drawing Sheets

Specification includes a Sequence Listing.

(56) References Cited

OTHER PUBLICATIONS

Hecker et al., "Dysregulation of the IL-13 receptor system: a novel pathomechanism in pulmonary arterial hypertension." Am J Respir Crit Care Med, 2010, 182(6): 805-818.
Hinck et al., "Structure-guided engineering of TGF-βs for the development of novel inhibitors and probing mechanism." Bioorg Med Chem, 2018, 26(19): 5239-5246.
Jonnalagadda et al., "Chimeric antigen receptors with mutated IgG4 Fc spacer avoid Fc receptor binding and improve T cell persistence and antitumor efficacy," Mol Ther, 2015, 23(4): 757-768.
Kahlon et al., "Specific recognition and killing of glioblastoma multiforme by interleukin 13-zetakine redirected cytolytic T cells." Cancer Res, 2004, 64(24): 9160-9166. (8 pages).
Kioi et al., "Interleukin-13 receptor α2 chain: a potential biomarker and molecular target for ovarian cancer therapy." Cancer, 2006, 107(6): 1407-1418.
Kong et al., "Suppression of human glioma xenografts with second-generation IL13R-specific chimeric antigen receptor-modified T cells." Clin Cancer Res, 2012, 18(21): 5949-5960.
Krebs et al., "T cells redirected to interleukin-13Rα2 with interleukin-13 mutein-chimeric antigen receptors have anti-glioma activity but also recognize interleukin-13Rα1." Cytotherapy, 2014, 16(8): 1121-1131.
LaPorte et al., "Molecular and structural basis of cytokine receptor pleiotropy in the interleukin-4/13 system." Cell, 2008, 132(2): 259-272.
Lee et al., "An APRIL-based chimeric antigen receptor for dual targeting of BCMA and TACI in multiple myeloma." Blood, 2018, 131(7): 746-758.
Long et al., "CAR T Cell Therapy of Non-hematopoietic Malignancies: Detours on the Road to Clinical Success." Frontiers in Immunology 2018, 9(2740):1-13.
Lupardus et al., "Molecular Basis for Shared Cytokine Recognition Revealed in the Structure of an Unusually High Affinity Complex between IL-13 and IL-13Rα2." Structure, 2010, 18(3): 332-342.
Maude et al., "Chimeric antigen receptor T cells for sustained remissions in leukemia." N Engl J Med, 2014, 371(16): 1507-1517.
Moraga et al., "Instructive roles for cytokine-receptor binding parameters in determining signaling and functional potency." Science Signaling, 2015, 8(402): ra114, 18 pages.
Murata et al., "Interleukin-13 Receptor α' but Not α Chain: A Functional Component of Interleukin-4 Receptors." Blood, 1998, 91(10): 3884-3891.
Papageorgis et al., "Targeting IL13Ralpha2 activates STAT6-TP63 pathway to suppress breast cancer lung metastasis." Breast Cancer Res, 2015, 17: 98 (15 pages).
PCT International Search Report and Written Opinion in International Appln. No. PCT/US2021/014008, mailed on Jul. 23, 2021, 19 pages.
PCT Invitation to Pay Fees in International Appln. No. PCT/US2021/014008, mailed on Jun. 2, 2021, 12 pages.
Porter et al., "Chimeric Antigen Receptor-Modified T Cells in Chronic Lymphoid Leukemia." The New England Journal of Medicine, 2011, 365(8): 725-733.
Shaffer et al., "Foreign or Domestic CARs: Receptor Ligands as Antigen-Binding Domains." Medical Sciences, 2014, 2: 23-36.
Shaffer et al., "T cells redirected against CD70 for the immunotherapy of CD70-positive malignancies." Blood, 2011, 117(16): 4304-4314.
Shibasaki et al., "Role of IL13RA2 in Sunitinib Resistance in Clear Cell Renal Cell Carcinoma." PLoS One, 2015, 10(6): e0130980 (20 pages).
Shimamura et al., "Interleukin 13 mediates signal transduction through interleukin 13 receptor alpha2 in pancreatic ductal adenocarcinoma: role of IL-13 Pseudomonas exotoxin in pancreatic cancer therapy." Clin Cancer Res, 2010, 16(2): 577-586.
Sockolosky et al., "Selective targeting of engineered T cells using orthogonal IL-2 cytokine-receptor complexes." Science, 2018, 359(6379): 1037-1042.
Thaci et al., "Significance of interleukin-13 receptor alpha 2-targeted glioblastoma therapy." NeuroOncology, 2014, 16(10): 1304-1312.
Wang et al., "Phenotypic and functional attributes of lentivirus-modified CD19-specific human CD8+ central memory T cells manufactured at clinical scale." J Immunother, 2012, 35(9): 689-701.
Xie et al., "IL-13 receptor α2 is a negative prognostic factor in human lung cancer and stimulates lung cancer growth in mice." Oncotarget, 2015, 6(32): 32902-32913.
Zhang et al., "Chimeric NK-receptor-bearing T cells mediate antitumor immunotherapy." Blood, 2005, 106(5): 1544-1551.

| | IL13Rα1 Ka (1/Ms) | IL13Rα1 Kd (1/s) | IL13Rα1 KD (nM) | IL13Rα1 KDwt/KD mut | IL13Rα2 Ka (1/Ms) | IL13Rα2 Kd (1/s) | IL13Rα2 KD (nM) | IL13Rα2 KDwt/KD mut | IL13Rα1/IL13Rα2 |
|---|---|---|---|---|---|---|---|---|---|
| IL-13 | $5.21 \times 10^6$ | 0.022 | 4.38 | 1 | $5 \times 10^7$ | $8.4 \times 10^{-5}$ | 0.001 | 1 | 440 |
| C4 | | | 36,000 | 8,200 | $1.94 \times 10^6$ | $7.64 \times 10^{-4}$ | 0.393 | 393 | 92,000 |
| D7 | | | 4,100 | 940 | $1.77 \times 10^7$ | $5.37 \times 10^{-5}$ | 0.003 | 3 | 1,400,000 |

FIG 1C

MLLLVTSLLLCELPHPAFLLIPGPVPPSTAVRELIEELVNITQNQKAPLCNGSMVWSINLTAGMYCAALESLINVSG

Signal Sequence        IL13(C4)

CSAIEKTQRMLSGFCPHKVSAGQFSSLHVRDTRIEVAQFVKDLLNHLKELFTEGQFNESKYGPPCPPCPAPEFEGGP

IgG4(L235E,N297Q)

SVFLFPPKPKDTLMISRTPEVTCVVVDVSQEDPEVQFNWYVDGVEVHNAKTKPREEQFQSTYRVVSVLTVLHQDWLN

GKEYKCKVSNKGLPSSIEKTISKAKGQPREPQVYTLPPSQEEMTKNQVSLTCLVKGFYPSDIAVEWESNGQPENNYK

TTPPVLDSDGSFFLYSRLTVDKSRWQEGNVFSCSVMHEALHNHYTQKSLSLSLGKMFWVLVVVGGVLACYSLLVTVA

CD28 TM(M)

FIIFWVRSKRSRGGHSDYMNMTPRRPGPTRKHYQPYAPPRDFAAYRSGGGRVKFSRSADAPAYQQGQNQLYNELNLG

CD28 (GG)                                         CD3 zeta

RREEYDVLDKRRGRDPEMGGKPRRKNPQEGLYNELQKDKMAEAYSEIGMKGERRRGKGHDGLYQGLSTATKDTYDAL

HMQALPPRLEGGGEGRGSLLTCGDVEENPGPRMPPPRLLFFLLFLTPMEVRPEEPLVVKVEEGDNAVLQCLKGTSDG

T2A-CD19t

PTQQLTWSRESPLKPFLKLSLGLPGLGIHMRPLAIWLFIFNVSQQMGGFYLCQPGPPSEKAWQPGWTVNVEGSGELF
RWNVSDLGGLGCGLKNRSSEGPSSPSGKLMSPKLYVWAKDRPEIWEGEPPCVPPRDSLNQSLSQDLTMAPGSTLWLS
CGVPPDSVSRGPLSWTHVHPKGPKSLLSLELKDDRPARDMWVMETGLLLPRATAQDAGKYYCHRGNLTMSFHLEITA
RPVLWHWLLRTGGWKVSAVTLAYLIFCLCSLVGILHLQRALVLRRKR

FIG. 10A

PGPVPPSTAVRELIEELVNITQNQKAPLCNGSMVWSINLTAGMYCAALESLINVSG

IL13(C4)

CSAIEKTQRMLSGFCPHKVSAGQFSSLHVRDTRIEVAQFVKDLLNHLKELFTEGQFNESKYGPPCPPCPAPEFEGGP

IgG4(L235E,N297Q)

SVFLFPPKPKDTLMISRTPEVTCVVVDVSQEDPEVQFNWYVDGVEVHNAKTKPREEQFQSTYRVVSVLTVLHQDWLN

GKEYKCKVSNKGLPSSIEKTISKAKGQPREPQVYTLPPSQEEMTKNQVSLTCLVKGFYPSDIAVEWESNGQPENNYK

TTPPVLDSDGSFFLYSRLTVDKSRWQEGNVFSCSVMHEALHNHYTQKSLSLSLGKMFWVLVVVGGVLACYSLLVTVA

CD28 TM(M)

FIIFWVRSKRSRGGHSDYMNMTPRRPGPTRKHYQPYAPPRDFAAYRSGGGRVKFSRSADAPAYQQGQNQLYNELNLG

CD28 (GG)                                         CD3 zeta

RREEYDVLDKRRGRDPEMGGKPRRKNPQEGLYNELQKDKMAEAYSEIGMKGERRRGKGHDGLYQGLSTATKDTYDAL

HMQALPPR

FIG. 10B

MLLLVTSLLLCELPHPAFLLI PGPVPPSTAVRELIEELVNITQNQKAPLCNGSMVWSINLTAGMYCAALESLINVSG

Signal Sequence    IL13(C4)

CSAIEKTQRMLSGFCPHKVSAGQFSSLHVRDTRIEVAQFVKDLLNHLKELFTEGQFNESKYGPPCPPCPGGGSSGGG

IgG4(HL-CH3)

SGGQPREPQVYTLPPSQEEMTKNQVSLTCLVKGFYPSDIAVEWESNGQPENNYKTTPPVLDSDGSFFLYSRLTVDKS

RWQEGNVFSCSVMHEALHNHYTQKSLSLSLGKMALIVLGGVAGLLLFIGLGIFFKRGRKKLLYIFKQPFMRPVQTTQ

CD4 TM                  41-BB

EEDGCSCRFPEEEEGGCELGGGRVKFSRSADAPAYQQGQNQLYNELNLGRREEYDVLDKRRGRDPEMGGKPRRKNPQ

CD3 ZETA

EGLYNELQKDKMAEAYSEIGMKGERRRGKGHDGLYQGLSTATKDTYDALHMQALPPRLEGGGEGRGSLLTCGDVEEN

T2A-CD19t (BspEI)

PGPRMPPPRLLFFLLFLTPMEVRPEEPLVVKVEEGDNAVLQCLKGTSDGPTQQLTWSRESPLKPFLKLSLGLPGLGI
HMRPLAIWLFIFNVSQQMGGFYLCQPGPPSEKAWQPGWTVNVEGSGELFRWNVSDLGGLGCGLKNRSSEGPSSPSGK
LMSPKLYVWAKDRPEIWEGEPPCVPPRDSLNQSLSQDLTMAPGSTLWLSCGVPPDSVSRGPLSWTHVHPKGPKSLLS
LELKDDRPARDMWVMETGLLLPRATAQDAGKYYCHRGNLTMSFHLEITARPVLHWLLRTGGWKVSAVTLAYLIFCL
CSLVGILHLQRALVLRRKR

FIG. 11A

PGPVPPSTAVRELIEELVNITQNQKAPLCNGSMVWSINLTAGMYCAALESLINVSG

IL13(C4)

CSAIEKTQRMLSGFCPHKVSAGQFSSLHVRDTRIEVAQFVKDLLNHLKELFTEGQFNESKYGPPCPPCPGGGSSGGG

IgG4(HL-CH3)

SGGQPREPQVYTLPPSQEEMTKNQVSLTCLVKGFYPSDIAVEWESNGQPENNYKTTPPVLDSDGSFFLYSRLTVDKS

RWQEGNVFSCSVMHEALHNHYTQKSLSLSLGKMALIVLGGVAGLLLFIGLGIFFKRGRKKLLYIFKQPFMRPVQTTQ

CD4 TM                  41-BB

EEDGCSCRFPEEEEGGCELGGGRVKFSRSADAPAYQQGQNQLYNELNLGRREEYDVLDKRRGRDPEMGGKPRRKNPQ

CD3 ZETA

EGLYNELQKDKMAEAYSEIGMKGERRRGKGHDGLYQGLSTATKDTYDALHMQALPPR

FIG. 11B

MLLLVTSLLLCELPHPAFLLIPGPVPPSTAARELIEELFNITQNQKAPLCNGSMVWSINLTAGMYCAALESLINVSG
Signal Sequence        IL13(D7)

CSAIEKTKRMLSGFCPHKVSAGQFPSLHVKKTRIEVAQFVKDLLIHLRKLFKEGQFNESKYGPPCPPCPAPEFEGGP
                                                         IgG4(L235E,N297Q)

SVFLFPPKPKDTLMISRTPEVTCVVVDVSQEDPEVQFNWYVDGVEVHNAKTKPREEQFQSTYRVVSVLTVLHQDWLN

GKEYKCKVSNKGLPSSIEKTISKAKGQPREPQVYTLPPSQEEMTKNQVSLTCLVKGFYPSDIAVEWESNGQPENNYK

TTPPVLDSDGSFFLYSRLTVDKSRWQEGNVFSCSVMHEALHNHYTQKSLSLSLGKMFWVLVVVGGVLACYSLLVTVA
                                                                 CD28 TM(M)

FIIFWVRSKRSRGGHSDYMNMTPRRPGPTRKHYQPYAPPRDFAAYRSGGGRVKFSRSADAPAYQQGQNQLYNELNLG
     CD28 (GG)                                  CD3 zeta

RREEYDVLDKRRGRDPEMGGKPRRKNPQEGLYNELQKDKMAEAYSEIGMKGERRRGKGHDGLYQGLSTATKDTYDAL

HMQALPPRLEGGGEGRGSLLTCGDVEENPGPRMPPPRLLFFLLFLTPMEVRPEEPLVVKVEEGDNAVLQCLKGTSDG
         T2A-CD19t

PTQQLTWSRESPLKPFLKLSLGLPGLGIHMRPLAIWLFIFNVSQQMGGFYLCQPGPPSEKAWQPGWTVNVEGSGELF
RWNVSDLGGLGCGLKNRSSEGPSSPSGKLMSPKLYVWAKDRPEIWEGEPPCVPPRDSLNQSLSQDLTMAPGSTLWLS
CGVPPDSVSRGPLSWTHVHPKGPKSLLSLELKDDRPARDMWVMETGLLLPRATAQDAGKYYCHRGNLTMSFHLEITA
RPVLHWLLRTGGWKVSAVTLAYLIFCLCSLVGILHLQRALVLRRKR

FIG. 12A

PGPVPPSTAARELIEELFNITQNQKAPLCNGSMVWSINLTAGMYCAALESLINVSG
                         IL13(D7)

CSAIEKTKRMLSGFCPHKVSAGQFPSLHVKKTRIEVAQFVKDLLIHLRKLFKEGQFNESKYGPPCPPCPAPEFEGGP
                                                         IgG4(L235E,N297Q)

SVFLFPPKPKDTLMISRTPEVTCVVVDVSQEDPEVQFNWYVDGVEVHNAKTKPREEQFQSTYRVVSVLTVLHQDWLN

GKEYKCKVSNKGLPSSIEKTISKAKGQPREPQVYTLPPSQEEMTKNQVSLTCLVKGFYPSDIAVEWESNGQPENNYK

TTPPVLDSDGSFFLYSRLTVDKSRWQEGNVFSCSVMHEALHNHYTQKSLSLSLGKMFWVLVVVGGVLACYSLLVTVA
                                                                 CD28 TM(M)

FIIFWVRSKRSRGGHSDYMNMTPRRPGPTRKHYQPYAPPRDFAAYRSGGGRVKFSRSADAPAYQQGQNQLYNELNLG
     CD28 (GG)                                  CD3 zeta

RREEYDVLDKRRGRDPEMGGKPRRKNPQEGLYNELQKDKMAEAYSEIGMKGERRRGKGHDGLYQGLSTATKDTYDAL

HMQALPPR

FIG. 12B

MLLLVTSLLLCELPHPAFLLI PGPVPPSTAARELIEELFNITQNQKAPLCNGSMVWSINLTAGMYCAALESLINVSG

Signal Sequence      IL13(D7)

CSAIEKTKRMLSGFCPHKVSAGQFPSLHVKKTRIEVAQFVKDLLIHLRKLFKEGQFNESKYGPPCPPCPGGGSSGGG

IgG4(HL-CH3)

SGGQPREPQVYTLPPSQEEMTKNQVSLTCLVKGFYPSDIAVEWESNGQPENNYKTTPPVLDSGSFFLYSRLTVDKS

RWQEGNVFSCSVMHEALHNHYTQKSLSLSLGKMALIVLGGVAGLLLFIGLGIFFKRGRKKLLYIFKQPFMRPVQTTQ

CD4 TM                      41-BB

EEDGCSCRFPEEEEGGCELGGGRVKFSRSADAPAYQQGQNQLYNELNLGRREEYDVLDKRRGRDPEMGGKPRRKNPQ

CD3 ZETA

EGLYNELQKDKMAEAYSEIGMKGERRRGKGHDGLYQGLSTATKDTYDALHMQALPPRLEGGGEGRGSLLTCGDVEEN

T2A-CD19t(BspEI)

PGPRMPPPRLLFFLLFLTPMEVRPEEPLVVKVEEGDNAVLQCLKGTSDGPTQQLTWSRESPLKPFLKLSLGLPGLGI
HMRPLAIWLFIFNVSQQMGGFYLCQPGPPSEKAWQPGWTVNVEGSGELFRWNVSDLGGLGCGLKNRSSEGPSSPSGK
LMSPKLYVWAKDRPEIWEGEPPCVPPRDSLNQSLSQDLTMAPGSTLWLSCGVPPDSVSRGPLSWTHVHPKGPKSLLS
LELKDDRPARDMWVMETGLLLPRATAQDAGKYYCHRGNLTMSFHLEITARPVLWHWLLRTGGWKVSAVTLAYLIFCL
CSLVGILHLQRALVLRRKR

FIG. 13A

PGPVPPSTAARELIEELFNITQNQKAPLCNGSMVWSINLTAGMYCAALESLINVSG

IL13(D7)

CSAIEKTKRMLSGFCPHKVSAGQFPSLHVKKTRIEVAQFVKDLLIHLRKLFKEGQFNESKYGPPCPPCPGGGSSGGG

IgG4(HL-CH3)

SGGQPREPQVYTLPPSQEEMTKNQVSLTCLVKGFYPSDIAVEWESNGQPENNYKTTPPVLDSGSFFLYSRLTVDKS

RWQEGNVFSCSVMHEALHNHYTQKSLSLSLGKMALIVLGGVAGLLLFIGLGIFFKRGRKKLLYIFKQPFMRPVQTTQ

CD4 TM                      41-BB

EEDGCSCRFPEEEEGGCELGGGRVKFSRSADAPAYQQGQNQLYNELNLGRREEYDVLDKRRGRDPEMGGKPRRKNPQ

CD3 ZETA

EGLYNELQKDKMAEAYSEIGMKGERRRGKGHDGLYQGLSTATKDTYDALHMQALPPR

FIG. 13B

TARGETED CHIMERIC ANTIGEN RECEPTOR MODIFIED T CELLS FOR TREATMENT OF IL13Rα2 POSITIVE MALIGNANCIES

CLAIM OF PRIORITY

This application is a U.S. National Phase application under 35 U.S.C. § 371 of International Application No. PCT/US2021/014008, filed on Jan. 19, 2021, which claims the benefit of U.S. Provisional Application No. 62/968,975, filed on Jan. 31, 2020. The entire contents of the foregoing are incorporated herein by reference.

SEQUENCE LISTING

This application contains a Sequence Listing that has been submitted electronically as an ASCII text file named 40056-0055US1_ST25.txt. The ASCII text file, created on May 12, 2025, is 86,698 bytes in size. The material in the ASCII text file is hereby incorporated by reference in its entirety.

TECHNICAL FIELD

This disclosure concerns chimeric antigen receptors (CAR) engineered that bind to IL13 receptor, T cells expressing such CAR, methods of formulating such CART cells, and methods of use as anti-cancer agents.

BACKGROUND

IL13Rα2 (Lupardus, Birnbaum et al. 2010), which is a versatile therapeutic target due to its rare expression in normal tissue (Debinski and Gibo 2000) and overexpression in many human cancers, including glioblastoma multiforme (GBM) (Thaci, Brown et al. 2014), pancreatic ductal adenocarcinoma (Shimamura, Fujisawa et al. 2010), melanoma (Beard, Abate-Daga et al. 2013), ovarian carcinoma (Kioi, Kawakami et al. 2006), clear cell renal cell carcinoma (Shibasaki, Yamasaki et al. 2015), breast cancer (Papageorgis, Ozturk et al. 2015), and lung cancer (Xie, Wu et al. 2015). A second IL13 receptor family member, IL13Rα1, interacts with IL13 with lower affinity (Lupardus, Birnbaum et al. 2010), and is ubiquitously expressed in healthy tissue (Debinski and Gibo 2000). Additionally, IL13Rα1 and IL4Rα, a receptor pair that binds IL13 with high affinity (Lupardus, Birnbaum et al. 2010) to mediate signaling through the JAK/STAT6 pathway (Murata, Taguchi et al. 1998), are co-expressed in pulmonary tissue (Hecker, Zaslona et al. 2010). Despite this wide expression of IL13 binding partners in healthy tissue, an IL13-ligand based CAR has shown safety in humans during clinical trials with locoregional central nervous system (CNS) delivery in GBM (Brown, Badie et al. 2015, Brown, Alizadeh et al. 2016), suggesting that toxicity from on-target/off-disease binding is not problematic in this context. However, for the treatment of systemic disease, the wide expression of IL13 binding partners outside of the diseased tissue could act as a sink for IL13-based therapy, resulting in safety concerns and possibly impeding trafficking to the disease site. Previous work in the field has attempted to address this problem by generating CARs derived from IL13 mutants containing mutations to direct binding away from IL13Rα1/IL4Rα. Mutations at E13 have yielded improved selectivity for IL13Rα2 over IL13Rα1 (Kahlon, Brown et al. 2004, Krebs, Chow et al. 2014), albeit with the E13Y mutation still allowing measurable recognition of IL13Rα1 in the context of both recombinant antigen and antigen-expressing cancer cells (Krebs, Chow et al. 2014). The addition of both E13K and R109K mutations into an IL13-based CAR also showed attenuated, but not abolished, recognition of IL13Rα1-expressing cancer cells relative to IL13Rα2-expressing cancer cells (Kong, Sengupta et al. 2012). While these examples are encouraging, additional mutations will be required to develop an IL13Rα2-specific IL13 mutant. Among the challenges in developing such molecules is that the impact of IL13 mutations on the function of an IL13 containing CAR cannot be predicted.

SUMMARY

Described herein are IL13Rα2 targeted CAR that include a variant IL13 ("variant IL13 CAR") to treat a variety of cancers.

The variant IL13 CAR described herein include a variant IL-13 comprising or consisting of the amino acid sequence: GPVPPSTAVRELIEELVNITQNQKAPLCNGSMVWS-INLTAGMYCAALESLINVSGCS AIEKTQRMLSGFCPHKVSAGQFSSLHVRDTRIEV-AQFVKDLLNHLKELFTEGQFN (SEQ ID NO: 26); or comprising or consisting of the amino acid sequence: GPVPPSTAARELIEELFNITQNQKAPLCNGSMVWS-INLTAGMYCAALESLINVSGCS AIEKTKRMLSGFCPHKVSAGQFPSLHVKKTRIEV-AQFVKDLLIHLRKLFKEGQFN (SEQ ID NO: 27).

Described herein is an IL13 CAR comprising a variant IL13 comprising the amino acid sequence of SEQ ID NO: 26 or 27, a spacer (e.g., comprising SEQ ID NO: 9, 10, 11 or 12), a transmembrane domain (e.g., comprising SEQ ID NO: 14, 15 or 22), a 41-BB co-stimulatory domain (comprising SEQ ID NO:42) and a CD3 zeta cytoplasmic domain (SEQ ID NO: 21).

Described herein is a nucleic acid molecule comprising a nucleotide sequence encoding a chimeric antigen receptor (CAR), wherein the chimeric antigen receptor comprises: a targeting domain comprising SEQ ID NO: 26 or SEQ ID NO: 27, a spacer, a transmembrane domain, a co-stimulatory domain, and a CD3ζ signaling domain. In various embodiments: the transmembrane domain is selected from: a CD4 transmembrane domain or variant thereof having 1-5 amino acid modifications, a CD8 transmembrane domain or variant thereof having 1-5 amino acid modifications, a CD28 transmembrane domain or a variant thereof having 1-5 amino acid modifications; the wherein the IL13 receptor targeting domain consists of the amino acid sequence of SEQ ID NO: 26 or SEQ ID NO: 27; the costimulatory domain is selected from: a 41BB costimulatory domain or variant thereof having 1-5 amino acid modifications, a CD28 costimulatory domain or variant thereof having 1-5 amino acid modifications; wherein the costimulatory domain is a 41BB costimulatory domain; the 41BB costimulatory domain comprises the amino acid sequence of SEQ ID NO: 24 or a variant thereof having 1-5 amino acid modifications; the CD3ζ signaling domain comprises the amino acid sequence of SEQ ID NO:21; a linker of 3 to 15 amino acids is located between the 4-1BB costimulatory domain and the CD3ζ signaling domain or variant thereof; the CAR comprises the amino acid sequence of SEQ ID NO: 28-39, or a variant thereof having 1-5 amino acid modifications; the CAR comprises an amino acid sequence that is least about 80%, 85%, 90%, 95%, 96%, 97%, 98%, 99%, or 100% identical SEQ ID NO: 28; the CAR comprises an amino acid sequence that is least about 80%, 85%, 90%, 95%, 96%, 97%, 98%, 99%, or 100% identical SEQ ID NO: 29; the CAR comprises an amino acid sequence that is least about 80%, 85%, 90%, 95%, 96%, 97%, 98%, 99%, or 100% identical SEQ ID NO: 30; the CAR comprises an amino acid sequence that is least about 80%, 85%, 90%, 95%, 96%, 97%, 98%, 99%, or 100% identical SEQ ID NO: 31; the CAR comprises an amino acid sequence that is least about 80%, 85%, 90%, 95%, 96%, 97%, 98%, 99%, or 100% identical SEQ ID NO: 32; the CAR comprises an amino acid sequence that is least about 80%, 85%, 90%, 95%, 96%, 97%, 98%, 99%, or 100% identical SEQ ID NO: 33; the CAR comprises an amino acid sequence that is least about 80%, 85%, 90%, 95%, 96%, 97%, 98%, 99%, or 100% identical SEQ ID NO: 34; the CAR comprises an amino acid sequence that is least about 80%, 85%, 90%, 95%, 96%, 97%, 98%, 99%, or 100% identical SEQ ID NO: 35; the CAR comprises an amino acid sequence that is least about 80%, 85%, 90%, 95%, 96%, 97%, 98%, 99%, or 100% identical SEQ ID NO: 36; the CAR comprises an amino acid sequence that is least about 80%, 85%, 90%, 95%, 96%, 97%, 98%, 99%, or 100% identical SEQ ID NO: 37; the CAR comprises an amino acid sequence that is least about 80%, 85%, 90%, 95%, 96%, 97%, 98%, 99%, or 100% identical SEQ ID NO: 38; the CAR comprises an amino acid sequence that is least about 80%, 85%, 90%, 95%, 96%, 97%, 98%, 99%, or 100% identical SEQ ID NO:39. Also described is an expression vector comprising any of the forgoing nucleic acid molecules. Also described is a viral vector comprising any of the forgoing nucleic acid molecules.

Also described is a population of human T cells containing any of the forgoing nucleic acid molecules. Also described is a population of human T cells containing any of the forgoing expression vectors or viral vectors. In various embodiments, the population of human T cells comprise central memory T cells, naive memory T cells, pan T cells, or PBMC substantially depleted for CD25+ cells and CD14+ cells.

Also described is a method of treating a patient suffering from glioblastoma, pancreatic ductal adenocarcinoma, melanoma, ovarian carcinoma, renal cell carcinoma, breast cancer or lung cancer, comprising administering a population of autologous or allogeneic human T cells harboring a nucleic acid described herein. In various embodiments, the chimeric antigen receptor is administered locally or systemically; and the chimeric antigen receptor is administered by single or repeat dosing. In various embodiments, the chimeric antigen receptor substantially spares cells expressing IL13Rα1 that do not express IL13Rα2.

Also described herein is a method of preparing CAR T cells comprising: providing a population of autologous or allogeneic human T cells and transducing the T cells by a vector comprising the nucleic acid molecule of claim 1.

Also described are T cells harboring a vector expressing the variant IL13 CAR. In various embodiments: at least 20%, 30%, or 40% of the transduced human T cells are central memory T cells; at least 30% of the transduced human T cells are CD4+ and CD62L+ or CD8+ and CD62L+. In various embodiments: the population of human T cells comprise a vector expressing a chimeric antigen receptor comprising an amino acid sequence selected from SEQ ID NOs: 27, 29, 30, and 31) or a variant thereof having 1-5 amino acid modifications (e.g., 1 or 2) amino acid modifications (e.g., substitutions); the population of human T cells comprises central memory T cells ($T_{CM}$ cells) e.g., at least 20%, 30%, 40%, 50% 60%, 70%, 80% of the cells are $T_{CM}$ cells, or the population of T cells comprises a combination of central memory T cells, naïve T cells and stem central memory cells ($T_{CM/SCM/N}$ cells) e.g., at least 20%, 30%, 40%, 50% 60%, 70%, 80% of the cells are $T_{CM/SCM/N}$ cells. In some embodiments, the population of T cells includes both CD4+ cells and CD8+ cells (e.g., at least 20% of the CD3+ T cells are CD4+ and at least 3% of the CD3+ T cells are CD8+ and at least 70, 80 or 90% are either CD4+ or CD8+; at least 15%, 20%, 25%, 30%, 35%, 40%, 50%, 60% of the cells CD3+ cells are CD4+ and at least 4%, 5%, 8%, 10%, 20 of the CD3+ cells are CD8+ cells). In some embodiments, the population of human T cells are autologous to the patient. In some embodiments, the population of human T cells are allogenic to the patient.

IL13Rα2 Targeted CAR

The CAR described herein include a variant IL-13 comprising or consisting of the amino acid sequence: GPVPPSTAVRELIEELVNITQNQKAPLCNGSMVWS-INLTAGMYCAALESLINVSGCS AIEKTQRMLSGFCPHKVSAGQFSSLHVRDTRIEV-AQFVKDLLNHLKELFTEGQFN (SEQ ID NO: 26); or comprising or consisting of the amino acid sequence GPVPPSTAARELIEELFNITQNQKAPLCNGSMVWS-INLTAGMYCAALESLINVSGCS AIEKTKRMLSGFCPHKVSAGQFPSLHVKKTRIEV-AQFVKDLLIHLRKLFKEGQFN (SEQ ID NO: 27) and the sequence.

A useful IL13 variant CAR can consist of or comprises the amino acid sequence of SEQ ID NO: 29, 32, 35 or 38 (mature CAR lacking a signal sequence) or the IL13 variant CAR can consist of or comprise the amino acid sequence of SEQ ID NO: 30, 33, 36 or 39 (immature CAR having a GMCSFRa signal sequence). Thus, thee CAR and can be expressed in a form that includes a signal sequence, e.g., a human GM-CSF receptor alpha signal sequence (MLLLVT-SLLLCELPHPAFLLIP; SEQ ID NO:1). The CAR can be expressed with additional sequences that are useful for monitoring expression, for example, a T2A skip sequence and a truncated EGFRt. The CAR can be expressed with additional sequences that are useful for monitoring expression, for example, a T2A skip sequence and a truncated CD19t, e.g., SEQ ID NOs: 28, 31, 34 and 37. The variant IL13 CAR can comprise or consist of the amino acid sequence of any of SEQ ID NOs 28-29 with up to 1, 2, 3, 4 or 5 amino acid changes (preferably conservative amino acid changes).

In some embodiments, the nucleic acid encoding amino acid sequences SEQ ID NOs: 28-29 are codon optimized for expression in human cells.

Spacer Region

The CAR described herein can include a spacer located between the variant IL13 domain (i.e., a variant IL13 comprising SEQ ID NO: xC4 or xD7) and the transmembrane domain. A variety of different spacers can be used. Some of them include at least portion of a human Fc region, for example a hinge portion of a human Fc region or a CH3 domain or variants thereof. Table 1 below provides various spacers that can be used in the CARs described herein.

TABLE 1

Examples of Spacers

| Name | Length | Sequence |
|---|---|---|
| a3 | 3 aa | AAA |
| linker | 10 aa | GGGSSGGGSG (SEQ ID NO: 2) |

TABLE 1-continued

Examples of Spacers

| Name | Length | Sequence |
|---|---|---|
| IgG4 hinge (S→P) (S228P) | 12 aa | ESKYGPPCPPCP (SEQ ID NO: 3) |
| IgG4 hinge | 12 aa | ESKYGPPCPSCP (SEQ ID NO: 4) |
| IgG4 hinge (S228P) + linker | 22 aa | ESKYGPPCPPCPGGGSSGGGSG (SEQ ID NO: 5) |
| CD28 hinge | 39 aa | IEVMYPPPYLDNEKSNGTIIHVKGKHL CPSPLFPGPSKP (SEQ ID NO: 6) |
| CD8 hinge-48 aa | 48 aa | AKPTTTPAPRPPTPAPTIASQPLSLRP EACRPAAGGAVHTRGLDFACD (SEQ ID NO: 7) |
| CD8 hinge-45 aa | 45 aa | TTTPAPRPPTPAPTIASQPLSLRPEAC RPAAGGAVHTRGLDFACD (SEQ ID NO: 8) |
| IgG4(HL-CH3) (includes S228P in hinge) | 129 aa | ESKYGPPCPPCPGGGSSGGGSGGQPRE PQVYTLPPSQEEMTKNQVSLTCLVKGF YPSDIAVEWESNGQPENNYKTTPPVLD SDGSFFLYSRLTVDKSRWQEGNVFSCS VMHEALHNHYTQKSLSLSLGK (SEQ ID NO: 9) |
| IgG4(L235E, N297Q) | 229 aa | ESKYGPPCPSCPAPEFEGGPSVFLFPP KPKDTLMISRTPEVTCVVVDVSQEDPE VQFNWYVDGVEVHQAKTKPREEQFQST YRVVSVLTVLHQDWLNGKEYKCKVSNK GLPSSIEKTISKAKGQPREPQVYTLPP SQEEMTKNQVSLTCLVKGFYPSDIAVE WESNGQPENNYKTTPPVLDSDGSFFLY SRLTVDKSRWQEGNVFSCSVMHEALHN HYTQKSLSLSLGK (SEQ ID NO: 10) |
| IgG4(S228P, L235E, N297Q) | 229 aa | ESKYGPPCPPCPAPEFEGGPSVFLFPP KPKDTLMISRTPEVTCVVVDVSQEDPE VQFNWYVDGVEVHQAKTKPREEQFQST YRVVSVLTVLHQDWLNGKEYKCKVSNK GLPSSIEKTISKAKGQPREPQVYTLPP SQEEMTKNQVSLTCLVKGFYPSDIAVE WESNGQPENNYKTTPPVLDSDGSFFLY SRLTVDKSRWQEGNVFSCSVMHEALHN HYTQKSLSLSLGK (SEQ ID NO: 11) |
| IgG4(CH3) | 107 aa | GQPREPQVYTLPPSQEEMTKNQVSLTC LVKGFYPSDIAVEWESNGQPENNYKTT PPVLDSDGSFFLYSRLTVDKSRWQEGN VFSCSVMHEALHNHYTQKSLSLSLGK (SEQ ID NO: 12) |

Some spacer regions include all or part of an immunoglobulin (e.g., IgG1, IgG2, IgG3, IgG4) hinge region, i.e., the sequence that falls between the CH1 and CH2 domains of an immunoglobulin, e.g., an IgG4 Fc hinge or a CD8 hinge. Some spacer regions include an immunoglobulin CH3 domain or both a CH3 domain and a CH2 domain. The immunoglobulin derived sequences can include one or more amino acid modifications, for example, 1, 2, 3, 4 or 5 substitutions, e.g., substitutions that reduce off-target binding.

The hinge/linker region can also comprise a IgG4 hinge region having the sequence ESKYGPPCPSCP (SEQ ID NO:4) or ESKYGPPCPPCP (SEQ ID NO:3). The hinge/linker region can also comprise the sequence ESKYGPPCPPCP (SEQ ID NO:3) followed by the linker sequence GGGSSGGGSG (SEQ ID NO:2) followed by IgG4 CH3 sequence GQPREPQVYTLPPSQEEMTKNQVSLT-CLVKGFYPSDIAVEWESNGQPENNYKTTPPV LDSDGSFFLY-SRLTVDKSRWQEGNVFSCSVMHEALHN-HYTQKSLSLSLGK (SEQ ID NO:12). Thus, the entire linker/spacer region can comprise the sequence: ESKY-GPPCPPCPGGGSSGGGSGGQPREPQVYTLPP-SQEEMTKNQVSLTCLVKGFYPS DIAVEWESNGQPEN-NYKTTPPVLDSDGSFFLYSRLTVDKSRWQEGN VFSCSVMHEA LHNHYTQKSLSLSLGK (SEQ ID NO:11). In some cases, the spacer has 1, 2, 3, 4, or 5 single amino acid changes (e.g., conservative changes) compared to SEQ ID NO: 10 or 11. In some cases, the IgG4 Fc hinge/linker region is mutated at two positions (L235E; N297Q) in a manner that reduces binding by Fc receptors (FcRs) (e.g., comprises or consists of SEQ ID NO: 10 or 11).

Transmembrane Domain

A variety of transmembrane domains can be used in the. Table 2 includes examples of suitable transmembrane domains. Where a spacer region is present, the transmembrane domain (TM) is located carboxy terminal to the spacer region.

TABLE 2

Examples of Transmembrane Domains

| Name | Accession | Length | Sequence |
|---|---|---|---|
| CD3z | J04132.1 | 21 aa | LCYLLDGILFIYGVILTAL FL (SEQ ID NO: 13) |
| CD28 | NM_006139 | 27 aa | FWVLVVVGGVLACYSLLVT VAFIIFWV (SEQ ID NO: 14) |
| CD28(M) | NM_006139 | 28 aa | MFWVLVVVGGVLACYSLLV TVAFIIFWV (SEQ ID NO: 15) |
| CD4 | M35160 | 22 aa | MALIVLGGVAGLLLFIGLG IFF (SEQ ID NO: 16) |
| CD8tm | NM_001768 | 21 aa | IYIWAPLAGTCGVLLLSLV IT (SEQ ID NO: 17) |
| CD8tm2 | NM_001768 | 23 aa | IYIWAPLAGTCGVLLLSLV ITLY (SEQ ID NO: 18) |
| CD8tm3 | NM_001768 | 24 aa | IYIWAPLAGTCGVLLLSLV ITLYC (SEQ ID NO: 19) |
| 41BB | NM_001561 | 27 aa | IISFFLALTSTALLFLLFF LTLRFSVV (SEQ ID NO: 20) |

Costimulatory Domain

The costimulatory domain can be any domain that is suitable for use with a CD3ζ signaling domain. In some cases the co-signaling domain is a 4-1BB co-signaling domain that includes a sequence that is at least 90%, at least 95%, at least 98% identical to or identical to: KRGRKKL-LYIFKQPFMRPVQTTQEEDGCSCRFPEEEEGGCEL (SEQ ID NO:24). In some cases, the 4-1BB co-signaling domain has 1, 2, 3, 4 of 5 amino acid changes (preferably conservative) compared to SEQ ID NO:24.

The costimulatory domain(s) are located between the transmembrane domain and the CD3ζ signaling domain. Table 3 includes examples of suitable costimulatory domains together with the sequence of the CD3ζ signaling domain.

TABLE 3

CD3ζ Domain and Examples of Costimulatory Domains

| Name | Accession | Length | Sequence |
|---|---|---|---|
| CD3ζ | J04132.1 | 113 aa | RVKFSRSADAPAYQQGQNQLY NELNLGRREEYDVLDKRRGRD PEMGGKPRRKNPQEGLYNELQ KDKMAEAYSEIGMKGERRRGK GHDGLYQGLSTATKDTYDALH MQALPPR (SEQ ID NO: 21) |
| CD28 | NM_006139 | 42 aa | RSKRSRLLHSDYMNMTPRRPG PTRKHYQPYAPPRDFAAYRS (SEQ ID NO: 22) |
| CD28gg* | NM_006139 | 42 aa | RSKRSRGGHSDYMNMTPRRPG PTRKHYQPYAPPRDFAAYRS (SEQ ID NO: 23) |
| 41BB | NM_001561 | 42 aa | KRGRKKLLYIFKQPFMRPVQT TQEEDGCSCRFPEEEEGGCEL (SEQ ID NO: 24) |
| OX40 | | 42 aa | ALYLLRRDQRLPPDAHKPPGG GSFRTPIQEEQADAHSTLAKI (SEQ ID NO: 25) |

In various embodiments: the costimulatory domain is selected from the group consisting of: a costimulatory domain depicted in Table 3 or a variant thereof having 1-5 (e.g., 1 or 2) amino acid modifications, a CD28 costimulatory domain or a variant thereof having 1-5 (e.g., 1 or 2) amino acid modifications, a 4-1BB costimulatory domain or a variant thereof having 1-5 (e.g., 1 or 2) amino acid modifications and an OX40 costimulatory domain or a variant thereof having 1-5 (e.g., 1 or 2) amino acid modifications. In certain embodiments, a 4-1BB costimulatory domain or a variant thereof having 1-5 (e.g., 1 or 2) amino acid modifications in present. In some embodiments there are two costimulatory domains, for example a CD28 co-stimulatory domain or a variant thereof having 1-5 (e.g., 1 or 2) amino acid modifications (e.g., substitutions) and a 4-1BB co-stimulatory domain or a variant thereof having 1-5 (e.g., 1 or 2) amino acid modifications (e.g., substitutions). In various embodiments the 1-5 (e.g., 1 or 2) amino acid modification are substitutions. The costimulatory domain is amino terminal to the CD3ζ signaling domain and a short linker consisting of 2-10, e.g., 3 amino acids (e.g., GGG) is can be positioned between the costimulatory domain and the CD3ζ signaling domain.

CD3ζ Signaling Domain

The CD3ζ Signaling domain can be any domain that is suitable for use with a CD3ζ signaling domain. In some cases, the CD3ζ signaling domain includes a sequence that is at least 90%, at least 95%, at least 98% identical to or identical to: RVKFSRSADAPAYQQGQNQLYNELNLGRREEY-DVLDKRRGRDPEMGGKPRRKNPQ EGLYNELQKDK-MAEAYSEIGMKGERRRGKGHDGLYQGLSTATKDTY-DALHMQAL PPR (SEQ ID NO:21). In some cases, the CD3ζ signaling has 1, 2, 3, 4 of 5 amino acid changes (preferably conservative) compared to SEQ ID NO:21.

Truncated EGFR and Truncated CD19

The CD3ζ signaling domain can be followed by a ribosomal skip sequence (e.g., LEGGGEGRGSLLTCGD-VEENPGR; SEQ ID NO:40) and a truncated EGFR having a sequence that is at least 90%, at least 95%, at least 98% identical to or identical to: LVTSLLLCELPHPAFLLIP-RKVCNGIGIGEFKDSLSINATNIKHFKNCTSISGDL-HILPVA FRGDSFTHTPPLDPQELDI-LKTVKEITGFLLIQAWPENRTDLHAFENLEII RGRTKQHG QFSLAVVSLNITSLGLRSLKEISDGDVI-ISGNKNLCYANTINWKKLFGTSGQKTKIISN RGEN-SCKATGQVCHALCSPEGCWGPEPRDCVSCRNVSR-GRECVDKCNLLEGEPREF VENSECIQCHPECLPQAMNITCTGRGPDNCI-QCAHYIDGPHCVKTCPAGVMGENNTL VWKY-ADAGHVCHLCHPNCTYGCTGPGLEGCPTNGPKIPSI-ATGMVGALLLLLVVAL GIGLFM (SEQ ID NO: 41). In some cases, the truncated EGFR has 1, 2, 3, 4 of 5 amino acid changes (preferably conservative) compared to SEQ ID NO: 41.

Alternatively the CD3ζ signaling domain can be followed by a ribosomal skip sequence (e.g., LEGGGEGRGSLLTCGDVEENPGR; SEQ ID NO:40) and a truncated CD19R having a sequence that is at least 90%, at least 95%, at least 98% identical to or identical to:

(SEQ ID NO: 42)
MPPPRLLFFLLFLTPMEVRPEEPLVVKVEEGDNAVLQCLKGTSDGPT

QQLTWSRESPLKPFLKLSLGLPGLGIHMRPLAIWLFIFNVSQQMGGF

YLCQPGPPSEKAWQPGWTVNVEGSGELFRWNVSDLGGLGCGLKNRSS

EGPSSPSGKLMSPKLYVWAKDRPEIWEGEPPCVPPRDSLNQSLSQDL

TMAPGSTLWLSCGVPPDSVSRGPLSWTHVHPKGPKSLLSLELKDDRP

ARDMWVMETGLLLPRATAQDAGKYYCHRGNLTMSFHLEITARPVLWH

WLLRTGGWKVSAVTLAYLIFCLCSLVGILHLQRALVLRRKR

An amino acid modification refers to an amino acid substitution, insertion, and/or deletion in a protein or peptide sequence. An "amino acid substitution" or "substitution" refers to replacement of an amino acid at a particular position in a parent peptide or protein sequence with another amino acid. A substitution can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The following are examples of various groupings of amino acids: 1) Amino acids with nonpolar R groups: Alanine, Valine, Leucine, Isoleucine, Proline, Phenylalanine, Tryptophan, Methionine; 2) Amino acids with uncharged polar R groups: Glycine, Serine, Threonine, Cysteine, Tyrosine, Asparagine, Glutamine; 3) Amino acids with charged polar R groups (negatively charged at pH 6.0): Aspartic acid, Glutamic acid; 4) Basic amino acids (positively charged at pH 6.0): Lysine, Arginine, Histidine (at pH 6.0). Another grouping may be those amino acids with phenyl groups: Phenylalanine, Tryptophan, and Tyrosine.

In some cases, the CAR can be produced using a vector in which the CAR open reading frame is followed by a T2A ribosome skip sequence and a truncated EGFR (EGFRt) or truncated CD19. (CD19t) In this arrangement, co-expression of EGFRt or CD19t provides an inert, non-immunogenic surface marker that allows for accurate measurement of gene modified cells, and enables positive selection of gene-modified cells, as well as efficient cell tracking of the therapeutic T cells in vivo following adoptive transfer. Efficiently controlling proliferation to avoid cytokine storm and off-target toxicity is an important hurdle for the success of T cell immunotherapy. The EGFRt or CD19t incorporated in the lentiviral vector can act as suicide gene to ablate the CAR+ T cells in cases of treatment-related toxicity.

The CAR described herein can be produced by any means known in the art, though preferably it is produced using recombinant DNA techniques. Nucleic acids encoding the several regions of the chimeric receptor can be prepared and assembled into a complete coding sequence by standard techniques of molecular cloning known in the art (genomic library screening, overlapping PCR, primer-assisted ligation, site-directed mutagenesis, etc.) as is convenient. The resulting coding region is preferably inserted into an expression vector and used to transform a suitable expression host cell line, preferably a T lymphocyte, and most preferably an autologous T lymphocyte.

Various T cell subsets isolated from the patient can be transduced with a vector for CAR expression. Central memory T cells are one useful T cell subset. Central memory T cell can be isolated from peripheral blood mononuclear cells (PBMC) by selecting for CD45RO+/CD62L+ cells, using, for example, the CliniMACS® device to immuno-magnetically select cells expressing the desired receptors. The cells enriched for central memory T cells can be activated with anti-CD3/CD28, transduced with, for example, a lentiviral vector that directs the expression of the CAR as well as a non-immunogenic surface marker for in vivo detection, ablation, and potential ex vivo selection. The activated/genetically modified CART T cells can be expanded in vitro with IL-2/IL-15 and then cryopreserved. Additional methods of preparing CAR T cells can be found in PCT/US2016/043392.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety for any and all purposes. In case of conflict, the present specification, including definitions, will control.

Other features and advantages of the invention will be apparent from the following detailed description and figures, and from the claims.

DESCRIPTION OF DRAWINGS

FIG. 1A-1C: Binding profile of IL13 D7 and IL13 C4 for IL13 receptors. (A) Structural superposition of the IL13/IL13Rα1 and IL13/IL13Rα2 complexes. The docking mode of IL13 with IL13Rα1 is essentially identical to its docking mode with IL13Rα2. Right inset boxes show amino acids on IL13 forming the IL13Rα1-IL13Rα2-site II and site III binding interfaces (yellow: IL13 binding IL13Rα1; green: IL13 binding IL13Rα2). IL13 uses the same amino acids to form the IL13Rα1- and IL13Rα2-site II and site III binding interface. (B) IL13 wild type binds with high efficiency IL13Rα1 and IL13Rα2. IL13 C4 and D7 specifically bind IL13Rα2. (C) IL13 variants binding parameters for IL13Rα1 and IL13Rα2 measured by surface plasmon resonance.

FIG. 10A-10B: Sequence of a CAR having C4 mutein targeting domain. Amino acid sequence of (A) IL13(C4)-IgG4(L235E,N297Q)-CD28gg-Zeta(CO)-T2A-CD19t, including the signal sequence and T2A-CD19t marker (SEQ ID NO: 28); and (B) same CAR without signal sequence and T2A-CD19t marker (SEQ ID NO: 29). In both cases, the various domains are indicated. The CAR sequence is in bold and the marker sequences is not. SEQ NO: 30 includes the signal sequence, but not the T2A-CD19t marker.

FIG. 11A-11B: Sequence of a CAR having C4 mutein targeting domain. Amino acid sequence of (A) IL13(C4)-IgG4(HL-CH3)-CD4tm-41BB-Zeta(CO)-T2A-CD19t (BspEI), including the signal sequence and T2A-CD19t (BspEI) marker (SEQ ID NO: 31); and (B) same CAR without signal sequence and T2A-CD19t (BspEI) marker (SEQ ID NO: 32). In both cases, the various domains are indicated. The CAR sequence is in bold and the marker sequences is not. SEQ NO: 33 includes the signal sequence, but not the T2A-CD19t marker.

FIG. 12A-12B: Sequence of a CAR having D7 mutein targeting domain. Amino acid sequence of (A) IL13(D7)-IgG4(L235E,N297Q)-CD28gg-Zeta(CO)-T2A-CD19t, including the signal sequence and T2A-CD19t marker (SEQ ID NO: 34); and (B) same CAR without signal sequence and T2A-CD19t marker (SEQ ID NO: 35). In both cases, the various domains are indicated. The CAR sequence is in bold and the marker sequences is not. SEQ NO: 36 includes the signal sequence, but not the T2A-CD19t marker.

FIG. 13A-13B: Sequence of a CAR having D7 mutein targeting domain. Amino acid sequence of (A) IL13(D7)-IgG4(HL-CH3)-CD4tm-41BB-Zeta(CO)-T2A-CD19t (BspEI), including the signal sequence and T2A-CD19t (BspEI) marker (SEQ ID NO: 37); and (B) same CAR without signal sequence and T2A-CD19t (BspEI) marker (SEQ ID NO: 38). In both cases, the various domains are indicated. The CAR sequence is in bold and the marker sequences is not. SEQ NO: 39 includes the signal sequence, but not the T2A-CD19t marker.

DETAILED DESCRIPTION

Figure 1A:
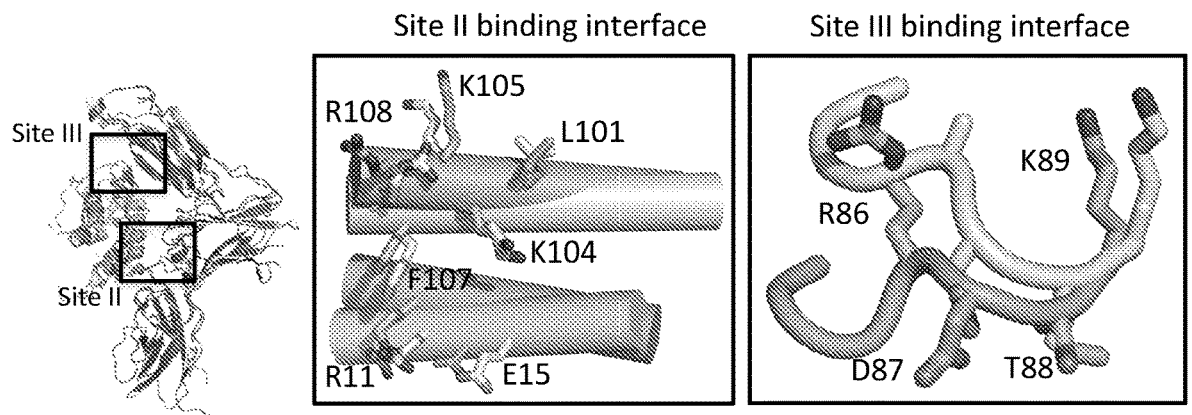

In this disclosure the generation and anti-tumor efficacy of CAR with a variant IL13 domain targeting IL13Rα2 are described. The CAR T cells exhibited potent antigen-dependent cytotoxicity against L13Rα2-expressing human cancer lines. In vivo delivery of the CAR T cells in a murine tumor model conferred elimination of antigen-positive disease and extension of overall survival.

IL13Rα2 Targeted CAR

The CAR described herein include a variant IL-13 comprising or consisting of the amino acid sequence: GPVPPSTAVRELIEELVNITQNQKAPLCNGSMVWSINLTAGMYCAALESLINVSGCSAIEKTQRMLSGFCPHKVSAGQFSSLHVRDTRIEVAQFVKDLLNHLKELFTEGQFN (SEQ ID NO: 26); or comprising or consisting of the amino acid sequence GPVPPSTAARELIEELFNITQNQKAPLCNGSMVWSINLTAGMYCAALESLINVSGCSAIEKTKRMLSGFCPHKVSAGQFPSLHVKKTRIEVAQFVKDLLIHLRKLFKEGQFN (SEQ ID NO: 27) and the sequence.

A useful IL13 variant CAR can consist of or comprises the amino acid sequence of SEQ ID NO: 29, 32, 35 or 38 (mature CAR lacking a signal sequence) or the IL13 variant CAR can consist of or comprise the amino acid sequence of SEQ ID NO: 30, 33, 36 or 39 (immature CAR having a GMCSFRa signal sequence). Thus, thee CAR and can be expressed in a form that includes a signal sequence, e.g., a human GM-CSF receptor alpha signal sequence (MLLLVTSLLLCELPHPAFLLIP; SEQ ID NO:1). The CAR can be expressed with additional sequences that are useful for monitoring expression, for example, a T2A skip sequence and a truncated EGFRt. The CAR can be expressed with additional sequences that are useful for monitoring expression, for example, a T2A skip sequence and a truncated CD19t, e.g., SEQ ID NOs: 28, 31, 34 and 37. The variant IL13 CAR can comprise or consist of the amino acid sequence of any of SEQ ID NOs 28-29 with up to 1, 2, 3, 4 or 5 amino acid changes (preferably conservative amino acid changes).

In some embodiments, the nucleic acid encoding amino acid sequences SEQ ID NOs: 28-29 are codon optimized for expression in human cells.

Spacer Region

The CAR described herein can include a spacer located between the variant IL13 domain (i.e., a variant IL13 comprising SEQ ID NO: xC4 or xD7) and the transmembrane domain. A variety of different spacers can be used. Some of them include at least portion of a human Fc region, for example a hinge portion of a human Fc region or a CH3 domain or variants thereof. Table 1 below provides various spacers that can be used in the CARs described herein.

TABLE 1

Examples of Spacers

| Name | Length | Sequence |
|---|---|---|
| a3 | 3 aa | AAA |
| linker | 10 aa | GGGSSGGGSG (SEQ ID NO: 2) |
| IgG4 hinge (S→P) (S228P) | 12 aa | ESKYGPPCPPCP (SEQ ID NO: 3) |
| IgG4 hinge | 12 aa | ESKYGPPCPSCP (SEQ ID NO: 4) |
| IgG4 hinge (S228P) + linker | 22 aa | ESKYGPPCPPCPGGGSS GGGSG (SEQ ID NO: 5) |

TABLE 1-continued

Examples of Spacers

| Name | Length | Sequence |
|---|---|---|
| CD28 hinge | 39 aa | IEVMYPPPYLDNEKSNG TIIHVKGKHLCPSPLFP GPSKP (SEQ ID NO: 6) |
| CD8 hinge-48 aa | 48 aa | AKPTTTPAPRPPTPAPT IASQPLSLRPEACRPAA GGAVHTRGLDFACD (SEQ ID NO: 7) |
| CD8 hinge-45 aa | 45 aa | TTTPAPRPPTPAPTIAS QPLSLRPEACRPAAGGA VHTRGLDFACD (SEQ ID NO: 8) |
| IgG4 (HL-CH3) Also called IgG4 (HL-ΔCH2) (includes S228P in hinge) | 129 aa | ESKYGPPCPPCPGGGSS GGGSGGQPREPQVYTLP PSQEEMTKNQVSLTCLV KGFYPSDIAVEWESNGQ PENNYKTTPPVLDSDGS FFLYSRLTVDKSRWQEG NVFSCSVMHEALHNHYT QKSLSLSLGK (SEQ ID NO: 9) |
| IgG4 (L235E, N297Q) | 229 aa | ESKYGPPCPSCPAPEFE GGPSVFLFPPKPKDTLM ISRTPEVTCVVVDVSQE DPEVQFNWYVDGVEVHN AKTKPREEQFQSTYRVV SVLTVLHQDWLNGKEYK CKVSNKGLPSSIEKTIS KAKGQPREPQVYTLPPS QEEMTKNQVSLTCLVKG FYPSDIAVEWESNGQPE NNYKTTPPVLDSDGSFF LYSRLTVDKSRWQEGNV FSCSVMHEALHNHYTQK SLSLSLGK (SEQ ID NO: 10) |
| IgG4 (S228P, L235E, N297Q) | 229 aa | ESKYGPPCPPCPAPEFE GGPSVFLFPPKPKDTLM ISRTPEVTCVVVDVSQE DPEVQFNWYVDGVEVHN AKTKPREEQFQSTYRVV SVLTVLHQDWLNGKEYK CKVSNKGLPSSIEKTIS KAKGQPREPQVYTLPPS QEEMTKNQVSLTCLVKG FYPSDIAVEWESNGQPE NNYKTTPPVLDSDGSFF LYSRLTVDKSRWQEGNV FSCSVMHEALHNHYTQK SLSLSLGK (SEQ ID NO: 11) |
| IgG4 (CH3) Also called IgG4 (ΔCH2) | 107 aa | GQPREPQVYTLPPSQEE MTKNQVSLTCLVKGFYP SDIAVEWESNGQPENNY KTTPPVLDSDGSFFLYS RLTVDKSRWQEGNVFSC SVMHEALHNHYTQKSLS LSLGK (SEQ ID NO: 12) |

Some spacer regions include all or part of an immunoglobulin (e.g., IgG1, IgG2, IgG3, IgG4) hinge region, i.e., the sequence that falls between the CH1 and CH2 domains of an immunoglobulin, e.g., an IgG4 Fc hinge or a CD8 hinge. Some spacer regions include an immunoglobulin CH3 domain (called CH3 or ΔCH2) or both a CH3 domain and a CH2 domain. The immunoglobulin derived sequences can include one or more amino acid modifications, for example, 1, 2, 3, 4 or 5 substitutions, e.g., substitutions that reduce off-target binding.

The hinge/linker region can also comprise an IgG4 hinge region having the sequence ESKYGPPCPSCP (SEQ ID NO:4) or ESKYGPPCPPCP (SEQ ID NO:3). The hinge/linger region can also comprise the sequence ESKYGPPCPPCP (SEQ ID NO:3) followed by the linker sequence GGGSSGGGSG (SEQ ID NO:2) followed by IgG4 CH3 sequence GQPREPQVYTLPPSQEEMTKNQVSLTCLVKGFYPSDIAVEWESNGQPENNYKTTPPVLDSDGSFFLY-SRLTVDKSRWQEGNVFSCSVMHEALHN-HYTQKSLSLSLGK (SEQ ID NO:12). Thus, the entire linker/spacer region can comprise the sequence: ESKYGPPCPPCPGGGSSGGGSGGQPREPQVYTLPP-SQEEMTKNQVSLTCLVKGFYPS DIAVEWESNGQPEN-NYKTTPPVLDSDGSFFLYSRLTVDKSRWQE GNVFSCSVMHEA LHNHYTQKSLSLSLGK (SEQ ID NO:11). In some cases, the spacer has 1, 2, 3, 4, or 5 single amino acid changes (e.g., conservative changes) compared to SEQ ID NO:11. In some cases, the IgG4 Fc hinge/linker region that is mutated at two positions (L235E; N297Q) in a manner that reduces binding by Fc receptors (FcRs).

Transmembrane Domain

A variety of transmembrane domains can be used in the. Table 2 includes examples of suitable transmembrane domains. Where a spacer region is present, the transmembrane domain (TM) is located carboxy terminal to the spacer region.

TABLE 2

Examples of Transmembrane Domains

| Name | Accession | Length | Sequence |
|---|---|---|---|
| CD3z | J04132.1 | 21 aa | LCYLLDGILFIYGVILTAL FL (SEQ ID NO: 13) |
| CD28 | NM_006139 | 27 aa | FWVLVVVGGVLACYSLLVT VAFIIFWV (SEQ ID NO: 14) |
| CD28(M) | NM_006139 | 28 aa | MFWVLVVVGGVLACYSLLV TVAFIIFWV (SEQ ID NO: 15) |
| CD4 | M35160 | 22 aa | MALIVLGGVAGLLLFIGLG IFF (SEQ ID NO: 16) |
| CD8tm | NM_001768 | 21 aa | IYIWAPLAGTCGVLLLSLV IT (SEQ ID NO: 17) |
| CD8tm2 | NM_001768 | 23 aa | IYIWAPLAGTCGVLLLSLV ITLY (SEQ ID NO: 18) |
| CD8tm3 | NM_001768 | 24 aa | IYIWAPLAGTCGVLLLSLV ITLYC (SEQ ID NO: 19) |
| 41BB | NM_001561 | 27 aa | IISFFLALTSTALLFLLFF LTLRFSVV (SEQ ID NO: 20) |

Costimulatory Domain

The costimulatory domain can be any domain that is suitable for use with a CD3ζ signaling domain. In some cases the co-signaling domain is a 4-1BB co-signaling domain that includes a sequence that is at least 90%, at least 95%, at least 98% identical to or identical to: KRGRKKLLYIFKQPFMRPVQTTQEEDGCSCRFPEEEEGGCEL (SEQ ID NO:24). In some cases, the 4-1BB co-signaling domain has 1, 2, 3, 4 of 5 amino acid changes (preferably conservative) compared to SEQ ID NO:24.

The costimulatory domain(s) are located between the transmembrane domain and the CD3 signaling domain. Table 3 includes examples of suitable costimulatory domains together with the sequence of the CD3ζ signaling domain.

TABLE 3

CD3ζ Domain and Examples of Costimulatory Domains

| Name | Accession | Length | Sequence |
|---|---|---|---|
| CD3ζ | J04132.1 | 113 aa | RVKFSRSADAPAYQQGQNQLY NELNLGRREEYDVLDKRRGRD PEMGGKPRRKNPQEGLYNELQ KDKMAEAYSEIGMKGERRRGK GHDGLYQGLSTATKDTYDALH MQALPPR (SEQ ID NO: 21) |
| CD28 | NM_006139 | 42 aa | RSKRSRLLHSDYMNMTPRRPG PTRKHYQPYAPPRDFAAYRS (SEQ ID NO: 22) |
| CD28gg* | NM_006139 | 42 aa | RSKRSRGGHSDYMNMTPRRPG PTRKHYQPYAPPRDFAAYRS (SEQ ID NO: 23) |
| 41BB | NM_001561 | 42 aa | KRGRKKLLYIFKQPFMRPVQT TQEEDGCSCRFPEEEEGGCEL (SEQ ID NO: 24) |
| OX40 | | 42 aa | ALYLLRRDQRLPPDAHKPPGG GSFRTPIQEEQADAHSTLAKI (SEQ ID NO: 25) |

In various embodiments: the costimulatory domain is selected from the group consisting of: a costimulatory domain depicted in Table 3 or a variant thereof having 1-5 (e.g., 1 or 2) amino acid modifications, a CD28 costimulatory domain or a variant thereof having 1-5 (e.g., 1 or 2) amino acid modifications, a 4-1BB costimulatory domain or a variant thereof having 1-5 (e.g., 1 or 2) amino acid modifications and an OX40 costimulatory domain or a variant thereof having 1-5 (e.g., 1 or 2) amino acid modifications. In certain embodiments, a 4-1BB costimulatory domain or a variant thereof having 1-5 (e.g., 1 or 2) amino acid modifications in present. In some embodiments there are two costimulatory domains, for example a CD28 co-stimulatory domain or a variant thereof having 1-5 (e.g., 1 or 2) amino acid modifications (e.g., substitutions) and a 4-1BB co-stimulatory domain or a variant thereof having 1-5 (e.g., 1 or 2) amino acid modifications (e.g., substitutions). In various embodiments the 1-5 (e.g., 1 or 2) amino acid modification are substitutions. The costimulatory domain is amino terminal to the CD3ζ signaling domain and a short linker consisting of 2-10, e.g., 3 amino acids (e.g., GGG) is can be positioned between the costimulatory domain and the CD3ζ signaling domain.

CD3ζ Signaling Domain

The CD3ζ Signaling domain can be any domain that is suitable for use with a CD3ζ signaling domain. In some cases, the CD3ζ signaling domain includes a sequence that is at least 90%, at least 95%, at least 98% identical to or identical to: RVKFSRSADAPAYQQGQNQLYNELNLGRREEY-DVLDKRRGRDPEMGGKPRRKNPQ EGLYNELQKDK-MAEAYSEIGMKGERRRGKGHDGLYQGLSTATKDTY-DALHMQAL PPR (SEQ ID NO:21). In some cases, the CD3ζ signaling has 1, 2, 3, 4 of 5 amino acid changes (preferably conservative) compared to SEQ ID NO:21.

Truncated EGFR and Truncated CD19

The CD3ζ signaling domain can be followed by a ribosomal skip sequence (e.g., LEGGGEGRGSLLTCGD-VEENPGPR; SEQ ID NO:40) and a truncated EGFR having a sequence that is at least 90%, at least 95%, at least 98% identical to or identical to: LVTSLLLCELPHPAFLLIP-RKVCNGIGIGEFKDSLSINATNIKHFKNCTSISGDL-HILPVA FRGDSFTHTPPLDPQELDI-LKTVKEITGFLLIQAWPENRTDLHAFENLEIIRGRTKQHG QFSLAVVSLNITSLGLRSLKEISDGDVIISGNKNLCYA-NTINWKKLFGTSGQKTKIISN RGENSCK-ATGQVCHALCSPEGCWGPEPRDCVSCRNVSR-GRECVDKCNLLEGEPREF VENSECIQCHPECLPQAMNITCTGRGPDNCI-QCAHYIDGPHCVKTCPAGVMGENNTL VWKY-ADAGHVCHLCHPNCTYGCTGPGLEGCPTNGPKIPSI-ATGMVGALLLLLVVAL GIGLFM (SEQ ID NO: 41). In some cases, the truncated EGFR has 1, 2, 3, 4 of 5 amino acid changes (preferably conservative) compared to SEQ ID NO: 41.

Alternatively the CD3ζ signaling domain can be followed by a ribosomal skip sequence (e.g., LEGGGEGRGSLLTCGDVEENPGPR; SEQ ID NO:40) and a truncated CD19R having a sequence that is at least 90%, at least 95%, at least 98% identical to or identical to:

```
                                              (SEQ ID NO: 42)
MPPPRLLFFLLFLTPMEVRPEEPLVVKVEEGDNAVLQCLKGT

SDGPTQQLTWSRESPLKPFLKLSLGLPGLGIHMRPLAIWLFI

FNVSQQMGGFYLCQPGPPSEKAWQPGWTVNVEGSGELFRWNV

SDLGGLGCGLKNRSSEGPSSPSGKLMSPKLYVWAKDRPEIWE

GEPPCVPPRDSLNQSLSQDLTMAPGSTLWLSCGVPPDSVSRG

PLSWTHVHPKGPKSLLSLELKDDRPARDMWVMETGLLLPRAT

AQDAGKYYCHRGNLTMSFHLEITARPVLWHWLLRTGGWKVSA

VTLAYLIFCLCSLVGILHLQRALVLRRKR
```

An amino acid modification refers to an amino acid substitution, insertion, and/or deletion in a protein or peptide sequence. An "amino acid substitution" or "substitution" refers to replacement of an amino acid at a particular position in a parent peptide or protein sequence with another amino acid. A substitution can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. The following are examples of various groupings of amino acids: 1) Amino acids with nonpolar R groups: Alanine, Valine, Leucine, Isoleucine, Proline, Phenylalanine, Tryptophan, Methionine; 2) Amino acids with uncharged polar R groups: Glycine, Serine, Threonine, Cysteine, Tyrosine, Asparagine, Glutamine; 3) Amino acids with charged polar R groups (negatively charged at pH 6.0): Aspartic acid, Glutamic acid; 4) Basic amino acids (positively charged at pH 6.0): Lysine, Arginine, Histidine (at pH 6.0). Another grouping may be those amino acids with phenyl groups: Phenylalanine, Tryptophan, and Tyrosine.

In some cases, the CAR can be produced using a vector in which the CAR open reading frame is followed by a T2A ribosome skip sequence and a truncated EGFR (EGFRt) or truncated CD19. (CD19t) In this arrangement, co-expression of EGFRt or CD19t provides an inert, non-immunogenic surface marker that allows for accurate measurement of gene modified cells, and enables positive selection of gene-modified cells, as well as efficient cell tracking of the therapeutic T cells in vivo following adoptive transfer. Efficiently controlling proliferation to avoid cytokine storm and off-target toxicity is an important hurdle for the success of T cell immunotherapy. The EGFRt or CD19t incorporated in the lentiviral vector can act as suicide gene to ablate the CAR+ T cells in cases of treatment-related toxicity.

The CAR described herein can be produced by any means known in the art, though preferably it is produced using recombinant DNA techniques. Nucleic acids encoding the several regions of the chimeric receptor can be prepared and assembled into a complete coding sequence by standard techniques of molecular cloning known in the art (genomic library screening, overlapping PCR, primer-assisted ligation, site-directed mutagenesis, etc.) as is convenient. The resulting coding region is preferably inserted into an expression vector and used to transform a suitable expression host cell line, preferably a T lymphocyte, and most preferably an autologous T lymphocyte.

Various T cell subsets isolated from the patient can be transduced with a vector for CAR expression. Central memory T cells are one useful T cell subset. Central memory T cell can be isolated from peripheral blood mononuclear cells (PBMC) by selecting for CD45RO+/CD62L+ cells, using, for example, the CliniMACS® device to immuno-magnetically select cells expressing the desired receptors. The cells enriched for central memory T cells can be activated with anti-CD3/CD28, transduced with, for example, a lentiviral vector that directs the expression of the CAR as well as a non-immunogenic surface marker for in vivo detection, ablation, and potential ex vivo selection. The activated/genetically modified CART T cells can be expanded in vitro with IL-2/IL-15 and then cryopreserved. Additional methods of preparing CAR T cells can be found in PCT/US2016/043392.

EXAMPLES

The invention is further described in the following examples, which do not limit the scope of the invention described in the claims.

Example 1: IL13 Variants Exhibit Selective Binding to IL13Rα2

Figure 1B:
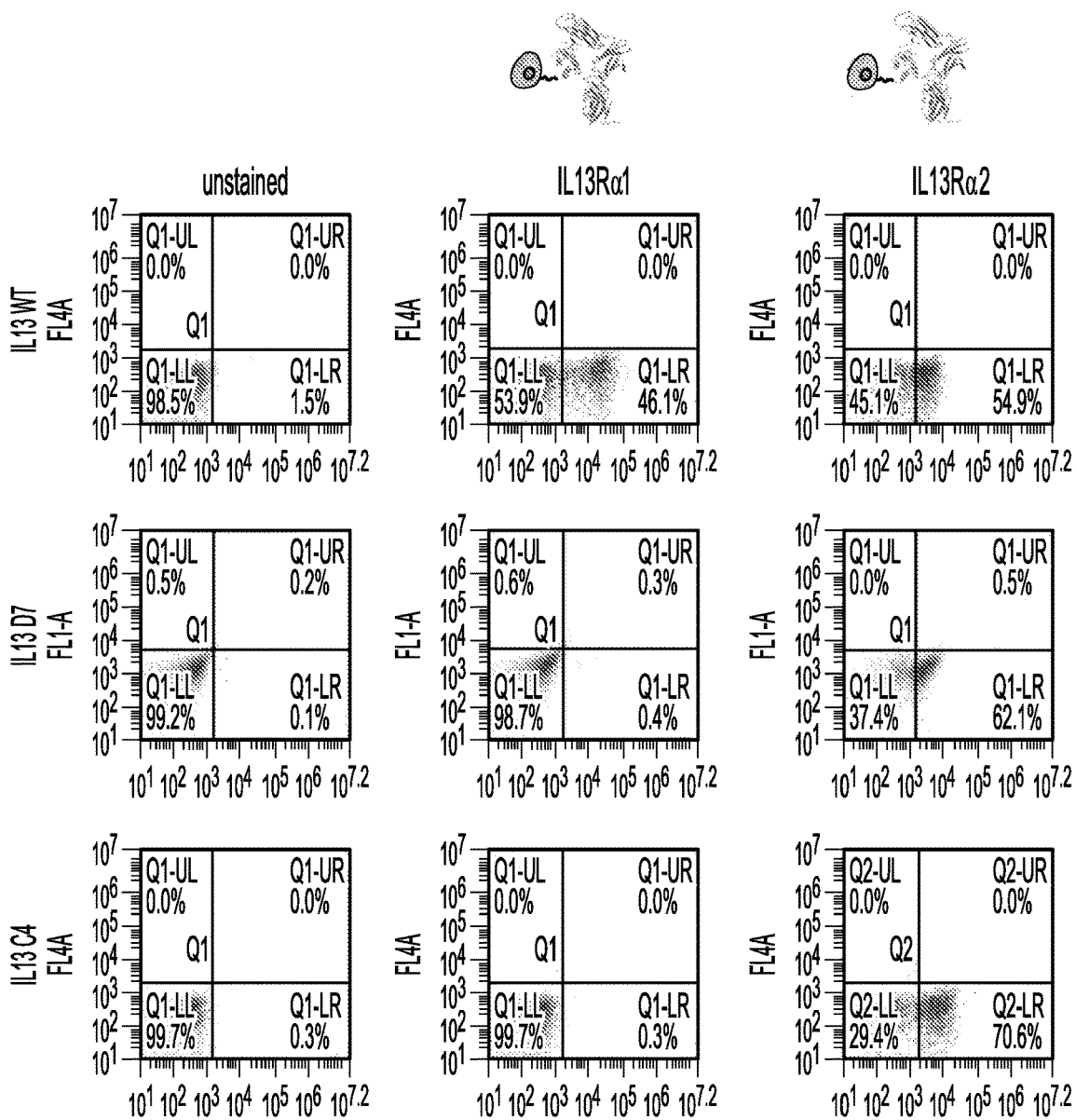
Figure 2A:
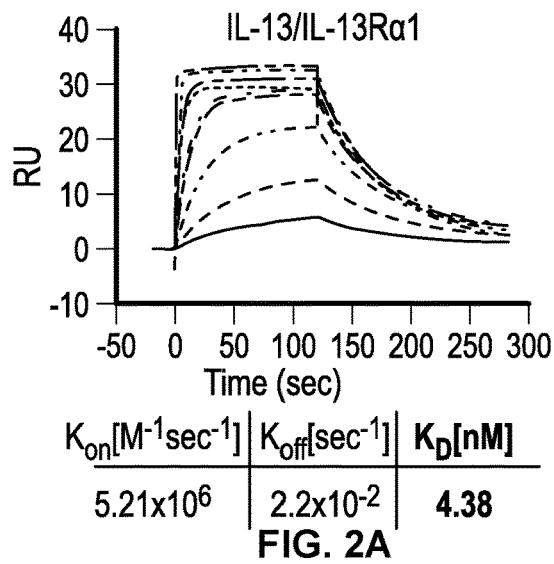
FIG. 2A-2F: IL-13Rα1 and IL-13Rα2 binding affinities of the IL-13 variant. (A-C) Surface plasmon resonance measurements of IL-13, IL-13 D7 and IL-13 C4 for IL-13Rα1. IL-13Rα1 was immobilized on the surface of the chip and the indicated doses of IL-13 or the two IL-13 mutants were flowed. (D-F) Surface plasmon resonance measurements of IL-13, IL-13 D7 and IL-13 C4 for IL-13Rα2. IL-13Rα2 was immobilized on the surface of the chip and the indicated doses of IL-13 or the two IL-13 mutants were flowed.
Figure 2B:
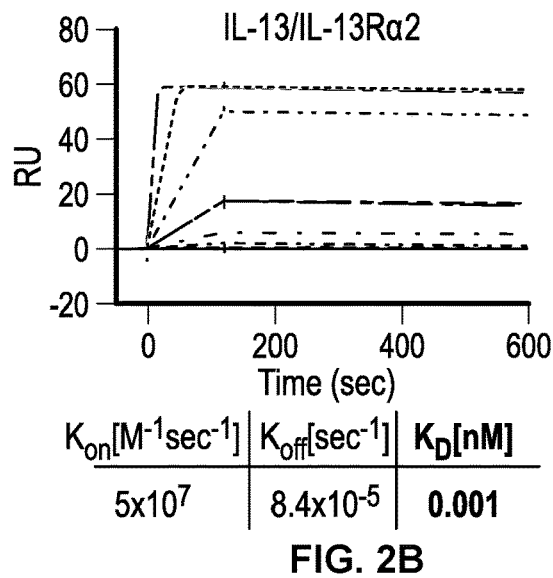
Figure 2C:
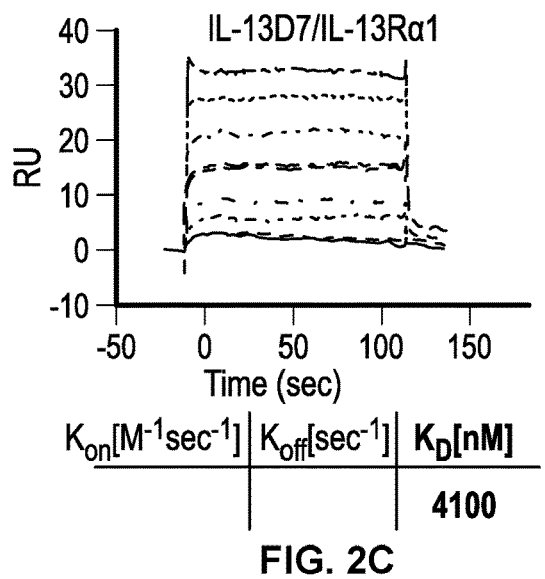
Figure 2D:
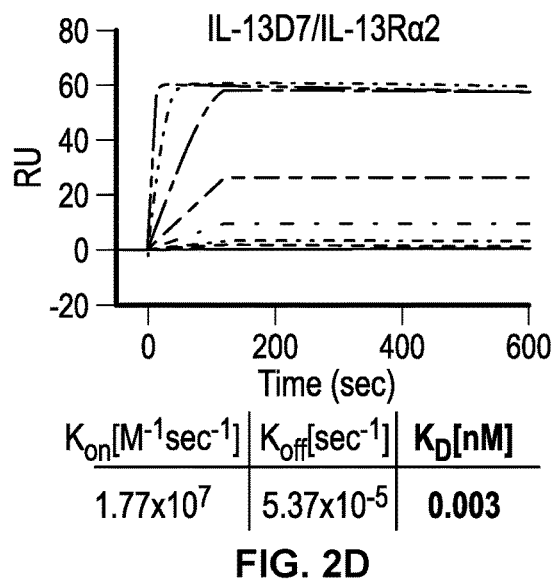
Figure 2E:
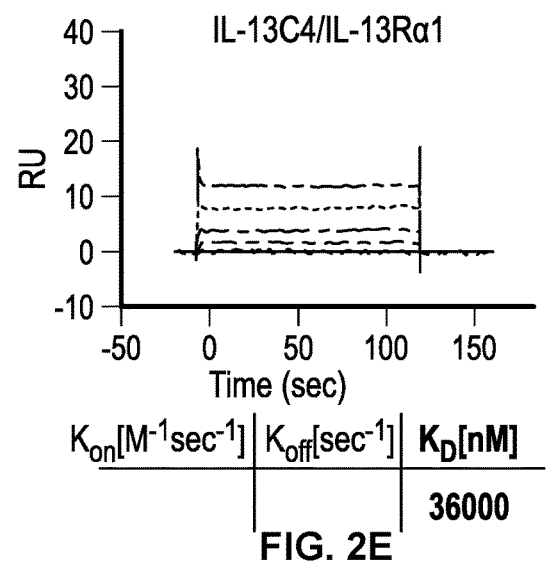
Figure 2F:
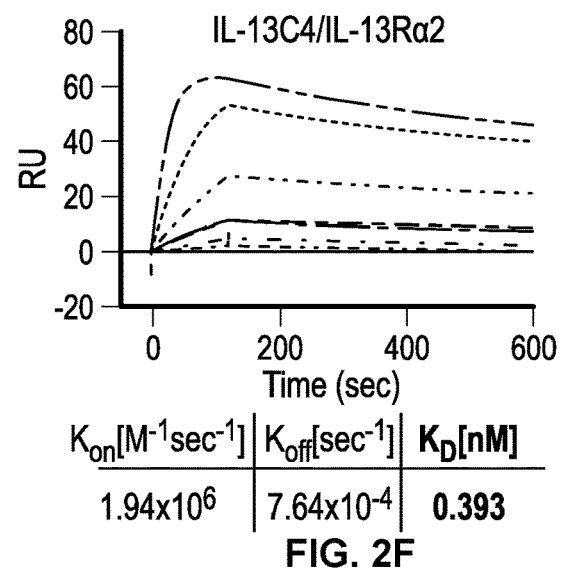
Figure 3A:
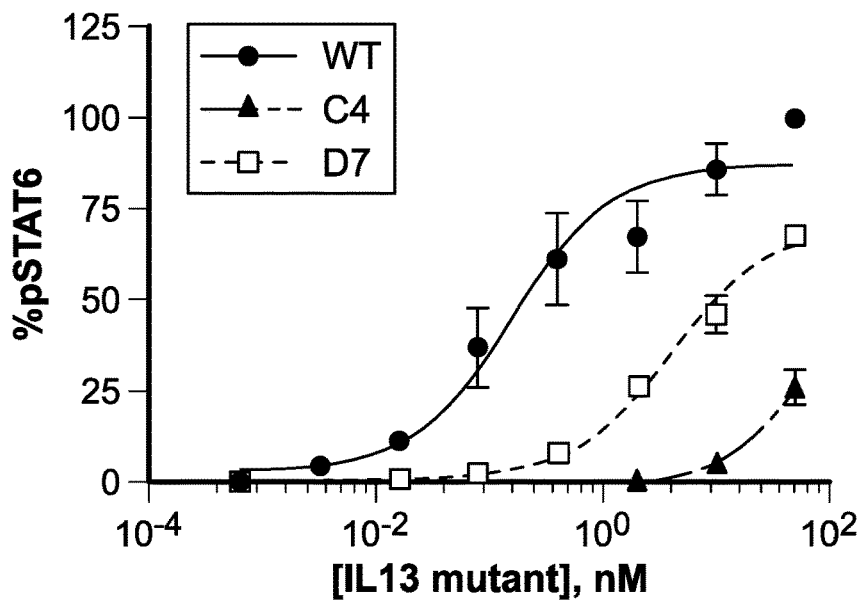
FIG. 3A-3C: Signal activation and activities potencies exhibited by the IL13 D7 and IL13 C4 muteins. (A) Levels of pSTAT6, measured by flow cytometry, induced by IL13 or the two IL13 mutants in A549 cells stimulated with the indicated doses for 15 min. Data are presented as mean±range of two replicates. (B) Levels of CCL26 gene induction induced by IL13 and the two mutants in the human fibroblast KA23 measured by qPCR. Data are presented as mean±range of two replicates. (C) Levels of TF-1 cell proliferation exhibited by IL13 and the two IL13 muteins after 96 hr of stimulation with the indicated doses. Data are presented as mean±range of two replica.
Figure 3B:
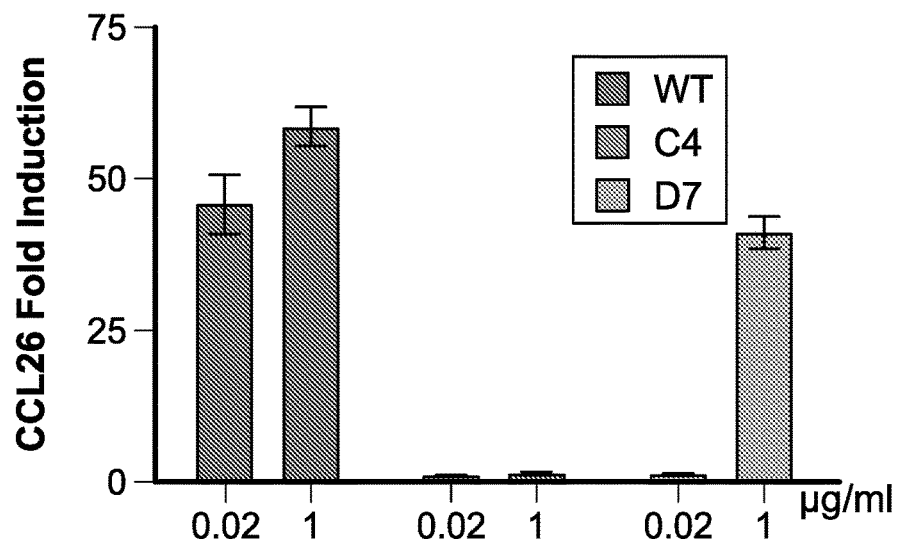
Figure 3C:
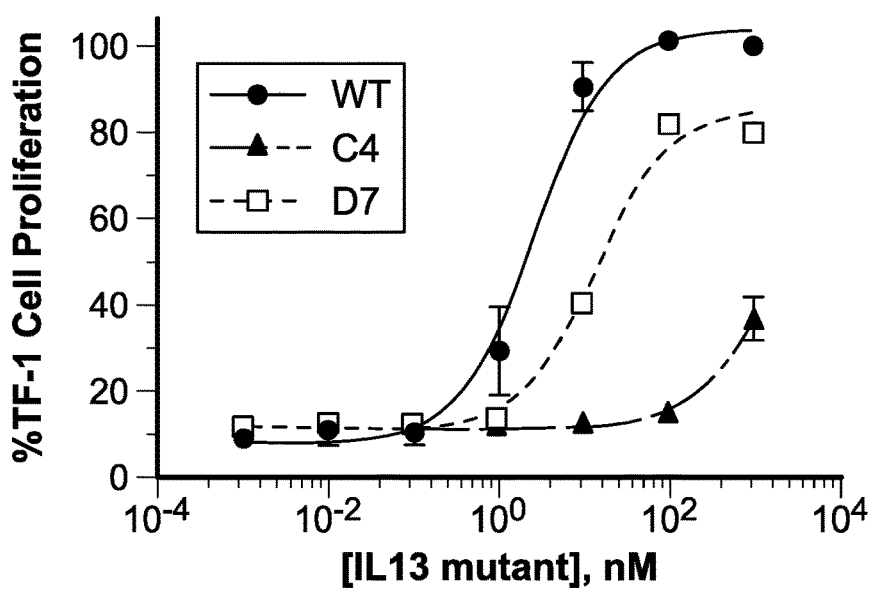

IL13 C4 and IL13 D7 are variants that have reduced affinity for IL13Rα1 relative to wild-type IL13 (WT) (Moraga, Richter et al. 2015). Because IL13Rα1 and IL13Rα2 share very similar binding interfaces on IL13 (FIG. 1A), IL13 C4 and IL13 D7 could exhibit a similar affinity decrease towards IL13Rα2. To assess receptor binding, WT, C4, and D7 were each displayed on the surface of yeast. Yeast were incubated with either recombinant IL13Rα1 or IL13Rα2 and binding was analyzed by flow cytometry (FIG. 1B). As expected, WT bound strongly to both IL13Rα1 and IL13Rα2. Both C4 and D7 showed IL13Rα2 binding comparably to WT, but no detectable binding to IL13Rα1 at the concentration tested. Surface plasmon resonance studies further confirmed these observations (FIG. 1C and FIG. 2A-F). WT, C4, and D7 all exhibit subnanomolar affinity for IL13Rα2 (0.001 nM, 0.393 nM, and 0.003 nM, respectively). However, the three variants strongly differ in binding affinity to IL13Rα1, confirming previous reporting (Moraga, Richter et al. 2015). These differences result in a several-log range of selectivity for IL13Rα2 relative to IL13Rα1, with WT, C4, and D7 exhibiting 440-fold, 92,000-fold, and 1,400,000-fold stronger affinity for IL13Rα2 relative to IL13Rα1. To further confirm this selectivity, IL 13 WT, IL13 C4, and IL13 D7 were tested in a variety of biological assays wherein activation through IL13Rα1 would yield functional outputs. First, soluble IL13 variants were titrated against IL13-responsive A549 cells for 15 minutes, and the phosphorylation of STAT6 was assessed by flow cytometry (FIG. 3A). Relative to WT, D7 and C4 both showed attenuated STAT6 phosphorylation, with the latter being more pronounced. Second, human fibroblasts were stimulated with IL13 variants for 8 hours, and upregulation of the CCL26 gene was assessed by qPCR (FIG. 3B). At both concentrations tested, WT induced strong upregulation of CCL26. D7 yielded an attenuated response, only inducing upregulation at the higher concentration of 1 µg/mL. C4 yielded essentially no response at both concentrations tested. Finally, IL13 variants were titrated against TF-1 for 96 hours, and cell proliferation was tracked (FIG. 3C). Relative to WT, treatment with D7 and C4 yielded attenuated proliferation, with the latter again being more pronounced.

Example 2: Variant IL13 CAR

Figure 4A:
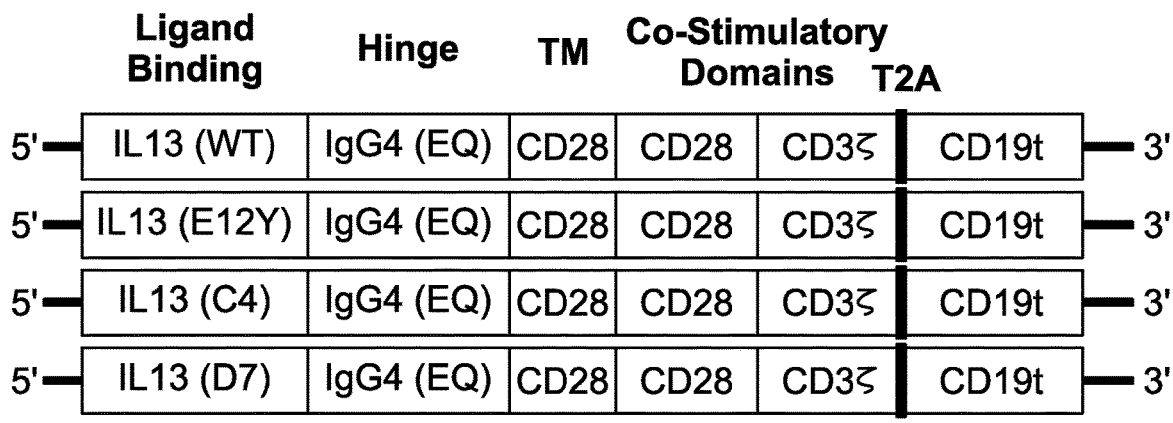
FIG. 4A-4C: IL13-variant CARs. (A) Schematic of IL13-CAR constructs containing wild-type (WT), E12Y, C4 or D7 binding domains. CARs also include an IgG4(EQ)-Fc linker, a CD28 transmembrane and cytoplasmic signaling domain, and CD3ζ. Constructs also contain a truncated CD19 (CD19t) separated from the CAR by a ribosomal T2A skip sequence. (B) Histograms showing anti-CD19 for cell transduction (left panel) and anti-Fc staining for CAR expression (right panel) for untransduced (Mock), IL13 WT, E12Y, C4 and D7 CARs by flow cytometry. Percent positive cells (and MFI) are denoted in each histogram. One representative experiment is shown. (C) Dose response binding affinity curves for the IL13 WT, E12Y and C4 and D7 CAR T cells to human IL13Rα2-Fc (left) or IL13Rα1-Fc (right). Data are presented as mean±standard deviation of three independent trials.
Figure 4B:
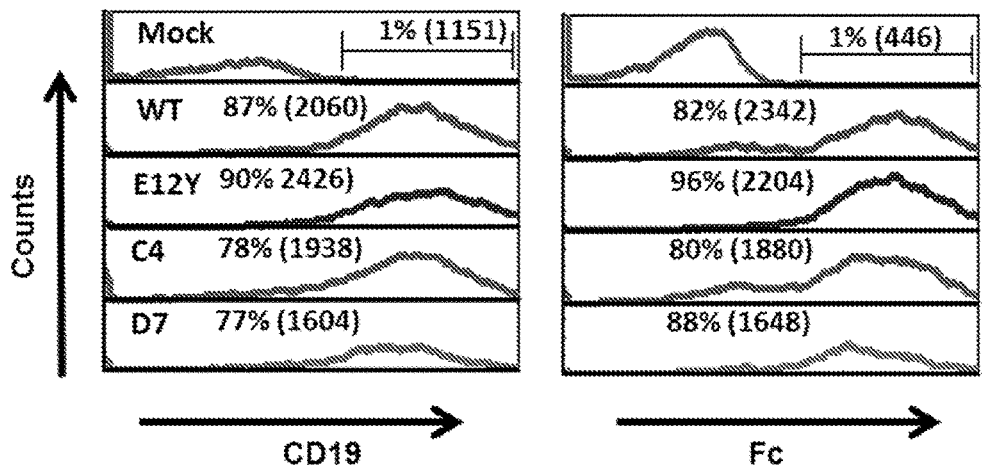

CAR that include C4 IL13, D7 IL13, E12Y IL13 or WT IL13 were generated. The four CAR were otherwise identical and included the CD28 co-stimulatory. The CAR included: a IgG4-Fc linker mutated at two sites within the CH2 region (L235E; N297Q) to reduce Fc receptor binding, a CD28 transmembrane domain, and the intracellular signaling domain of CD28 in series with CD3ζ (FIG. 4A). Our group and others have observed that IL13-based CARs with CD28-based costimulation (vs 4-1BB costimulation) have more sensitive recognition of IL13Rα1 expression (Brombacher, Nono et al. 2017). Therefore, in order to better differentiate IL13Rα2 specificity, we used CD28 costimulation as part of the CAR backbone. In addition, CAR cassettes have a T2A ribosome skip sequence followed by a truncated CD19 used as a marker of lentiviral transduction efficiency, cell tracking, and enrichment. Flow cytometry analysis of CD19t for cell transduction and IgG4-Fc for CAR detection confirm comparable expression for the four IL13-CAR variants (FIG. 4B). For all in vitro and in vivo studies, IL13-CARs were engineered in naïve/memory T cells (Tn/mem). Tn/mem are enriched CD62L+naïve and memory T cells, including both the central memory (Tcm) and stem cell memory (Tscm) populations, along with naïve T cells (Tn).

Figure 4C:
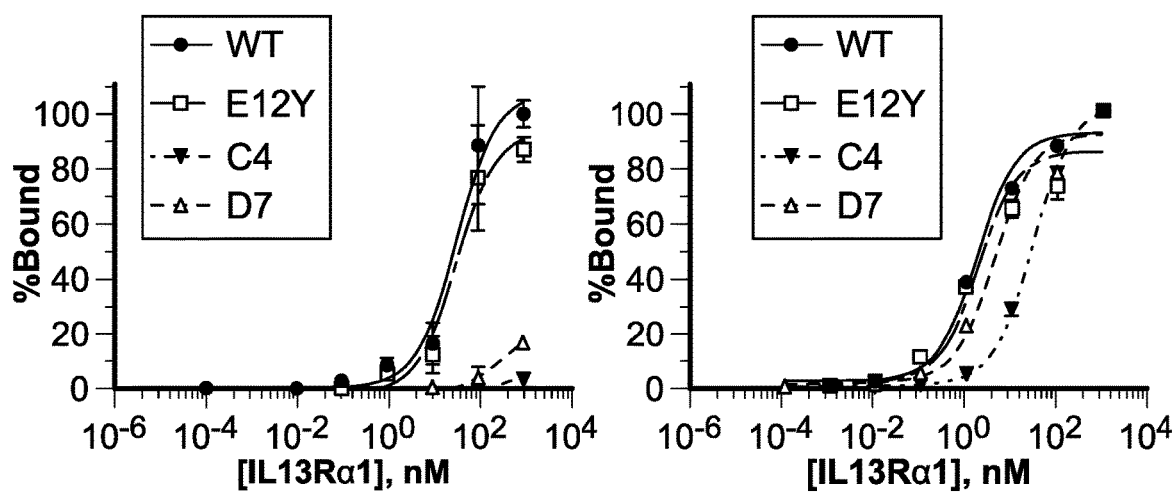

To assess target specificity of the IL13-CART cells, we evaluated their binding affinities to recombinant human IL13Rα2 and IL-13Rα1 in dose-response curves (FIG. 4C). T cells stably expressing the indicated IL13-based constructs were titrated with biotinylated IL13Rα1 or IL13Rα2 for 1 hr at 4° C. The level of receptor bound to IL13 was measured by incubating the cells with streptavidin coupled to Alexa Fluor-647. E12Y and D7 CAR T cells bind to IL13Rα2 with similar affinity to WT, i.e., 1.8 nM (95% CI: 1.0-3.7 nM), 4.2 nM (95% CI: 2.8-6.3 nM) and 1.7 nM (95% CI: 1.2-2.4 nM) respectively, whereas C4 displayed a weaker affinity, 29 nM (95% CI: 23-36) (FIG. 4C, right panel). Notably, the affinities of IL13-derived CARs for IL13Rα2 are two to three orders of magnitude weaker than those of the free proteins. By contrast, D7 and C4 CAR T cells exhibited minimal binding to IL13Rα1 on the assayed concentration range, whereas WT and E12Y had nearly identical affinity (34 nM; 95% CI: 21-54 nM for both variants) (FIG. 4C, left panel).

Figure 5A:
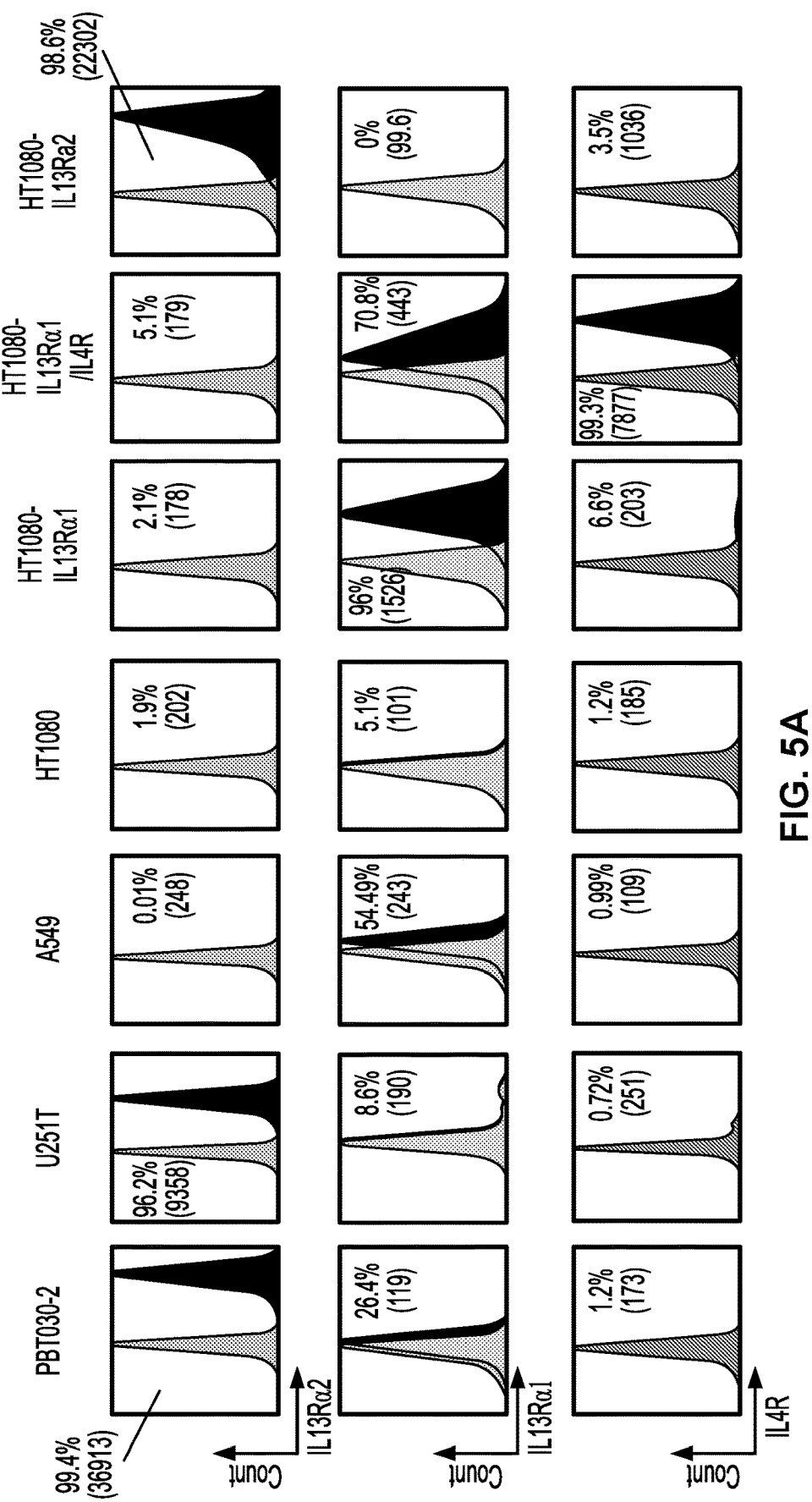
FIG. 5A-5C: Detection of IL-13Rα2, IL-13Rα1 and IL-4R on cancer cell lines. (A) Flow cytometry histograms showing either IL-13Rα2, IL-13Rα1 or IL-4R expression in the following adherent human cancer cell lines: (1) PBT030-2, (2) U251T, (3) A549, (4) HT1080P, (5) HT1080-IL13Rα1, (6) HT1080-IL13Rα1/IL4R, and (7) HT1080-IL13Rα2. The cancer cell lines were enzymatically dissociated into single cells and immediately stained with antigen markers (IL13Rα2, IL13R a 1, IL4R) at 4° C. in the dark for 30 mins. Cells were then assessed by flow and the antigen expressions of viable tumors were displayed as histograms. Values located within each histogram represent the % expression with the mean fluorescence intensity (MFI) in parentheses. (B) Western blot showing the protein expression of IL13Rα2 and IL13Rα1, with (3-actin as a loading control. (C) qPCR analysis showing the mRNA expression of IL13Rα2, IL13Rα1, IL4R and codon optimized IL13Rα2. For both the western blot and qPCR, protein or mRNA lysates were isolated, respectively, from the previously mentioned cancer cell lines. All data shown are means+/−sem.
Figure 5B:
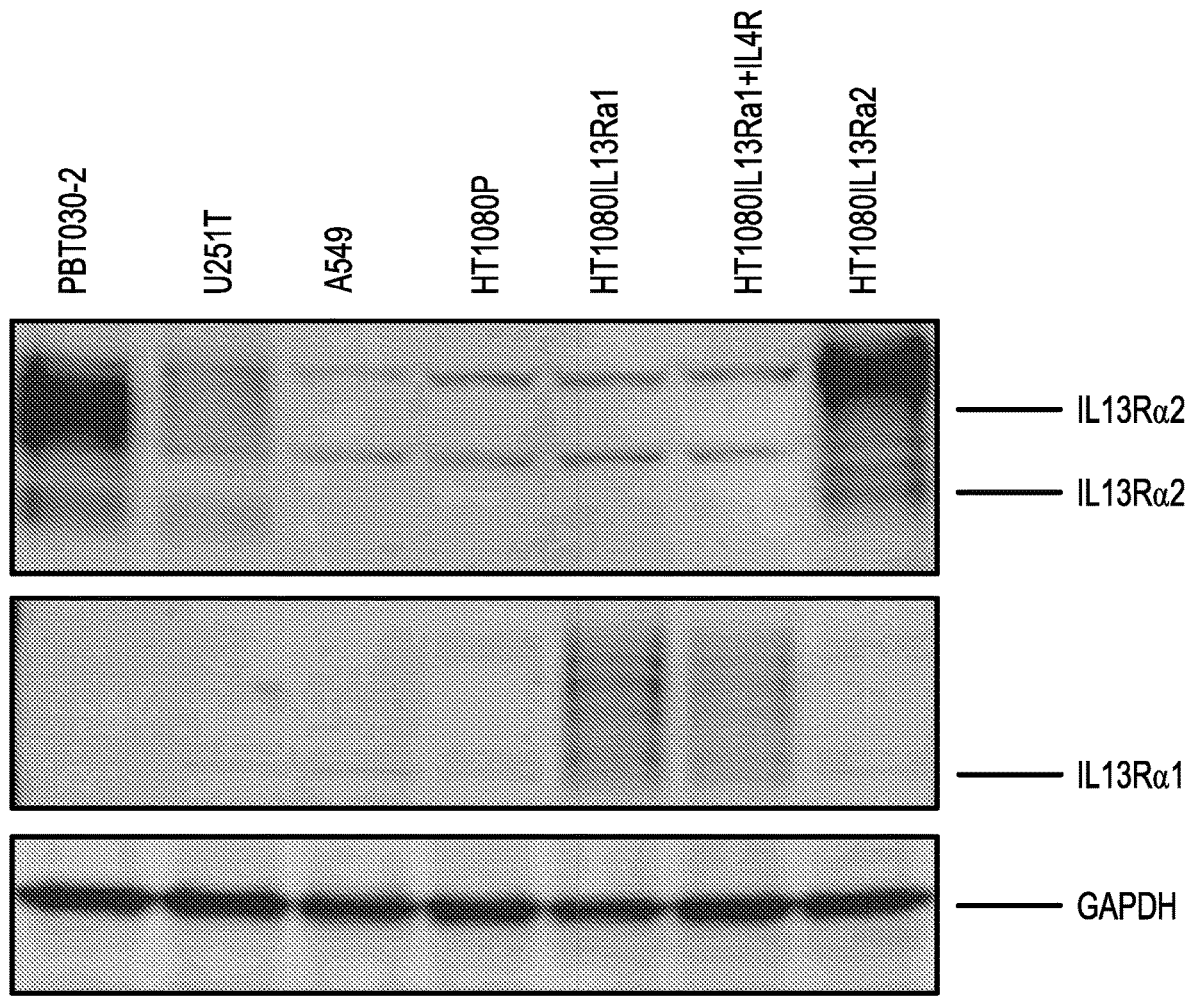
Figure 5C:
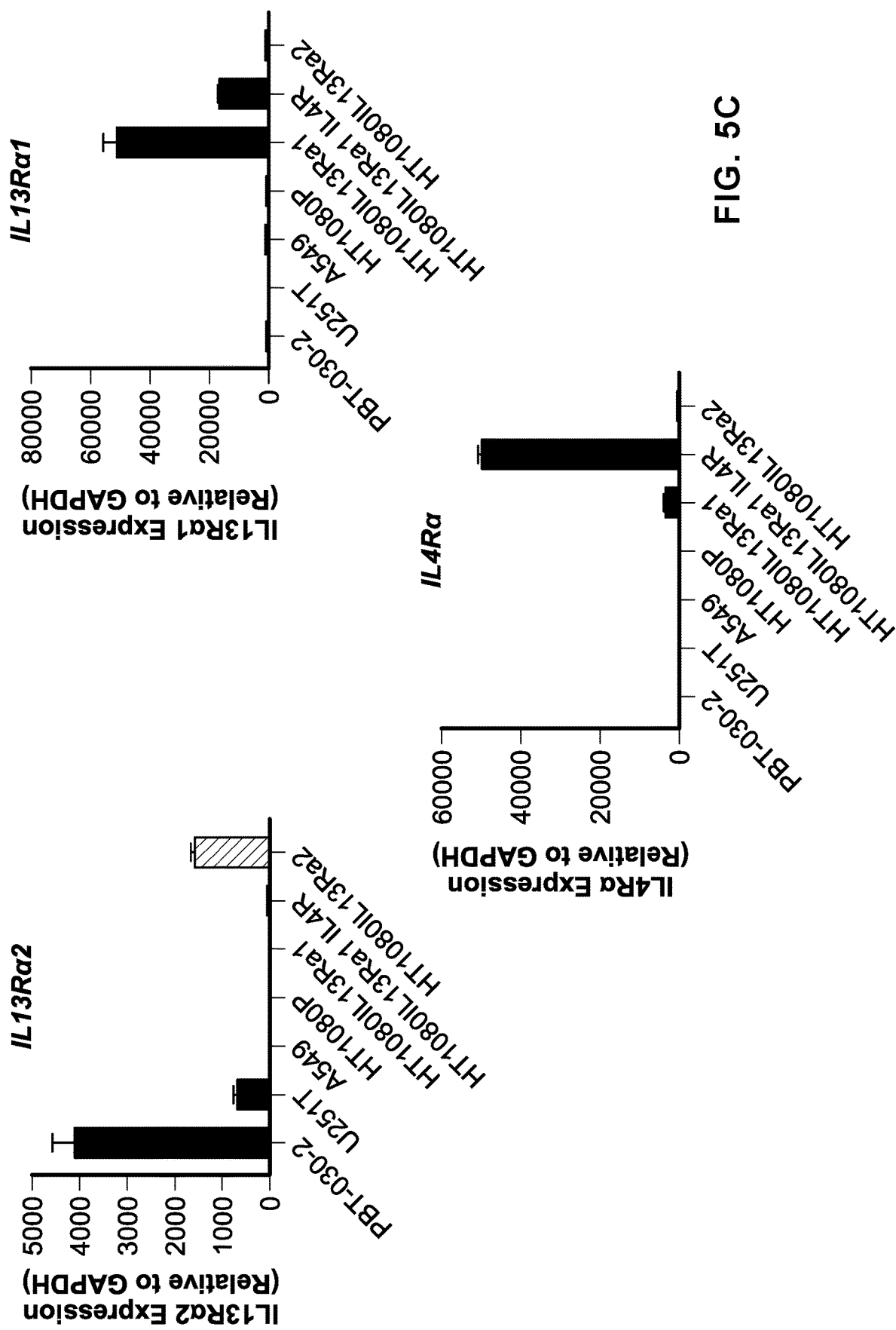
Figure 6A:
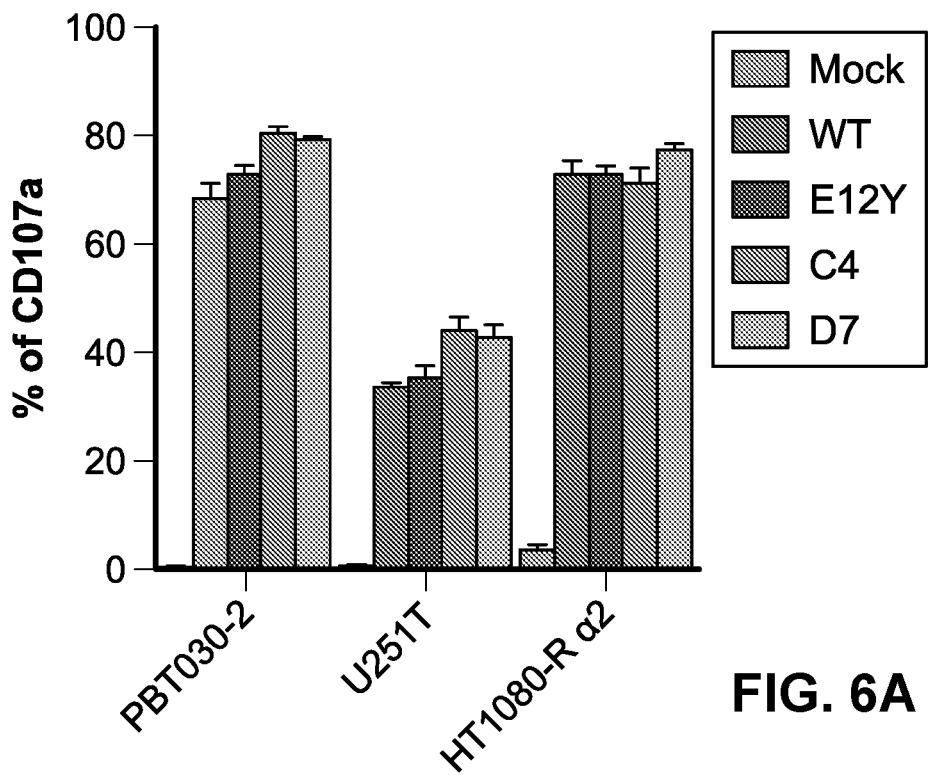
FIG. 6A-6F: IL13 WT, E12Y, C4, and D7 CARs mediate comparable IL13Rα2-dependent in vitro effector function. IL13Rα2-dependent degranulation (A) and IFN-γ production (B) for IL13 WT, E12Y, C4, and D7 CAR and untransduced (Mock) T cells. T cell lines were co-cultured at a 1:1 effector to target (E:T) ratio with IL13Rα2+ glioblastoma lines U251T and PBT030-2 or HT1080 engineered to express IL13Rα2 (HT1080-IL13Rα2); after 5 hrs the degranulation marker CD107a and intracellular IFN-γ was measured by flow cytometry and percent positive cells graphed (mean±SD; n=3 wells). (C) Secreted IFN-γ production by indicated T cell lines in response to increasing concentrations of immobilized recombinant human IL13Rα2-Fc (mean±SD; n=3 wells). p<0.0001 for all CAR T cell IL13-variants and mock T cells. (D) Tumor killing by IL13-CAR and mock T cell lines cultured at a 1:10 E:T ratio for 2 days. Flow cytometry was used to determine the remaining viable tumor count and tumor killing was determined as a % normalized to mock (mean±SD; n=3 wells). (E) CAR T cell killing in experiments using four separate donors at 1:50 E:T against PBT030-2, U251T and HT1080IL-13Rα2 showing similar levels of tumor killing for WT, E12Y, C4, and D7. Plots represent remaining tumor cells at day 7 (Dotted line represents seeded tumor cells). (F) Live CAR T cells in experiments presented following 7-day co-culture presented in (E). No live CAR T cells were observed in Tumor only and Mock CAR T cell experiments; levels of CAR T cell persistence were as follows: WT>D7>E12Y>C4 (Dotted line represents seeded CAR T cells). Panels of A-F are representative of at least three independent experiments. All data shown from A-F are means+/−sem. (** p<0.0001, * p<0.005, ** p<0.01, * p<0.05).
Figure 6B:
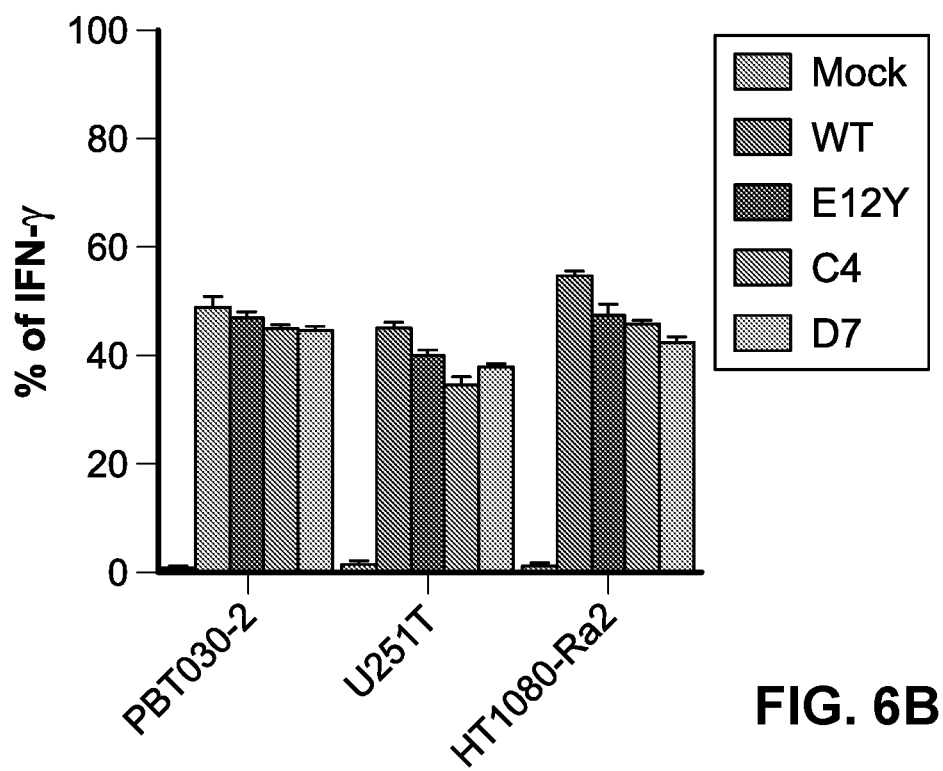
Figure 6C:
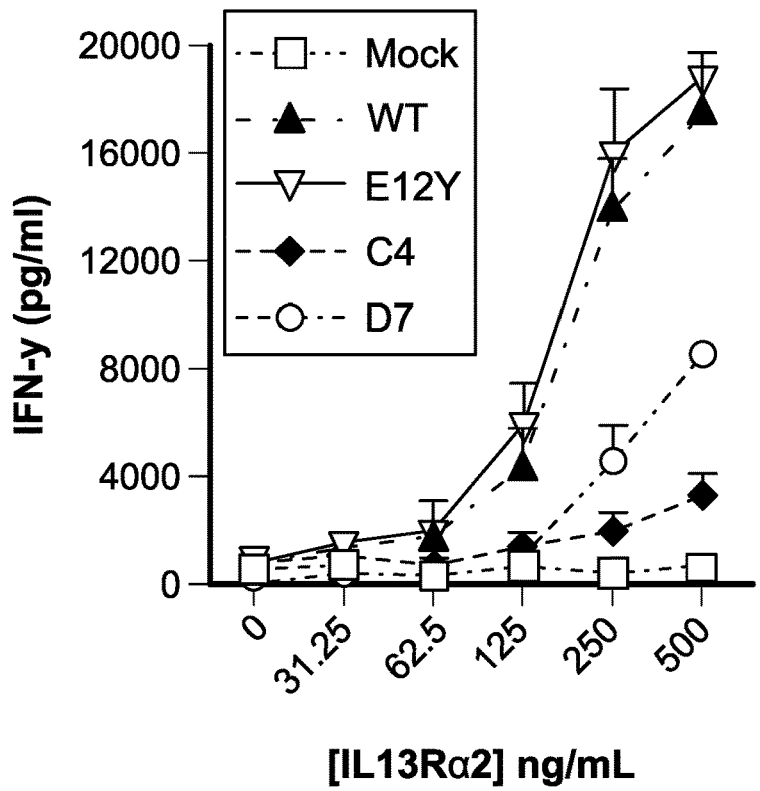

Example 3: Functional Characterization of C4 and D7 IL13 Variant CAR T Cells in IL13Rα2 Targeting We assessed IL13Rα2-targeting abilities of the IL13 wild type and variant CAR T cells by examining antigen-specific T cell activation. For these functional studies we used three IL13Rα2-expressing human cancer cell lines. The patient-derived primary glioblastoma tumor line PBT030-2 and human glioma line U251T endogenously express IL13Rα2 at high levels, consistent with its overexpression in pathological conditions (FIG. 5A-5C). The IL13 receptor family negative human fibrosarcoma cell line HT1080 was engineered to overexpress IL13Rα2 (HT1080-IL13Rα2). IL13Rα2 expression on the cell lines was confirmed by flow cytometry, western blot and qPCR (FIG. 5A-5C). Using CD107a as a marker of degranulation, we evaluated CAR T cell effector function after co-culturing the cells with the three IL13Rα2-expressing cell lines at a 1:1 effector to target (E:T) ratio for five hours. WT, E12Y, D7, and C4 CAR T cells had comparable CD107a expression against all the IL13Rα2-expressing cell lines, measured as percent positive cells, with negligible CD107a expression seen in mock (untransduced) T cells (FIG. 6A). As another measure of T cell activity, we evaluated cytokine production, both intracellular IFN-γ production by flow cytometry (FIG. 6B) and secreted IFN-γ in response to increasing concentrations of immobilized recombinant human IL13Rα2-Fc (FIG. 6C). The percentage of cells positive for intracellular IFN-γ after a 5-hour incubation at E:T 1:1 with the IL13Rα2-expressing cell lines was similar across WT, E12Y, D7, and C4 CAR T cells, with mock T cells producing negligible IFN-γ. The levels of secreted IFN-γ as a function of IL13Rα2 concentration varied across the CAR T cell types, with WT and E12Y CAR T cells secreting the highest IFN-γ concentration, followed by D7, and then C4 CAR T cells.

Figure 6D:
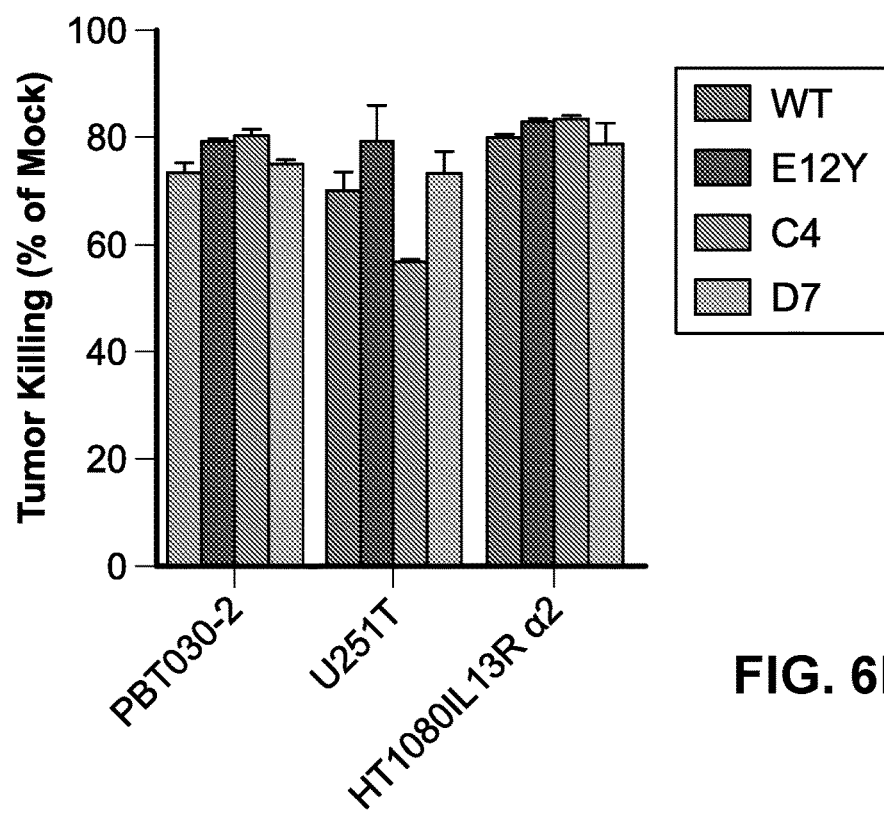
Figure 6E:
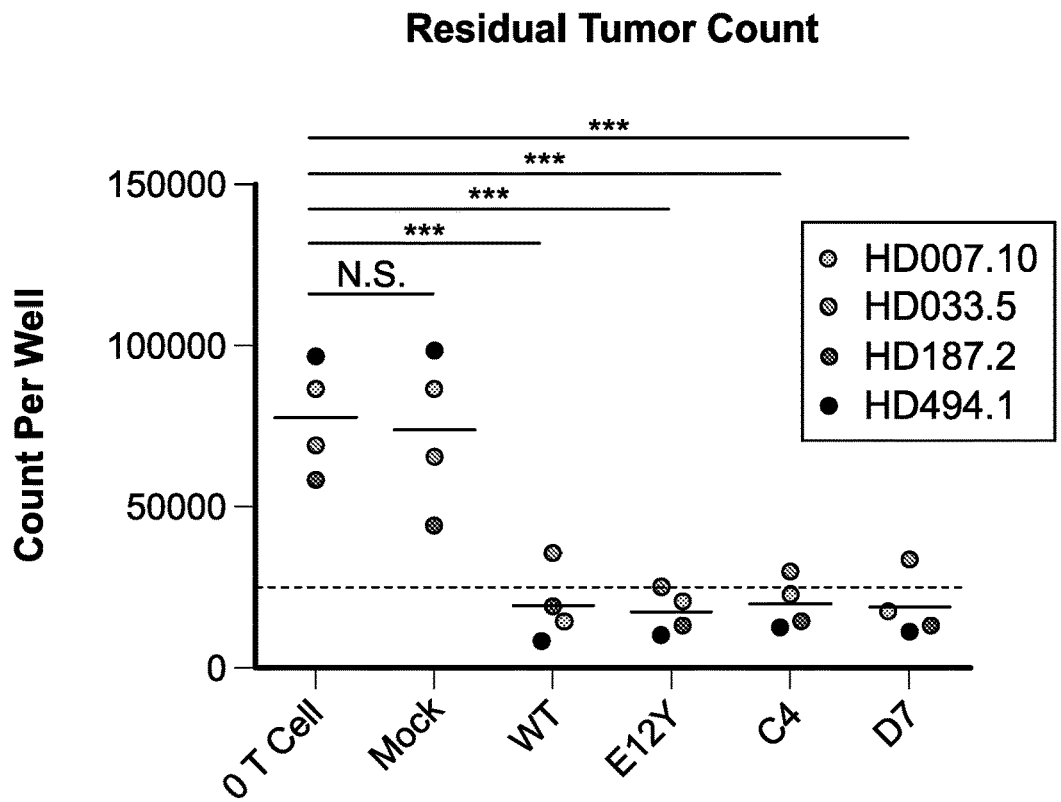
Figure 6F:
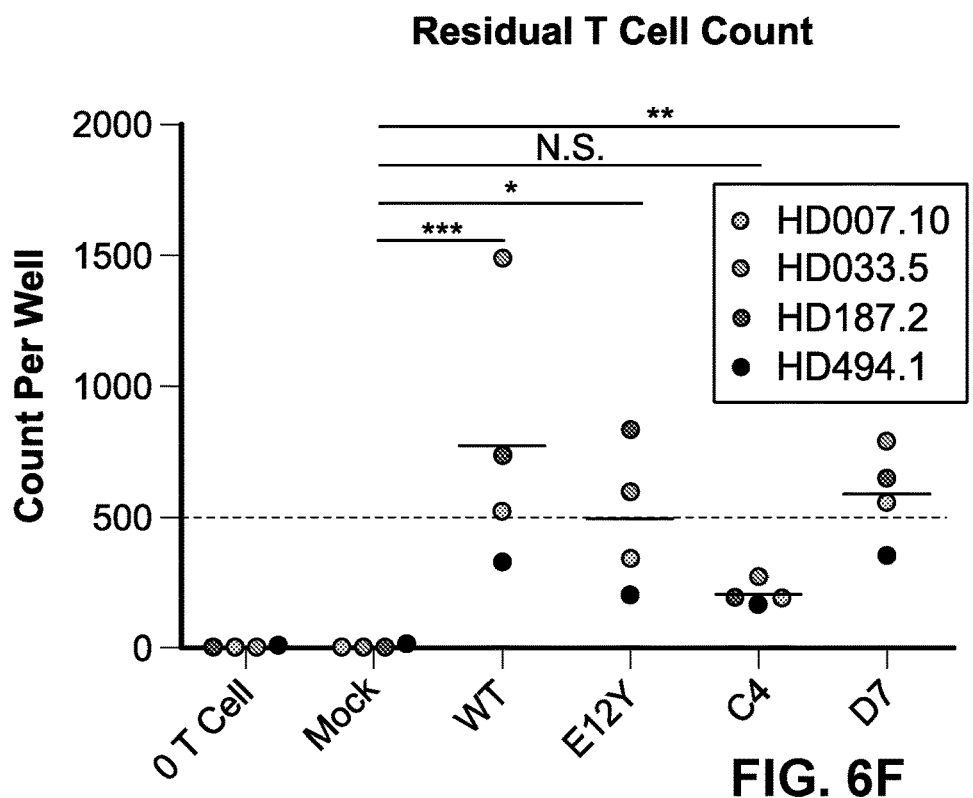

To further investigate functional differences between IL13 wild type and variant CAR T cells, we performed in vitro tumor killing assays. CAR T cells were co-cultured with tumor targets PBT030-2, U251T, and HT1080-IL13Rα2 at E:T 1:10 for two days, and viable remaining tumor cells were counted by flow cytometry with results expressed as percentage normalized to the tumor cell count after incubation with mock T cells. All of the CART cells (WT, E12Y, D7, and C4) killed the tumor cells with similar efficiency (FIG. 6D). The functional characteristics of the CAR T cells were consistent across four distinct healthy donors within each experiment. In an extended long-term killing assay, CAR T cells co-cultured at E:T 1:50 with PBT030-2 had similar cytolytic activity regardless of IL13 variant and across four donors (FIG. 6E). Importantly, cytotoxicity observed using IL13 mutein CARs was significantly higher than mock and no T cell controls (p<0.005 in all cases). From the same experiments, analysis of live CAR T cells after seven days of co-culture showed persistence/proliferation in the wild type and variant CAR T cells, compared with the no T cell and mock controls, in which no live T cells were observed (FIG. 6F). Of note, C4 displayed lower levels of CART cell persistence/expansion as compared to the other IL13 CARs, suggesting reduced potential for antigen-dependent proliferation.

Figure 7A:
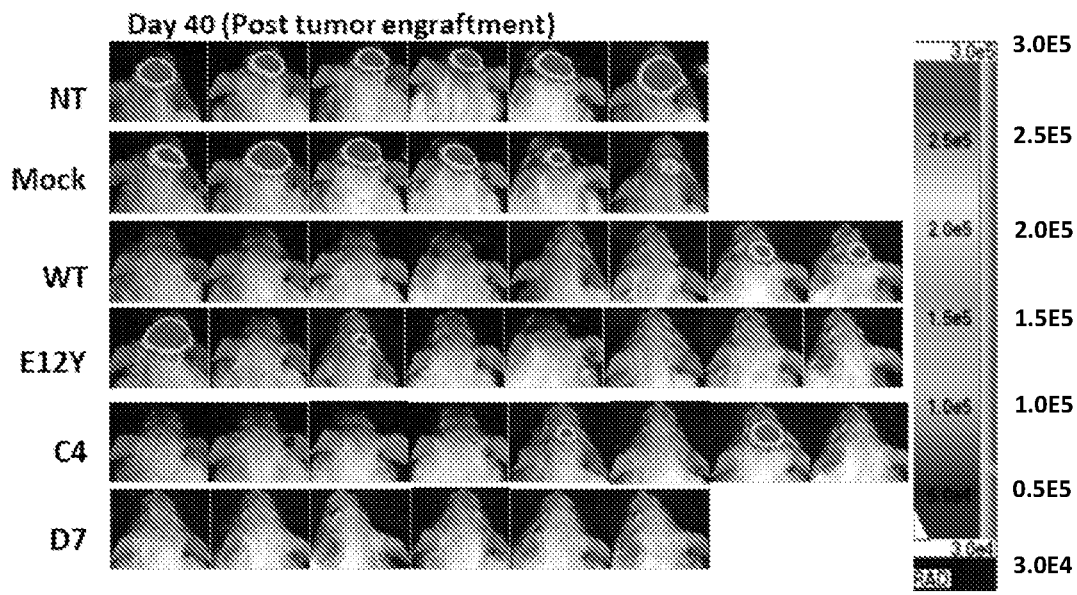
FIG. 7A-7C: IL13-E12Y, -C4 and -D7 mutein CARs exhibit similar levels of therapeutic efficacy in vivo against a human glioma xenografts. In vivo efficacy is similar across WT and mutein CARs against a human glioma xenografts. (A) NSG mice stereotactically implanted into the right forebrain with 0.1×105 EGFP-ffLuc+ PBT030-2 tumorspheres. On day 8 mice received either no treatment, 0.3× $10^6$ injection of Mock Tn/mem (no CAR) T cells or a 0.3×$10^6$ injection of the following CAR positive Tn/mem cells: IL13 WT, IL13ζ28 (E12Y), IL13ζ28 (C4), IL13ζ28 (D7). (n=6-8) [Two of the mice in group D7 died early during treatment.] Representative flux images are shown on day 150 post engraftment. (B) Kaplan-Meier survival curves (summary data for three experiments) demonstrate comparable survival at day 150 (dotted line represents day 9+/−1 day) for mice treated with the IL13-CAR variants, with IL13-WT, -E13Y, -C4 and -D7 CAR T cells all improving survival as compared to Mock T cells (p<0.0001 Mantle-Cox log rank test (n=14-18). (C) Bar graph summarizing data from three separate experiments indicating the number of tumor free, tumor relapse and euthanized untreated mice, and mice treated with the IL13-CAR variants, with IL13-WT, -E13Y, -C4 and -D7 CART cells at day 150 post tumor implantation FIG. 8A-8F: IL13-E12Y, -C4 and -D7 mutein CARs exhibit similar levels of therapeutic efficacy in vivo against a human glioma model. (A-C) Quantification of ffLuc+ flux (photons/sec show C4 and D7 IL-13 mutein CART cells have comparable potency to the WT and E12Y single mutant IL13-CARs. Dotted lines represent the flux values of individual mice while the colored solid line represent the average flux of that treatment cohort. Data are represent three independent experiments (n=6-8). (D-F) Kaplan-Meier survival curves for the corresponding adjacent flux values of the individual demonstrating comparable survival and tumor relapse rate for mice treated with the IL13-CAR variants, with IL13-WT, -E13Y, -C4 and -D7 CART cells all improving survival as compared to Mock T cell treated and untreated mice (p≤0.0001 Mantle-Cox log rank test (n=6-8).
Figure 7B:
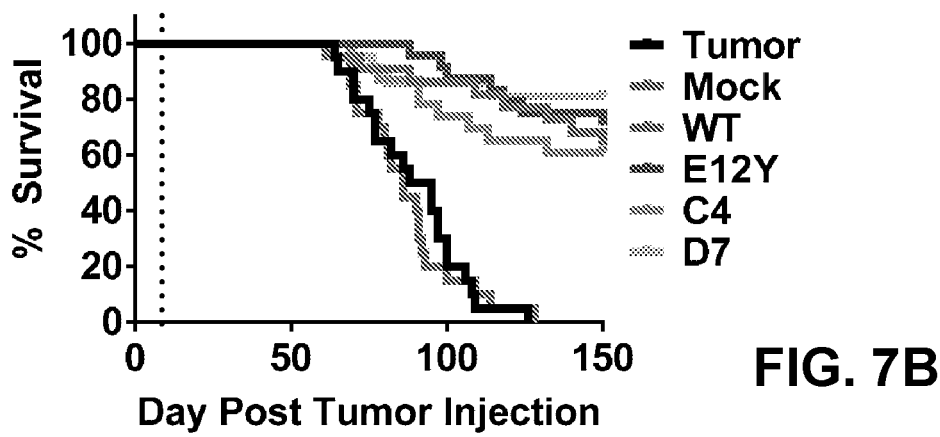
Figure 7C:
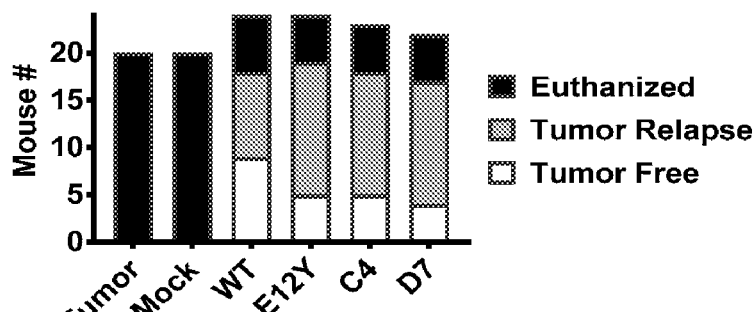
Figure 8A:
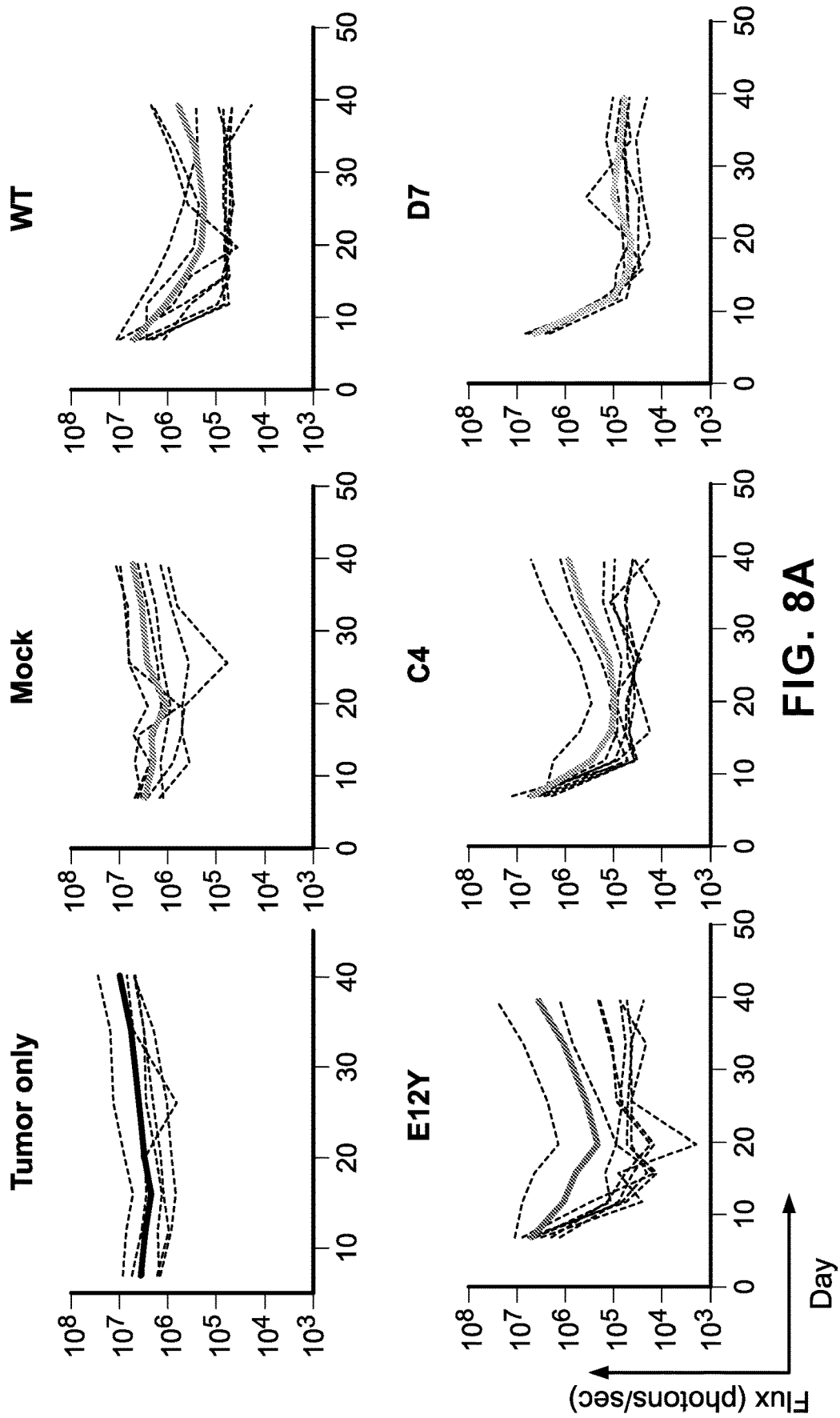
Figure 8B:
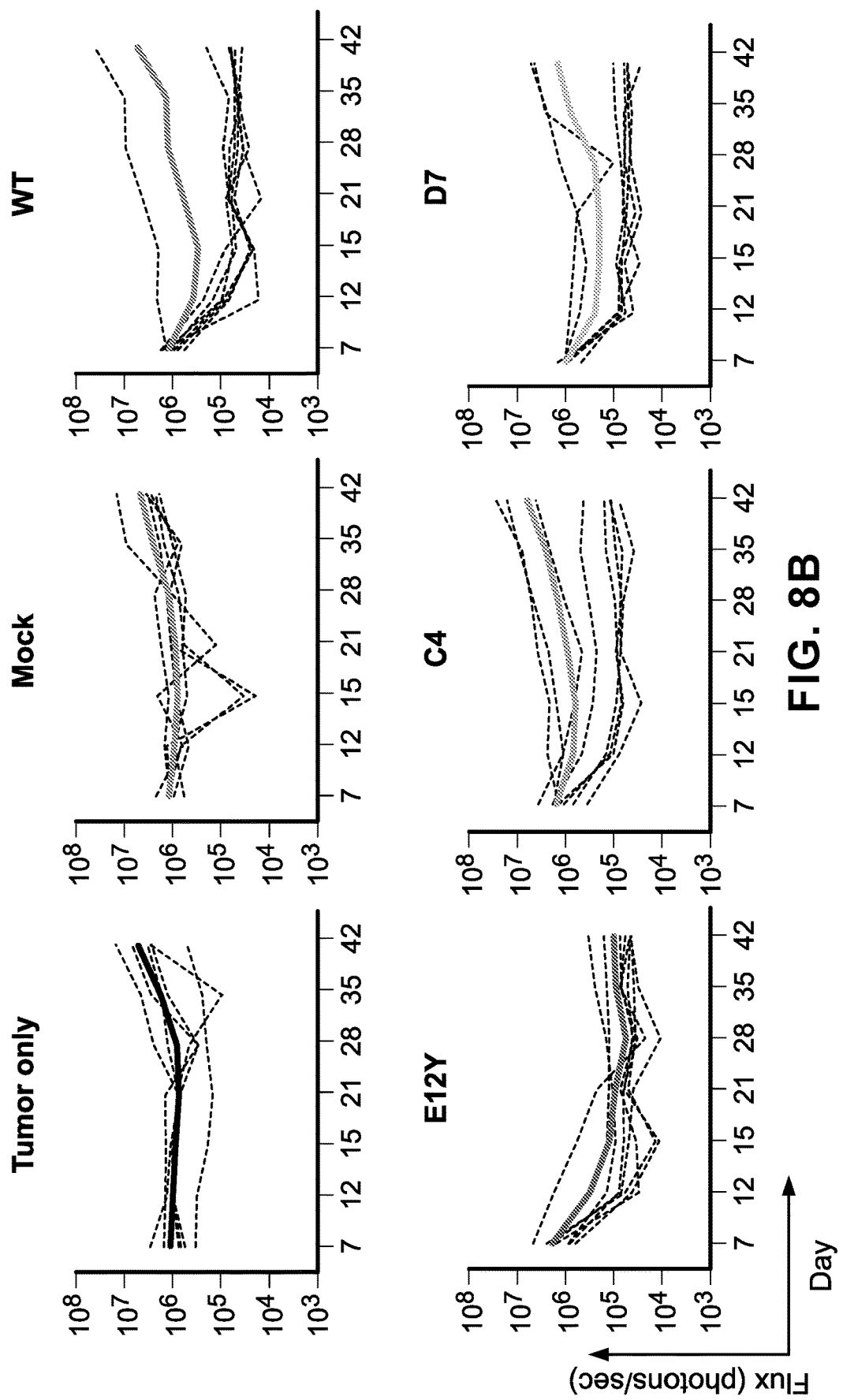
Figure 8C:
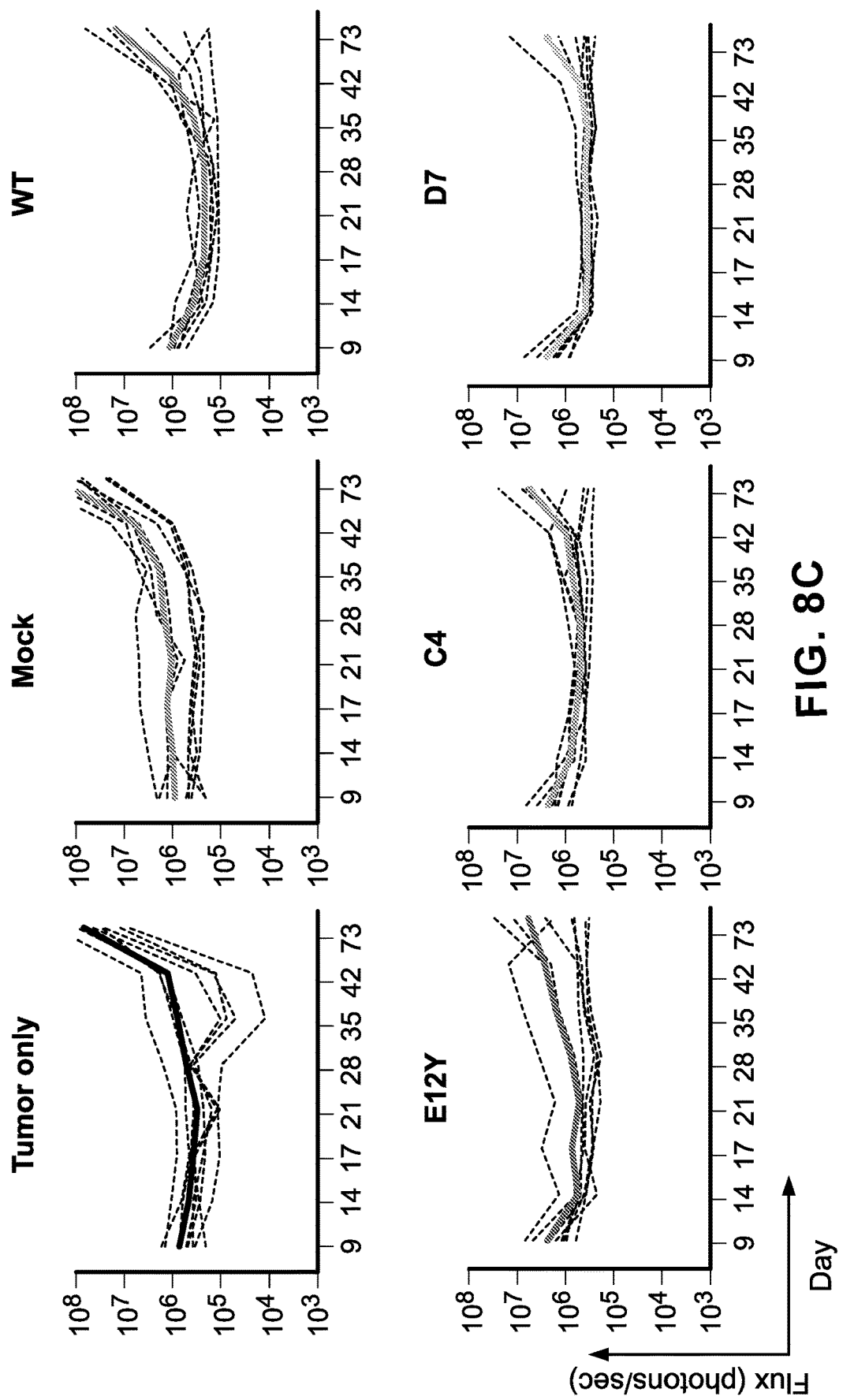
Figure 8D:
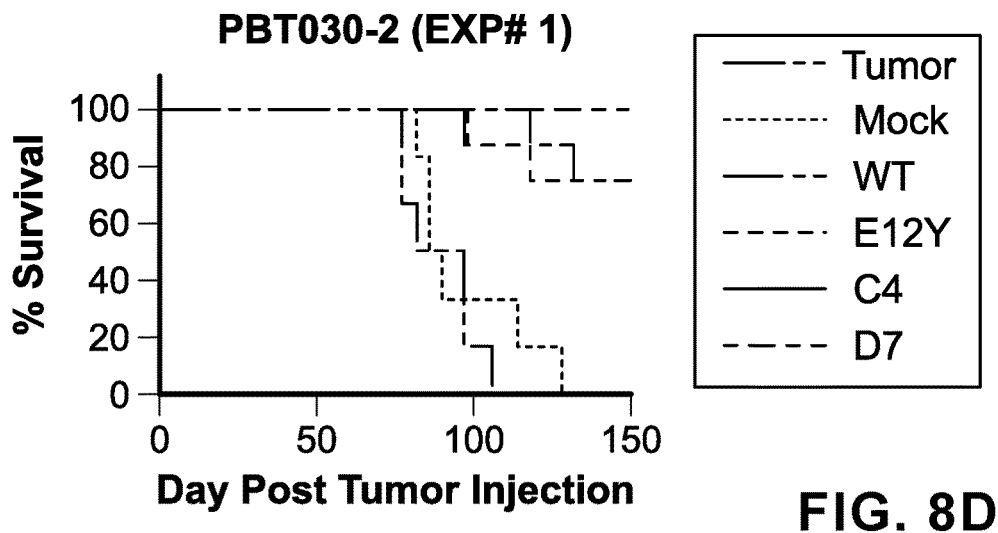
Figure 8E:
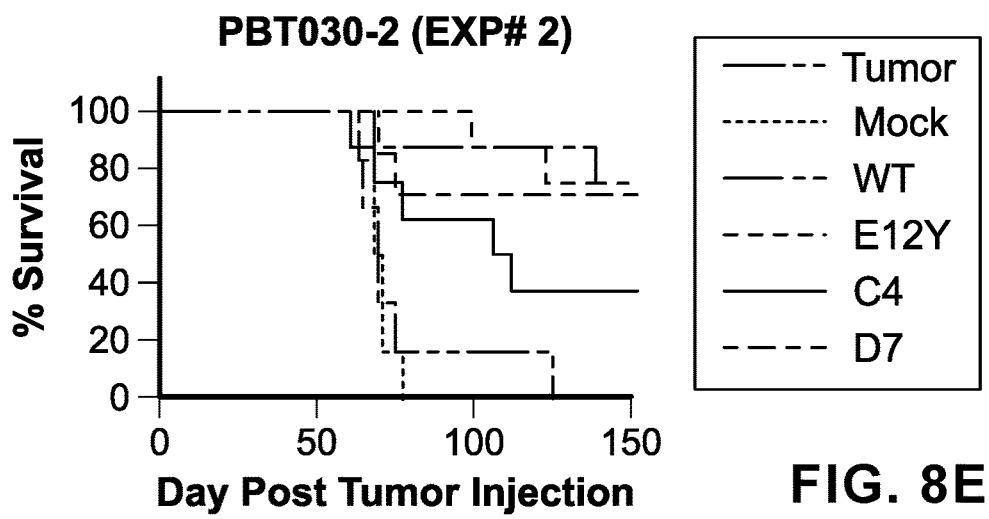
Figure 8F:
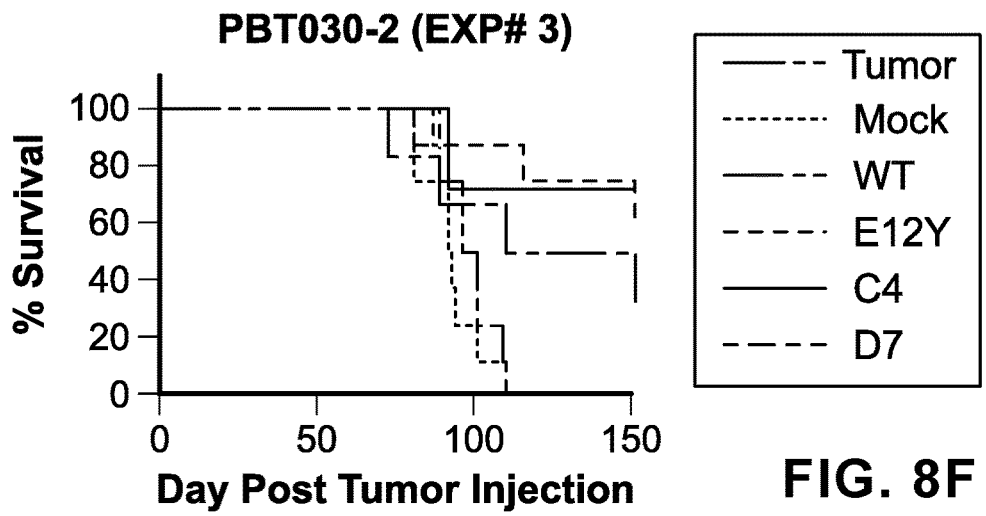

Example 5: Patient-derived IL13Rα2+ Xenograft Mouse Models Demonstrate Improved Survival after Treatment with IL13 Variant CAR T Cells We evaluated the in vivo anti-tumor efficacy of the CAR T cells in our previously established xenograft brain tumor model with IL13Rα2 PBT030-2 cells engineered to express the firefly luciferase (ffluc) reporter gene (Brown, Starr et al. 2012). In three independent experiments, tumor-bearing NSG mice ($1 \times 10^6$ tumor cells injected intracranially; $9 \pm 1$ days engraftment) that received intratumoral (i.t.) injection of $0.3 \times 10^6$ mock (untransduced) T cells exhibited tumor growth and survival similar to non-treated controls, whereas treatment with WT, E12Y, C4, and D7 CAR T cells efficiently reduced tumor burden (FIG. 7A). Kaplan-Meier survival analysis demonstrates improved survival for mice treated with IL13 wild type and variant CART cells (FIG. 7B and FIG. 8), and by day 150 the mice treated IL13 wild type and variant CAR T cells had similar numbers of tumor-free and tumor relapsed mice (FIG. 7C). Taken together, these results demonstrate that C4 and D7 CAR T cells exhibit similar in vivo anti-tumor activity for IL-13Rα2 expressing tumors compared with WT and E12Y CAR T cell treatment.

Figure 9A:
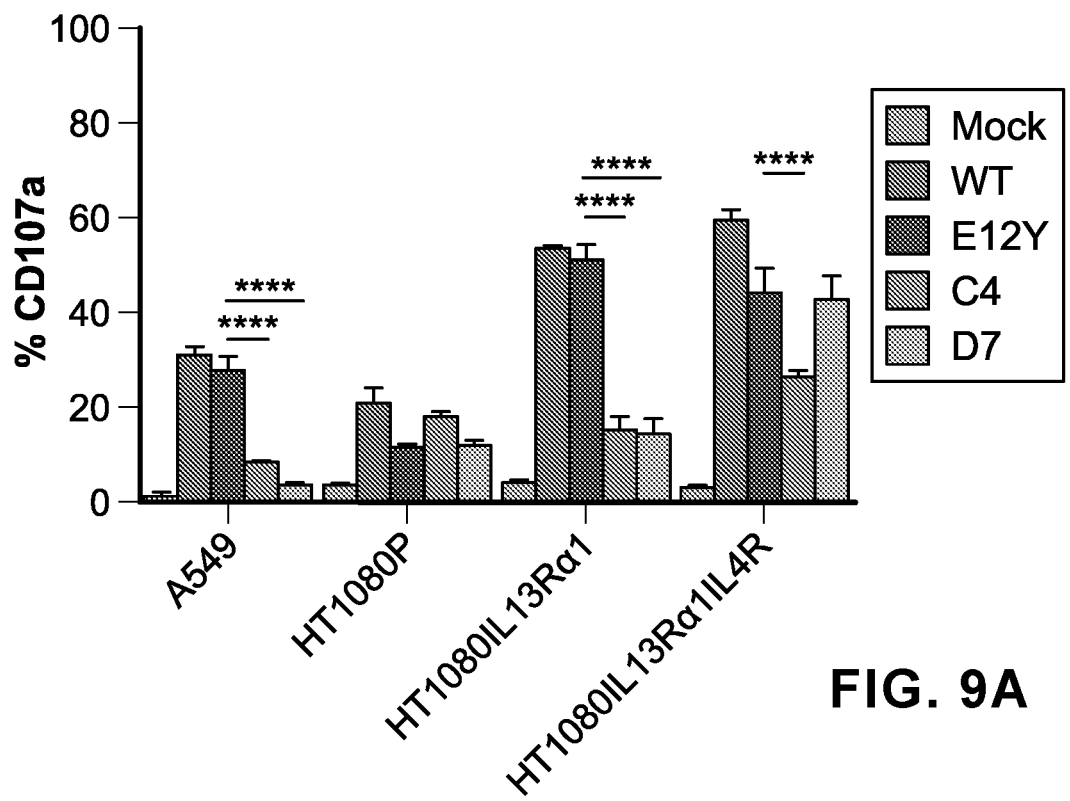
FIG. 9A-9F: IL13 C4 and D7 mutein CAR T Cells showed reduced recognition of IL13Rα1. IL13Rα1-dependent degranulation (A) and IFN-γ production (B) for IL13 WT, E12Y, C4 and D7 CART cells co-cultured with IL13Rα1+A549, HT1080 parental, and HT1080 engineered to express either IL13Rα1 or both IL13Rα1 and IL4R as described in FIG. 7. (C) Secreted IFN-γ production by indicated T cell lines in response to increasing concentrations of immobilized recombinant human IL13Rα1-Fc (mean±SD; n=3 wells). (D) IL13Rα1-dependent cell killing of the indicated CAR and target lines at a 1:10 E:T ratio for 2 days. (A)-(D) are representative of at least three independent experiments. (E) Winn assay evaluating A549 (0.1× $10^6$) tumor engraftment after co-culture with CAR and mock T cell lines (E:T ratio 10:1; 2 hr pre-incubation and engraftment on day 0; n=4). (F) NSG mice xenotransplated with 0.5×$10^6$ HT1080 IL13Rα1/IL4R in 1:1 ratio of media to matrigel, followed by treatment with either no T Cells, or 5×$10^6$ mock T cells or the various mutein CART cells on day 4. All data shown on A-F are means+/−sem. (** p<0.0001, * p<0.005, ** p<0.01, * p<0.05).
Figure 9B:
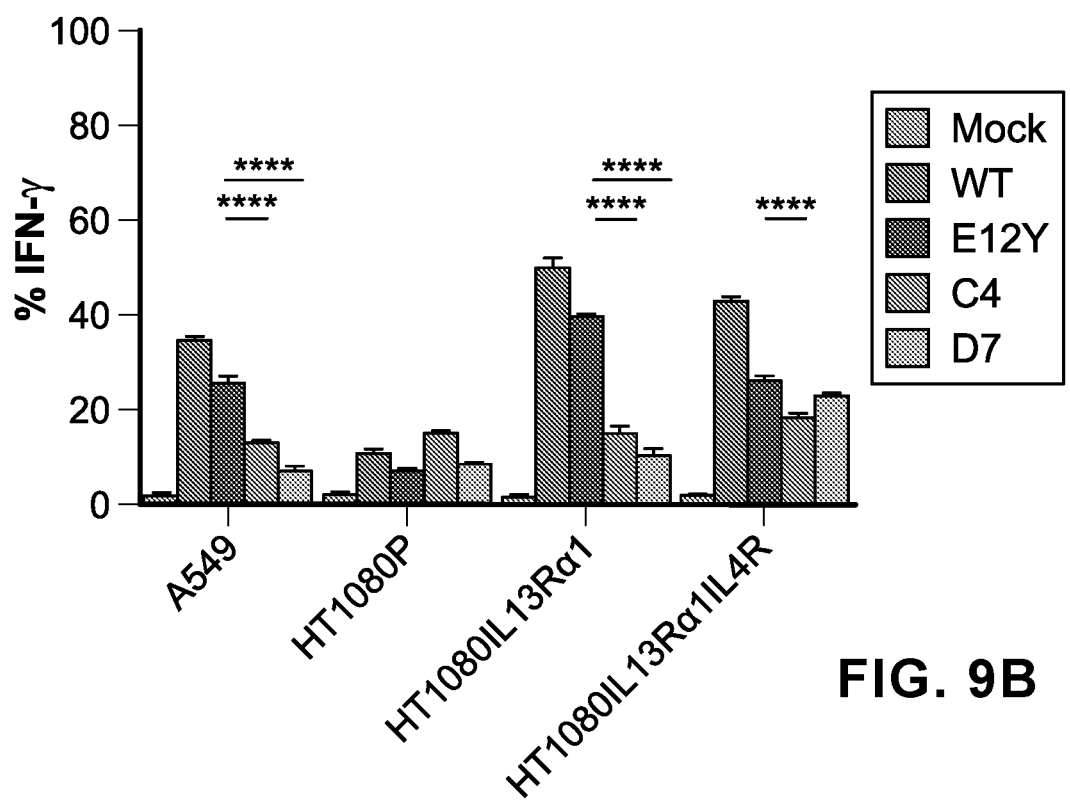
Figure 9C:
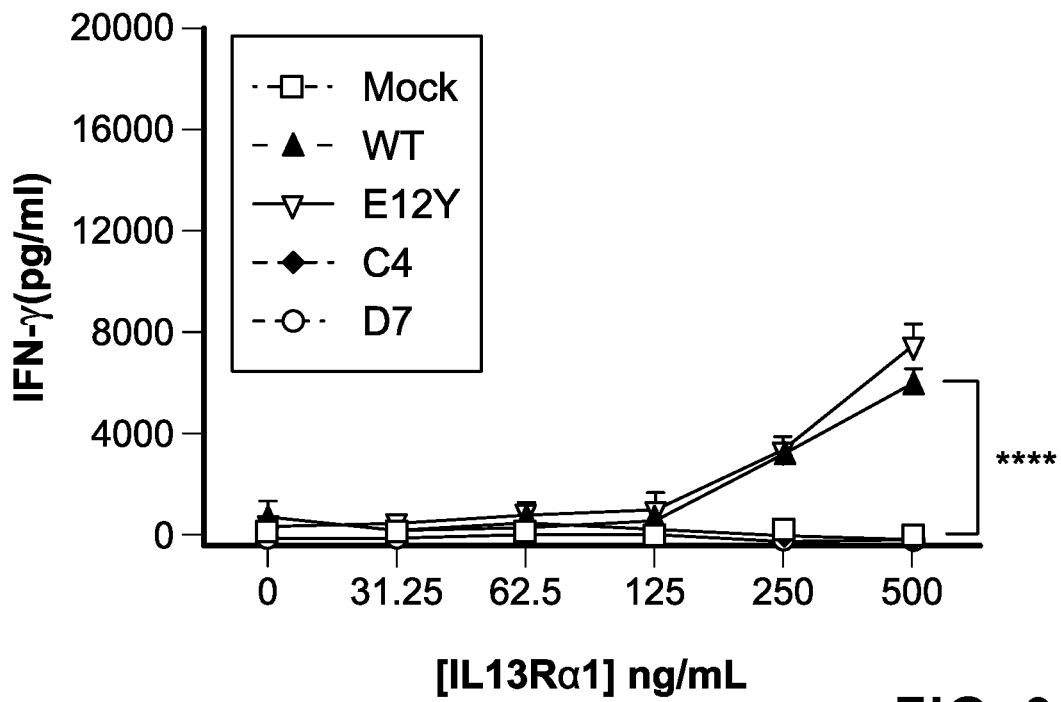
Figure 9D:
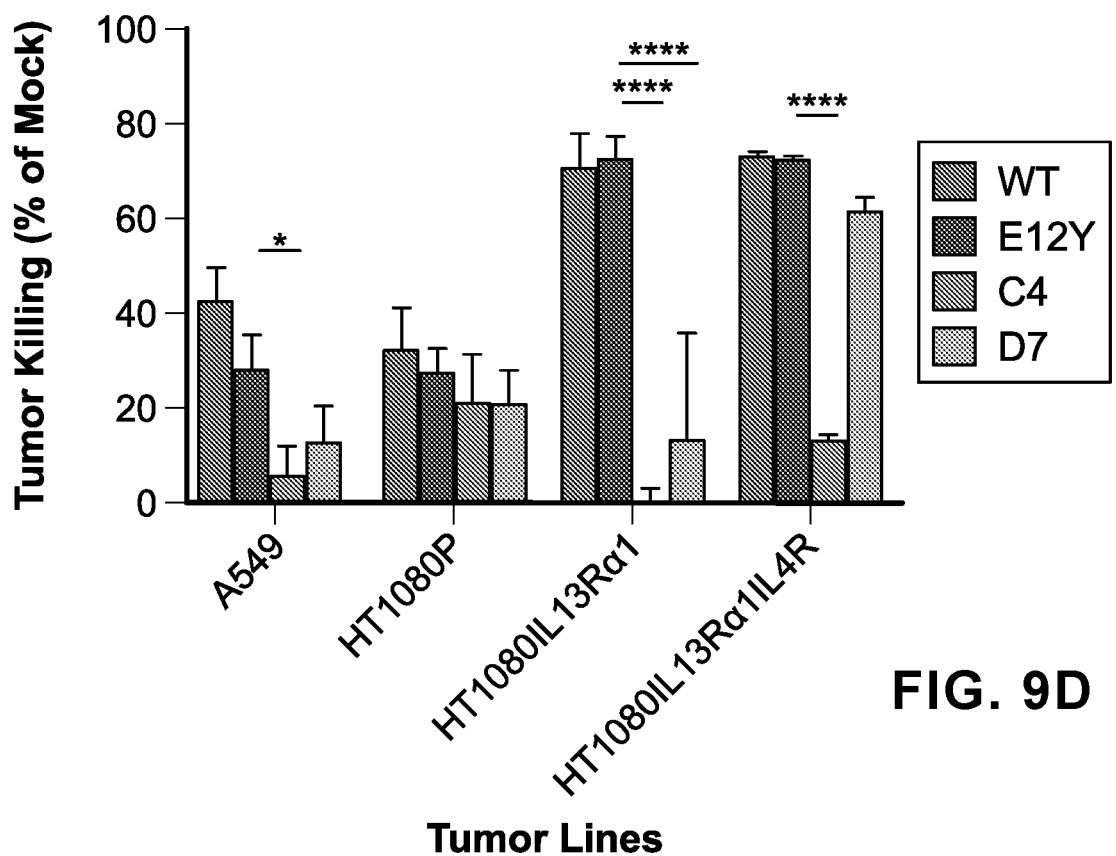

Example 6: IL13 Variant CAR T Cells Display Diminished Effector Activity Against IL13Rα1-Expressing Tumors Several human cancer cell lines with varying expression of IL13Rα1 were used to evaluate relative effector activity of IL13 wild type and variant CART cells. Human lung adenocarcinoma cell line A549 endogenously expresses moderate levels of IL13Rα1 with no detectable IL13Rα2 or IL4Rα. Human fibrosarcoma cell line HT1080, which does not express IL13Rα1, IL13Rα2, or IL4Rα, was engineered to overexpress either IL13Rα1 (denoted HT1080-IL13Rα1) or both IL13Rα1 and IL4Rα (denoted HT1080-IL13Rα1-IL4Rα) (FIG. 5A-5C). In 5 hour co-culture of CART cells with IL13Rα1-expressing tumor cells (A549 and HT1080-IL13Rα1) at 1:1 E:T, WT and E12Y induced significantly more surface expression of CD107a (FIG. 9A) and intracellular expression of IFN-γ (FIG. 9B) than C4 and D7 ($p<0.05$ for all comparisons). In contrast, when CART cells were co-cultured with HT1080-IL13Rα1-IL4Rα, E12Y and D7 showed similar expression of surface CD107a and intracellular IFN-γ, whereas C4 displayed attenuated response relative to E12Y in both assays ($p<0.05$ for both). Notably, against HT1080-IL13Rα1-IL4Rα cells, all the mutein CAR T cells (E12Y, C4, and D7) had a significantly lower frequency of IFN-γ producing cells compared with WT CART cells. Evaluation of secreted IFN-γ after culture with plate-bound IL13Rα1 revealed distinct differences in T cell activity among the CAR variants. WT and E12Y both secreted significantly higher IFN-γ levels compared with C4 and D7, which had nearly undetectable IFN-γ (FIG. 9C). The results of long-term killing assays against IL13Rα1-expressing cancer cell lines mirrored those of the degranulation and cytokine production assays: C4 and D7 CAR T cells showed diminished killing relative to WT and E12Y (FIG. 9D). Against HT1080-IL13Rα1-IL4Rα, D7 killed comparably to E12Y and WT whereas C4 showed significantly less tumor killing ($p<0.05$ for all comparisons).

Figure 9E:
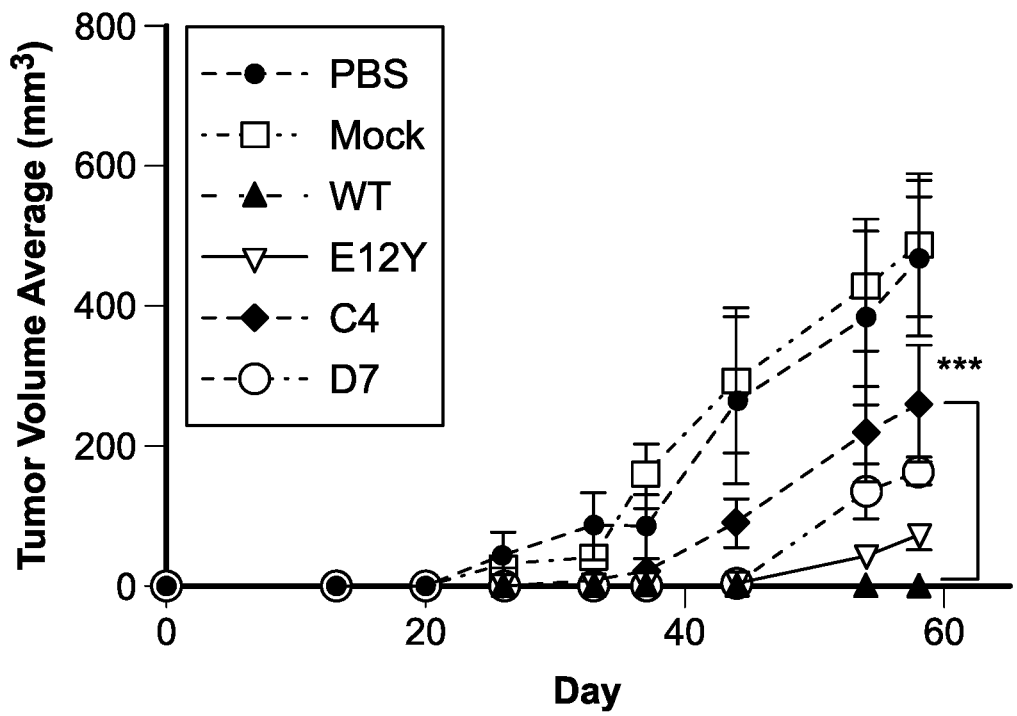

To interrogate the selectivity of the C4 and D7 mutein CAR T cells in vivo, we investigated the anti-tumor activity of the CAR T cells in xenograft models using IL13Rα1-expressing tumor cells. In order to detect small differences in CAR T cell activity with greater sensitivity, we used the Winn assay to directly evaluate effector activity by incubating tumor and T cells together for two hours prior to injection (Winn 1960, Winn 1961). We co-cultured $1 \times 10^6$ WT, E12Y, C4 and D7 CAR T cells with $0.1 \times 10^6$ A549 cells for 2 hours followed by engraftment of the co-cultured cells into NSG mice (FIG. 9E). Following tumor growth kinetics over 60 days, the WT CART cells ablated engraftment of IL13Rα1-expressing tumors. All CAR T cell variants displayed some delay in engraftment relative to PBS and mock T cell treated tumors. At later time points, C4 CAR T cells displayed significantly less growth inhibition than WT and E12Y ($p<0.05$ for all comparisons on days 54 and 58).

Figure 9F:
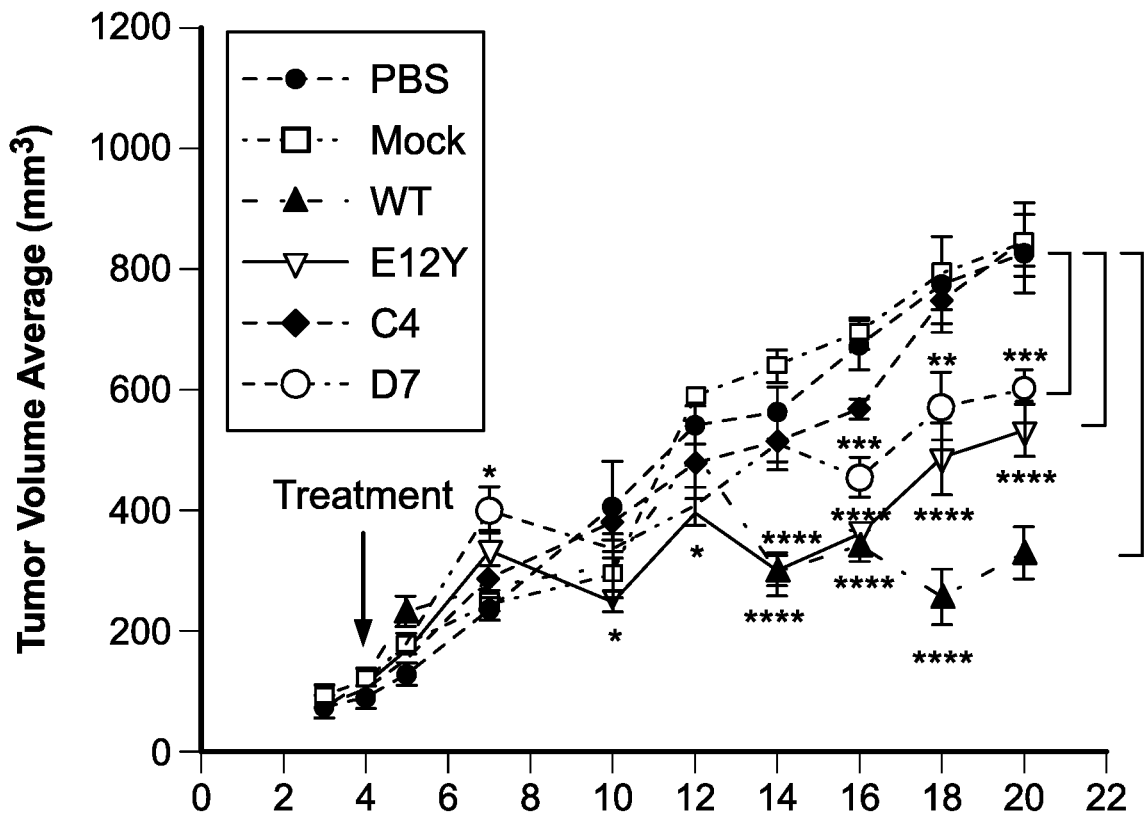
Figure 14:
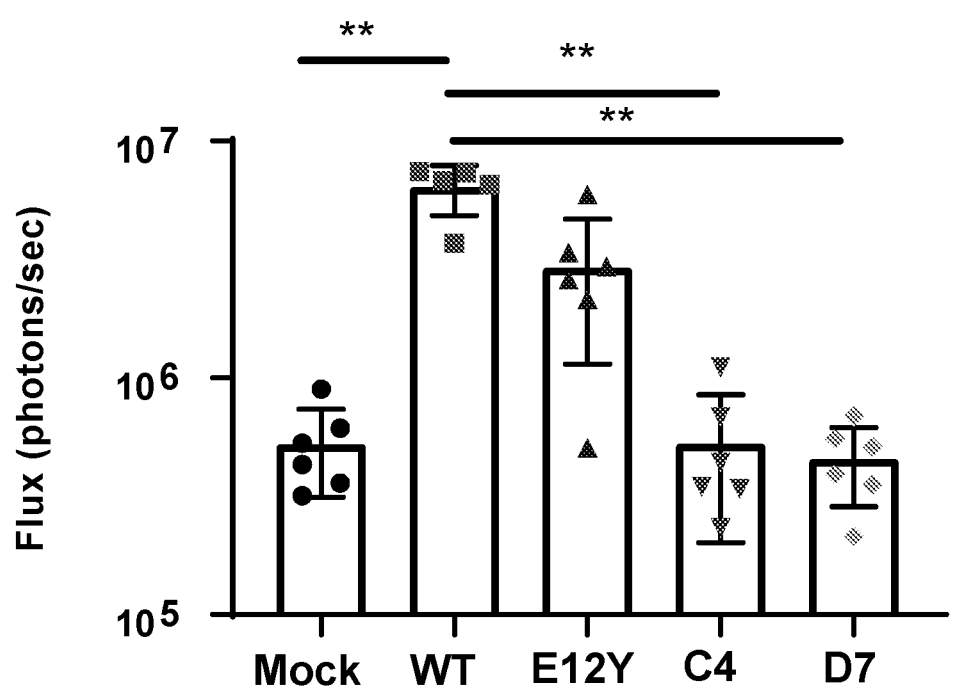
FIG. 14: D7 and C4 mutein CAR traffic away from lung. CAR were administered to mice and presence in the lungs was assessed by luminescence on Day 8

To evaluate the CAR T cell variants against tumors expressing the high affinity pair IL13Rα1/IL4Rα, NSG mice were xenotransplanted subcutaneously with $0.5 \times 10^6$ HT1080-IL13Rα1-IL4Rα with 4-day engraftment. The mice were treated with mock, WT, E12Y, C4, and D7 CAR T cells, or PBS by intratumoral injection (FIG. 9F). Again, the C4 CAR T cells had the least amount of antitumor activity, with tumor growth comparable to PBS treated and mock T cell treated mice (FIG. 9F). Similar to the in vitro killing assays, D7 and E12Y CAR T cell treatment showed comparable decreased antitumor activity relative to WT CAR T cells ($p<0.05$ for all comparisons Day 16 and thereafter).

Methods Used in Examples

Tumor Lines

PBT030-2 is a patient derived primary glioblastoma tumor sphere line which was heterotopically passaged twice in NOD/Scid IL2RγCnull (NSG) mice (Brown, Starr et al. 2012). (Brown, Starr et al. 2012). Established human tumor lines A549 (lung carcinoma), and HT1080 (fibrosarcoma) were obtained from the American Tissue Culture Collection (ATCC) and maintained in DMEM (Gibco, Grand Island, NY) supplemented with 10% FBS, 2 mM L-glutamine, and 25 mM HEPES. HT-1080 was modified lentivirally to express IL13Rα1, both IL13Rα1 and IL4Rα, or IL13Rα2. U251T glioma line was a gift from Dr. Waldemar Debinski and grown as previously described (Brown, Warden et al. 2013). Cell line TF-1 (erythroleukemia) was grown in RPMI containing 10% FBS, penicillin-streptomycin, 2 mM L-glutamine and GM-CSF to promote proliferation and survival. All cell lines were maintained at 37° C. with 5% CO2.

Flow Cytometry

Intracellular phospho-STAT6 staining was performed with pSTAT6-Alexa488 (BD Biosciences, 1:50) after ice-cold methanol (100% v/v) permeabilization. The induction of STAT6 phosphorylation was calculated by subtracting the Mean Fluorescence Intensity (MFI) of the stimulated samples from that of the unstimulated sample. The normalized values were plotted against cytokine concentration to yield dose-response curves from which the EC50 values were calculated based on nonlinear least squares regression fit to a sigmoidal curve.

CAR expression was assessed using biotinylated anti-Fc (Jackson ImmunoResearch, West Gove, PA1:100) antibody followed by streptavidin-PE (BD Bioscience, San Jose, CA, 1:20) and by staining for the truncated CD19 extracellular sequence with CD19-PE-Cy7 (BD Bioscience, cl, SJ25Cl, 1:100). Target lines were characterized by staining with IL13Rα2-PE (Biolegend, cl. SHM38, 1:100), IL13Rα1 (Biolegend, cl. SS12B, 1:100), and IL-4Rα-PE (BD Pharmingen, cl. hIL4R-M57, 1:20). In other assays, additional antibodies were used as specified: CD107a-FITC (BD Biosciences, cl. H4A3, 1:9), CD45 PerCP (BD Biosciences, cl. 2D1, 1:20), CD3-VioBlue (Milentyi Biotec, Inc, 1:20), CD8 APC-Cy7 (BD Biosciences, cl. SK1, 1:50), and IFNγ-APC (BD Biosciences, cl. B27, 1:100). Cells were For staining, cells were washed and re-suspended in FACS Stain Solution (HBSS, 20% v/v FBS, 0.1% w/v NaN3), incubated with antibodies for 30 min at 4° C., followed by secondary stain if necessary, then washed and run on the MACSQuant (Miltenyi Biotec, Bergisch Gladbach, Germany) Flow data was analyzed with FBS Express 4 (De Novo Software, Los Angeles, CA).

Protein Expression and Purification

Human IL-13 and the IL-13 variants were cloned into the pAcGP67-A vector (BD Biosciences) in frame with an N-terminal gp67 signal sequence and a C-terminal hexahistidine tag and produced using the baculovirus expression system, as described in (LaPorte, Juo et al. 2008). Baculovirus stocks were prepared by transfection and amplification in *Spodoptera frugiperda* (Sf9) cells grown in SF900II media (Invitrogen) and protein expression was carried out in suspension Trichoplusiani (High Five) cells grown in InsectXpress media (Lonza). Following expression, proteins were captured from High Five supernatants after 48 h by nickel-NTA agarose (Qiagen) affinity chromatography, concentrated, and purified by size exclusion chromatography on a Superdex 200 column (GE Healthcare), equilibrated in 10 mM HEPES (pH 7.2) containing 150 mM NaCl. Recombinant cytokines were purified to greater than 98% homogeneity. For biotinylated receptor expression, IL-13Rα1/IL-13Rα2 ectodomains were cloned into the pAcGP67-A vector with a C-terminal biotin acceptor peptide (BAP)-LNDIFEAQKIEWHW followed by a hexahistidine tag. Receptors were coexpressed with BirA ligase in the presence of excess biotin (10 µM). Protein concentrations were quantified by UV spectroscopy at 280 nm using a Nanodrop2000 spectrometer (Thermo Scientific).

Yeast Display of IL-13

General yeast display methodologies are modified from previously described protocols (Boder and Wittrup 1997). Human IL-13 cDNA was cloned into the yeast display vector pCT302. *S. cerevisiae* strain EBY100 was transformed with the pCT302_IL-4 vector and grown for two days at 30° C. on SDCAA plates. Individual colonies of IL-13-displaying yeast were grown overnight at 30° C. in SDCAA liquid media (pH 4.5), followed by induction in SGCAA media (pH 4.5) for 2 days at 20° C. Yeast were stained with biotinylated IL-13Rα1 or IL-13Rα2 followed by incubation with streptavidin couple to Alexa-647 dye. Fluorescence was analyzed on an Accuri C6 flow cytometer.

Surface Plasmon Resonance

SPR experiments were conducted on a Biacore T100 instrument using a Biacore SA sensor chip (GE Healthcare). Biotinylated IL-13Rα1/IL-13Rα2 was captured at a low density (50-100 response units (RU)) and kinetics measurements were conducted at 30 µL/min. An unrelated biotinylated protein was immobilized as a reference surface for the SA sensor chip with matching RU to the experimental surface. All measurements were made using 3-fold serial dilutions of IL-13 agonists in the running buffer (1×HBS-P, 0.1% BSA). The IL-13Rα1/IL-13Rα2 bound to the chip surface was regenerated with 7 mM glycine (pH 3.0) and 250 mM NaCl. Kinetic parameters were determined using 120 s to 190 s of IL-13 agonist association time and 20 s to 1200 s dissociation time. All data fitting was performed using the Biacore T100 evaluation software version 2.0 with a 1:1 Langmuir binding model.

TF-1 Cell Proliferation Assays

Two thousand TF-1 cells/well were seeded in a 96 well plate and stimulated with the indicated doses of IL-13 wt and the selected IL-13 agonists. After 96 h of stimulation, cells were harvested and cell number was determined using flow cytometry-based counting on an Accuri C6 flow cytometer. The number of cells obtained for each agonist was plotted against the cytokine concentration in order to obtain sigmoidal dose/response curves, from which the TF-1 proliferation EC50 values were calculated.

CAR Constructs

The codon-optimized IL-13 (E13Y) variant CAR sequence was previously described (Brown, Badie et al. 2015). The ribosomal skip T2A sequence (Donnelly, Luke et al. 2001) was fused by PCR splice overlap extension to the truncated CD19t sequence obtained from the leader peptide to the transmembrane spanning components (i.e., base pairs 1-972) of a CD19-containing plasmid. The IL13-variant and T2A-CD19t fragments were ligated into the previously described epHIV7 lentiviral vector (Wang, Naranjo et al. 2012). The CD28 costimulatory sequence was then inserted by splice overlap PCR, and then that construct underwent sequential site directed mutagenesis using the QuikChange II XL kit (Agilent Technologies, Santa Clara, CA) to generate the CAR variants.

Isolation of Enriched Tn/Mem Cells

Blood products were obtained from healthy donors under protocols approved by the City of Hope (COH) Internal Review Board. Peripheral blood mononuclear cells (PBMCs) were isolated by density gradient centrifugation over Ficoll-Paque (GE Healthcare, Little Chalfont, UK). PBMCs were incubated with clinical-grade anti-CD25 and anti-CD14 microbeads (Miltenyi Biotec, Bergisch Gladbach, Germany) for 30 min at room temperature (RT) in XVivo15 media (BioWhittaker, Walkersville, MD) containing 10% fetal calf serum (FBS) (HyClone, GE Healthcare). CD25+ and CD14+ cells were then immediately depleted using the CliniMACS depletion mode according to the manufacturer's instructions (Miltenyi Biotec). After centrifugation, the unlabeled negative fraction of cells was resuspended in CliniMACS PBS/EDTA buffer (Miltenyi Biotec) containing 0.5% human serum albumin (HSA) (CSL Behring, King of Prussia, PA) and then labeled with clinical grade biotinylated-DREG56 monoclonal antibody (mAb) (City of Hope Center for Biomedicine and Genetics) at 0.1 µg/$10^6$ cells for 30 min at RT. The cells were then washed and resuspended in a final volume of 100 mL CliniMACS PBS/EDTA containing 0.5% HSA. After 30 min incubation with 1.25 mL anti-biotin microbeads (Miltenyi Biotec), the CD62L+ fraction (Tn/mem) was purified with positive selection on CliniMACS according to the manufacturer's instructions and resuspended in X-Vivo15 media containing 10% FBS.

Activation, Lentiviral Transduction, and Ex Vivo Expansion of CAR T Cells

Tn/mem cells were stimulated with Dynabeads Human T expander CD3/CD28 (Invitrogen, Carlsbad, CA) at a 1:3 cell to bead ratio and transduced with lentivirus at an multiplicity of infection of 1.5-3 in X-Vivo15 containing 10% FBS (Hyclone Laboratories, Logan, UT) and 100 µg/mL protamine sulfate (APP Pharmaceuticals, Schaumburg, IL), 50 U/mL recombinant human (rh) IL-2, and 0.5 ng/mL rhIL-15. Cultures were then maintained at 37° C., 5% CO2, with addition of X-Vivo15 media (10% FBS) as required to keep cell density around $6\times10^5$ cells/mL, with cytokine supplementation 3 times a week. On day 7 of culture, the CD3/CD28 Dynabeads were removed from cultures using the DynaMag 5 magnet (Invitrogen). T cell lines were enriched with EasySep™ CD19 selection kit II (Stemcell, Cambridge, MA) around day 14 and propagated for 19-24 days prior to cryopreservation.

Cytokine Production Assays

For degranulation and intracellular IFN-γ assessment, CAR T cells and tumors were co-cultured at a 1:1 effector to target ratio in X-Vivo15 media without cytokines. CD107a and Golgi Stop (BD Biosciences, 1:1500 v/v) were added to the co-culture prior to the 5 hour incubation at 37° C. Subsequently, the intact cells were stained with human CD45, CD3, CD8, CD19 and IL13Rα2 antibodies. The cells were then fixed, permeabilized using Cytofix/Cytoperm (BD Biosciences) per manufacturer's instructions, stained for IFN-γ and analyzed.

For ELISAs, T cells were cultured overnight at $5\times103$ effector per well on flat bottom 96-well plates that had been coated with 500, 250, 125, 62.5 or 31.25 ng/well rhIL13Rα1-Fc chimera or IL13Rα2-Fc chimera (R&D Systems, Minneapolis, MN). Supernatants were then evaluated for IFN-γ levels using the Legend Max ELISA kit (BioLegend, San Diego, CA) per manufacturer's instructions.

Cytotoxicity Assays

T cells and tumors were co-cultured at 1:10 effector to target ratio in X-Vivo15 media without the addition of cytokines in 96-well plates for 2 days. For extended killing assays, effectors and targets were co-cultured at 1:50 ratio for 7 days in the absence of cytokines, with fresh media replenishment every 3-4 days. At the end of assay, adherent tumors were harvest enzymatically using trypsin (Corning, Corning, NY). Cells were then stained with human CD45, CD8, CD19 and IL13Rα2 and assessed by flow. Tumor killing by CART cells was calculated by comparing viable CD45-negative cell counts relative to that observed with mock (non-transduced) T cells.

Xenograft Models

All mouse experiments were approved by the COH Institute Animal Care and Use Committee. In orthotopic model, ffLuc+PBT030-2 cells ($1\times10^5$) were stereotactically implanted into the right forebrain of NSG mice on day 0. Mice were then treated intratumorally with $0.2$-$2.0\times106$ CAR T cells as indicated for each experiment. Groups of mice were then monitored for tumor engraftment by Xenogen non-invasive optical imaging as previously described (Kahlon, Brown et al. 2004), or for survival, with euthanasia applied according to the American Veterinary Medical Association Guidelines. Subcutaneous model was established by injecting HT1080 tumors ($5\times105$, 50 μl) in 50% v/v Matrigel® (coming, coming, NY) to the flank of NSG mice. Four days after tumor engraftment, CAR T cells ($5\times10^6$) were injected intratumorally and tumors sizes were monitored by caliper. To perform Winn assay, A549 tumors ($1\times10^5$) and CART cells ($1\times10^6$) were co-incubated in culture media at 37° C. for 2 hours. Cell mixtures were then mix with 50% v/v Matrigel® and injected to the flank of NSG mice.

Statistical Analysis

Statistical significance was determined by Student t-test (two groups), one-way ANOVA (>3 groups, Bonferroni adjustment) or Log-rank (Kaplan-Meir survival curve, Mantel-Cox adjustment) in GraphPad Prism (GraphPad Software, San Diego, CA). Significance levels are represented as *, $P<0.05$; , $P<0.01$; *, $P<0.001$; ns indicates not significant.

Beard, R. E., D. Abate-Daga, S. F. Rosati, Z. Zheng, J. R. Wunderlich, S. A. Rosenberg and R. A. Morgan (2013). "Gene expression profiling using nanostring digital RNA counting to identify potential target antigens for melanoma immunotherapy." Clin Cancer Res 19(18): 4941-4950.

Boder, E. T. and K. D. Wittrup (1997). "Yeast surface display for screening combinatorial polypeptide libraries." Nat Biotechnol 15(6): 553-557.

Boyiadzis, M. M., M. V. Dhodapkar, R. J. Brentjens, J. N. Kochenderfer, S. S. Neelapu, M. V. Maus, D. L. Porter, D. G. Maloney, S. A. Grupp, C. L. Mackall, C. H. June and M. R. Bishop (2018). "Chimeric antigen receptor (CAR) T therapies for the treatment of hematologic malignancies: clinical perspective and significance." J Immunother Cancer 6(1): 137.

Brombacher, T. M., J. K. Nono, K. S. De Gouveia, N. Makena, M. Darby, J. Womersley, O. Tamgue and F. Brombacher (2017). "IL-13-Mediated Regulation of Learning and Memory." J Immunol 198(7): 2681-2688.

Brown, C. E., D. Alizadeh, R. Starr, L. Weng, J. R. Wagner, A. Naranjo, J. R. Ostberg, M. S. Blanchard, J. Kilpatrick, J. Simpson, A. Kurien, S. J. Priceman, X. Wang, T. L. Harshbarger, M. D'Apuzzo, J. A. Ressler, M. C. Jensen, M. E. Barish, M. Chen, J. Portnow, S. J. Forman and B. Badie (2016). "Regression of Glioblastoma after Chimeric Antigen Receptor T-Cell Therapy." N Engl J Med 375(26): 2561-2569.

Brown, C. E., B. Badie, M. E. Barish, L. Weng, J. R. Ostberg, W. C. Chang, A. Naranjo, R. Starr, J. Wagner, C. Wright, Y. Zhai, J. R. Bading, J. A. Ressler, J. Portnow, M. D'Apuzzo, S. J. Forman and M. C. Jensen (2015). "Bioactivity and Safety of IL13Ralpha2-Redirected Chimeric Antigen Receptor CD8+ T Cells in Patients with Recurrent Glioblastoma." Clin Cancer Res 21(18): 4062-4072.

Brown, C. E., R. Starr, B. Aguilar, A. F. Shami, C. Martinez, M. D'Apuzzo, M. E. Barish, S. J. Forman and M. C. Jensen (2012). "Stem-like tumor-initiating cells isolated from IL13Ralpha2 expressing gliomas are targeted and killed by IL13-zetakine-redirected T Cells." Clin Cancer Res 18(8): 2199-2209.

Brown, C. E., C. D. Warden, R. Starr, X. Deng, B. Badie, Y. C. Yuan, S. J. Forman and M. E. Barish (2013). "Glioma IL13Ralpha2 is associated with mesenchymal signature gene expression and poor patient prognosis." PLoS One 8(10): e77769. Chiu, M. L. and G. L. Gilliland (2016). "Engineering antibody therapeutics." Curr Opin Struct Biol 38: 163-173.

Debinski, W. and D. M. Gibo (2000). "Molecular Expression Analysis of Restrictive Receptor for Interleukin 13, a Brain Tumor-associated Cancer/Testis Antigen." Molecular Medicine 6(5): 440-449.

Donnelly, M. L., G. Luke, A. Mehrotra, X. Li, L. E. Hughes, D. Gani and M. D. Ryan (2001). "Analysis of the aphthovirus 2A/2B polyprotein 'cleavage' mechanism indicates not a proteolytic reaction, but a novel translational effect: a putative ribosomal 'skip'." J Gen Virol 82 (Pt 5): 1013-1025.

Grupp, S. A., M. Kalos, D. Barrett, R. Aplenc, D. L. Porter, S. R. Rheingold, D. T. Teachey, A. Chew, B. Hauck, J. F. Wright, M. C. Milone, B. L. Levine and C. H. June (2013). "Chimeric antigen receptor-modified T cells for acute lymphoid leukemia." N Engl J Med 368(16): 1509-1518.

Hecker, M., Z. Zaslona, G. Kwapiszewska, G. Niess, A. Zakrzewicz, E. Hergenreider, J. Wilhelm, L. M. Marsh, D. Sedding, W. Klepetko, J. Lohmeyer, S. Dimmeler, W.

Seeger, N. Weissmann, R. T. Schermuly, N. Kneidinger, O. Eickelberg and R. E. Morty (2010). "Dysregulation of the IL-13 receptor system: a novel pathomechanism in pulmonary arterial hypertension." Am J Respir Crit Care Med 182(6): 805-818.

Hinck, A. P. (2018). "Structure-guided engineering of TGF-betas for the development of novel inhibitors and probing mechanism." Bioorg Med Chem 26(19): 5239-5246.

Jonnalagadda, M., A. Mardiros, R. Urak, X. Wang, L. J. Hoffman, A. Bemanke, W. C. Chang, W. Bretzlaff, R. Starr, S. Priceman, J. R. Ostberg, S. J. Forman and C. E. Brown (2015).

"Chimeric antigen receptors with mutated IgG4 Fc spacer avoid fc receptor binding and improve T cell persistence and antitumor efficacy." Mol Ther 23(4): 757-768.

Kahlon, K. S., C. Brown, L. J. Cooper, A. Raubitschek, S. J. Forman and M. C. Jensen (2004). "Specific recognition and killing of glioblastoma multiforme by interleukin 13-zetakine redirected cytolytic T cells." Cancer Res 64(24): 9160-9166.

Kahlon, K. S., C. Brown, L. J. N. Cooper, A. Raubitschek, S. J. Forman and M. C. Jensen (2004). "Specific Recognition and Killing of Glioblastoma Multiforme by Interleukin 13-Zetakine Redirected Cytolytic T Cells." Cancer Res 64: 9160-9166.

Kioi, M., M. Kawakami, T. Shimamura, S. R. Husain and R. K. Puri (2006). "Interleukin-13 receptor alpha2 chain: a potential biomarker and molecular target for ovarian cancer therapy." Cancer 107(6): 1407-1418.

Kong, S., S. Sengupta, B. Tyler, A. J. Bais, Q. Ma, S. Doucette, J. Zhou, A. Sahin, B. S. Carter, H. Brem, R. P. Junghans and P. Sampath (2012). "Suppression of human glioma xenografts with second-generation IL13R-specific chimeric antigen receptor-modified T cells." Clin Cancer Res 18(21): 5949-5960.

Krebs, S., K. K. Chow, Z. Yi, T. Rodriguez-Cruz, M. Hegde, C. Gerken, N. Ahmed and S. Gottschalk (2014). "T cells redirected to interleukin-13Ralpha2 with interleukin-13 mutein—chimeric antigen receptors have anti-glioma activity but also recognize interleukin-13Ralpha1." Cytotherapy 16(8): 1121-1131.

LaPorte, S. L., Z. S. Juo, J. Vaclavikova, L. A. Colf, X. Qi, N. M. Heller, A. D. Keegan and K. C. Garcia (2008). "Molecular and structural basis of cytokine receptor pleiotropy in the interleukin-4/13 system." Cell 132(2): 259-272.

Lee, L., B. Draper, N. Chaplin, B. Philip, M. Chin, D. Galas-Filipowicz, S. Onuoha, S. Thomas, V. Baldan, R. Bughda, P. Maciocia, E. Kokalaki, M. P. Neves, D. Patel, M. Rodriguez-Justo, J. Francis, K. Yong and M. Pule (2018). "An APRIL-based chimeric antigen receptor for dual targeting of BCMA and TACI in multiple myeloma." Blood 131(7): 746-758.

Long, K. B., R. M. Young, A. C. Boesteanu, M. M. Davis, J. J. Melenhorst, S. F. Lacey, D. A. DeGaramo, B. L. Levine and J. A. Fraietta (2018). "CART Cell Therapy of Non-hematopoietic Malignancies: Detours on the Road to Clinical Success." Frontiers in Immunology 9.

Lupardus, P. J., M. E. Birnbaum and K. C. Garcia (2010). "Molecular Basis for Shared Cytokine Recognition Revealed in the Structure of an Unusually High Affinity Complex between IL-13 and IL-13Rα2." Structure 18(3): 332-342.

Maude, S. L., N. Frey, P. A. Shaw, R. Aplenc, D. M. Barrett, N. J. Bunin, A. Chew, V. E. Gonzalez, Z. Zheng, S. F. Lacey, Y. D. Mahnke, J. J. Melenhorst, S. R. Rheingold, A. Shen, D. T. Teachey, B. L. Levine, C. H. June, D. L. Porter and S. A. Grupp (2014). "Chimeric antigen receptor T cells for sustained remissions in leukemia." N Engl J Med 371(16): 1507-1517.

Moraga, I., D. Richter, S. Wilmes, H. Winkelmann, K. Jude, C. Thomas, M. M. Suhoski, E. G. Engleman, J. Piehler and K. C. Garcia (2015). "Instructive roles for cytokine-receptor binding parameters in determining signaling and functional potency." Science Signaling 8(402).

Murata, T., J. Taguchi and R. K. Puri (1998). "Interleukin-13 Receptor Alpha' but Not Alpha Chain: A Functional Component of Interleukin-4 Receptors." Blood 91: 3884-3891.

Papageorgis, P., S. Ozturk, A. W. Lambert, C. M. Neophytou, A. Tzatsos, C. K. Wong, S. Thiagalingam and A. I. Constantinou (2015). "Targeting IL13Ralpha2 activates STAT6-TP63 pathway to suppress breast cancer lung metastasis." Breast Cancer Res 17: 98.

Porter, D. L., B. L. Levine, M. Kalos, A. Bagg and C. H. June (2011). "Chimeric Antigen Receptor-Modified T Cells in Chronic Lymphoid Leukemia." The New England Journal of Medicine 365(8): 725-733.

Rosenfeld, L., M. Heyne, J. M. Shifman and N. Papo (2016). "Protein Engineering by Combined Computational and In Vitro Evolution Approaches." Trends Biochem Sci 41(5): 421-433.

Shaffer, D. R., B. Savoldo, Z. Yi, K. K. Chow, S. Kakarla, D. M. Spencer, G. Dotti, M. F. Wu, H. Liu, S. Kenney and S. Gottschalk (2011). "T cells redirected against CD70 for the immunotherapy of CD70-positive malignancies." Blood 117(16): 4304-4314.

Shaffer, D. R., P. Zhou and S. Gottschalk (2014). "Foreign or Domestic CARs: Receptor Ligands as Antigen-Binding Domains." Medical Sciences 2: 23-36.

Shibasaki, N., T. Yamasaki, T. Kanno, R. Arakaki, H. Sakamoto, N. Utsunomiya, T. Inoue, T. Tsuruyama, E. Nakamura, O. Ogawa and T. Kamba (2015). "Role of IL13RA2 in Sunitinib Resistance in Clear Cell Renal Cell Carcinoma." PLoS One 10(6): e0130980.

Shimamura, T., T. Fujisawa, S. R. Husain, B. Joshi and R. K. Puri (2010). "Interleukin 13 mediates signal transduction through interleukin 13 receptor alpha2 in pancreatic ductal adenocarcinoma: role of IL-13 *Pseudomonas* exotoxin in pancreatic cancer therapy." Clin Cancer Res 16(2): 577-586.

Sockolosky, J. T., E. Trotta, G. Parisi, L. Picton, L. L. Su, A. C. Le, A. Chhabra, S. L. Silveria, B. M. George, I. C. King, M. R. Tiffany, K. Jude, L. V. Sibener, D. Baker, J. A. Shizuru, A. Ribas, J. A. Bluestone and K. C. Garcia (2018). "Selective targeting of engineered T cells using orthogonal IL-2 cytokine-receptor complexes." Science 359: 1037-1042.

Thaci, B., C. E. Brown, E. Binello, K. Werbaneth, P. Sampath and S. Sengupta (2014). "Significance of interleukin-13 receptor alpha 2-targeted glioblastoma therapy." Neuro-Oncology 16(10): 1304-1312.

Wang, X., A. Naranjo, C. E. Brown, C. Bautista, C. W. Wong, W. C. Chang, B. Aguilar, J. R. Ostberg, S. R. Riddell, S. J. Forman and M. C. Jensen (2012). "Phenotypic and functional attributes of lentivirus-modified CD19-specific human CD8+ central memory T cells manufactured at clinical scale." J Immunother 35(9): 689-701.

Winn, H. J. (1960). "Immune mechanisms in homotransplantation. I. The role of serum antibody and complement in the neutralization of lymphoma cells." J Immunol 84: 530-538.

Winn, H. J. (1961). "Immune mechanisms in homotransplantation. II. Quantitative assay of the immunologic activity of lymphoid cells stimulated by tumor homografts." J Immunol 86: 228-239.

Xie, M., X. Wu, J. Zhang and C. He (2015). "IL-13 receptor a2 is a negative prognostic factor in human lung cancer and stimulates lung cancer growth in mice." Oncotarget 6(32): 32902-32913.

Zhang, T., B. A. Lemoi and C. L. Sentman (2005). "Chimeric NK-receptor-bearing T cells mediate antitumor immunotherapy." Blood $10^6$(5): 1544-1551.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. All references are herein incorporated in their entirety for any and all purposes.

What is claimed is:

1. A nucleic molecule comprising a nucleotide sequence encoding a chimeric antigen receptor (CAR), wherein—the CAR comprises or consists of an amino acid sequence selected from the group consisting of an amino acid sequence that is at least 98% identical to an amino acid sequence selected from SEQ ID NOs: 29, 30, 32, 33, 35, 36, 38 and 39 and comprises a targeting domain comprising or consisting of an amino acid sequence identical to SEQ ID NO: 26 or 27.

2. The nucleic acid molecule of claim 1, wherein the chimeric antigen receptor comprises or consists of an amino acid sequence selected from the group consisting of an amino acid sequence selected from SEQ ID NOs: 29, 30, 32, 33, 35, 36, 38 and 39.

3. The nucleic acid molecule of claim 1, wherein the chimeric antigen receptor comprises or consists of an amino acid sequence selected from the group consisting of: an amino acid sequence selected from SEQ ID NOs: 29, 32, 35 and 38.

4. An expression vector comprising the nucleic acid molecule of claim 1.

5. A viral vector comprising the nucleic acid molecule of claim 1.

6. A population of human T cells transduced by a vector comprising the nucleic acid molecule of claim 1.

7. The population of human T cells of claim 6, wherein the population of human T cells comprise central memory T cells, naive memory T cells, pan T cells, or PBMC depleted for CD25+ cells and CD14+ cells.

8. A method of preparing CAR T cells comprising: providing a population of autologous or allogeneic human T cells and transducing the T cells by a vector comprising the nucleic acid molecule of claim 1.

9. A method of treating a cancer patient suffering from a cancer expressing IL-13Rα2, wherein the cancer is selected from glioblastoma, pancreatic ductal adenocarcinoma, melanoma, ovarian carcinoma, renal cell carcinoma, breast cancer or lung cancer, comprising administering a population of autologous or allogeneic human T cells transduced by a vector comprising the nucleic acid molecule of claim 1.

10. The method of claim 9, wherein the cells are administered locally or systemically.

11. The method of claim 10, wherein the cells are administered by single or repeat dosing.

12. The method of claim 9, wherein the patient is suffering from glioblastoma.

13. The method of claim 12, wherein the chimeric antigen receptor comprises or consists of an amino acid sequence selected from the group consisting of an amino acid sequence selected from SEQ ID NOs: 29, 30, 32, 33, 35, 36, 38 and 39.

14. The method of claim 13, wherein the population of human T cells are allogenic human T cells.

15. The method of claim 13, wherein the population of human T cells are autologous human T cells.

16. A chimeric antigen receptor comprising or consisting of an amino acid sequence selected from the group consisting of an amino acid sequence that is at least 98% identical to an amino acid sequence selected from SEQ ID NOs: 29, 30, 32, 33, 35, 36, 38 and 39.

17. The chimeric antigen receptor of claim 16, comprising or consisting of an amino acid sequence selected from the group consisting of an amino acid sequence selected from SEQ ID NOs: 29, 30, 32, 33, 35, 36, 38 and 39.

18. The chimeric antigen receptor of claim 16, comprising or consisting of an amino acid sequence selected from the group consisting of an amino acid sequence selected from SEQ ID NOs: SEQ ID NOs: 29, 32, 35 and 38.

19. A population of human T cells expressing the chimeric antigen receptor of claim 16.

20. The population of human T cells of claim 19, wherein the population of human T cells comprise central memory T cells, naive memory T cells, pan T cells, or PBMC depleted for CD25+ cells and CD14+ cells.

* * * * *

UNITED STATES PATENT AND TRADEMARK OFFICE
CERTIFICATE OF CORRECTION

| | | |
|---|---|---|
| PATENT NO. | : 12,419,954 B2 | Page 1 of 1 |
| APPLICATION NO. | : 17/796349 | |
| DATED | : September 23, 2025 | |
| INVENTOR(S) | : Christine E. Brown et al. | |

It is certified that error appears in the above-identified patent and that said Letters Patent is hereby corrected as shown below:

On the Title Page

Right column, item (56) "References Cited", Line 3, below the "FOREIGN PATENT DOCUMENTS" heading, delete "12/2012" and insert -- 12/2019 --

In the Specification

Column 1, Line 14, before the "SEQUENCE LISTING" header, insert the following new heading and new paragraph:
-- FEDERALLY SPONSORED RESEARCH OR DEVELOPMENT
This invention was made with Government support under contract AI051321 awarded by the National Institutes of Health. The Government has certain rights in the invention. --

In the Claims

Column 87, Line 2, Claim 1, delete "nucleic" and insert -- nucleic acid --

Column 87, Line 3, Claim 1, delete "wherein—the" and insert -- wherein the --

Column 88, Line 31, Claim 18, delete "SEQ ID NOs: SEQ ID NOs:" and insert -- SEQ ID NOs: --

Signed and Sealed this
Twenty-fifth Day of November, 2025

John A. Squires
*Director of the United States Patent and Trademark Office*

SEQUENCE LISTING

```
<160> NUMBER OF SEQ ID NOS: 42

<210> SEQ ID NO 1
<211> LENGTH: 22
<212> TYPE: PRT
<213> ORGANISM: Artificial Sequence
<220> FEATURE:
<223> OTHER INFORMATION: GMCSFRa signal sequence

<400> SEQUENCE: 1

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 2
<211> LENGTH: 10
<212> TYPE: PRT
<213> ORGANISM: Artificial Sequence
<220> FEATURE:
<223> OTHER INFORMATION: linker

<400> SEQUENCE: 2

Gly Gly Gly Ser Ser Gly Gly Gly Ser Gly
1               5                   10

<210> SEQ ID NO 3
<211> LENGTH: 12
<212> TYPE: PRT
<213> ORGANISM: Artificial Sequence
<220> FEATURE:
<223> OTHER INFORMATION: IgG4 hinge (S to P) (S228P)

<400> SEQUENCE: 3

Glu Ser Lys Tyr Gly Pro Pro Cys Pro Pro Cys Pro
1               5                   10

<210> SEQ ID NO 4
<211> LENGTH: 12
<212> TYPE: PRT
<213> ORGANISM: Artificial Sequence
<220> FEATURE:
<223> OTHER INFORMATION: IgG4 hinge

<400> SEQUENCE: 4

Glu Ser Lys Tyr Gly Pro Pro Cys Pro Ser Cys Pro
1               5                   10

<210> SEQ ID NO 5
<211> LENGTH: 22
<212> TYPE: PRT
<213> ORGANISM: Artificial Sequence
<220> FEATURE:
<223> OTHER INFORMATION: IgG4 hinge (S228P)+ linker
```

<400> SEQUENCE: 5

Glu Ser Lys Tyr Gly Pro Pro Cys Pro Pro Cys Pro Gly Gly Gly Ser
1               5                   10                  15

Ser Gly Gly Gly Ser Gly
            20

<210> SEQ ID NO 6
<211> LENGTH: 39
<212> TYPE: PRT
<213> ORGANISM: Artificial Sequence
<220> FEATURE:
<223> OTHER INFORMATION: CD28 hinge

<400> SEQUENCE: 6

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 7
<211> LENGTH: 48
<212> TYPE: PRT
<213> ORGANISM: Artificial Sequence
<220> FEATURE:
<223> OTHER INFORMATION: CD8 hinge-48aa

<400> SEQUENCE: 7

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45

<210> SEQ ID NO 8
<211> LENGTH: 45
<212> TYPE: PRT
<213> ORGANISM: Artificial Sequence
<220> FEATURE:
<223> OTHER INFORMATION: CD8 hinge-45aa

<400> SEQUENCE: 8

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 9
<211> LENGTH: 129
<212> TYPE: PRT
<213> ORGANISM: Artificial Sequence
<220> FEATURE:
<223> OTHER INFORMATION: IgG4(HL-CH3) (includes S228P in hinge)

<400> SEQUENCE: 9

Glu Ser Lys Tyr Gly Pro Pro Cys Pro Pro Cys Pro Gly Gly Gly Ser
1               5                   10                  15

Ser Gly Gly Gly Ser Gly Gly Gln Pro Arg Glu Pro Gln Val Tyr Thr
            20                  25                  30

Leu Pro Pro Ser Gln Glu Glu Met Thr Lys Asn Gln Val Ser Leu Thr
        35                  40                  45

Cys Leu Val Lys Gly Phe Tyr Pro Ser Asp Ile Ala Val Glu Trp Glu
    50                  55                  60

Ser Asn Gly Gln Pro Glu Asn Asn Tyr Lys Thr Thr Pro Pro Val Leu
65                  70                  75                  80

Asp Ser Asp Gly Ser Phe Phe Leu Tyr Ser Arg Leu Thr Val Asp Lys
                85                  90                  95

Ser Arg Trp Gln Glu Gly Asn Val Phe Ser Cys Ser Val Met His Glu
            100                 105                 110

Ala Leu His Asn His Tyr Thr Gln Lys Ser Leu Ser Leu Ser Leu Gly
        115                 120                 125

Lys

<210> SEQ ID NO 10
<211> LENGTH: 229
<212> TYPE: PRT
<213> ORGANISM: Artificial Sequence
<220> FEATURE:
<223> OTHER INFORMATION: IgG4(L235E,N297Q)

<400> SEQUENCE: 10

Glu Ser Lys Tyr Gly Pro Pro Cys Pro Ser Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Gln Ala Lys Thr Lys Pro Arg Glu Gln Phe Gln Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

```
<210> SEQ ID NO 11
<211> LENGTH: 229
<212> TYPE: PRT
<213> ORGANISM: Artificial Sequence
<220> FEATURE:
<223> OTHER INFORMATION: IgG4(S228P, L235E, N297Q)

<400> SEQUENCE: 11
```

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Gln Ala Lys Thr Lys Pro Arg Glu Gln Phe Gln Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

```
<210> SEQ ID NO 12
<211> LENGTH: 107
<212> TYPE: PRT
<213> ORGANISM: Artificial Sequence
<220> FEATURE:
<223> OTHER INFORMATION: IgG4(CH3)

<400> SEQUENCE: 12
```

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

```
Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 13
<211> LENGTH: 21
<212> TYPE: PRT
<213> ORGANISM: Artificial Sequence
<220> FEATURE:
<223> OTHER INFORMATION: CD3z

<400> SEQUENCE: 13

Leu Cys Tyr Leu Leu Asp Gly Ile Leu Phe Ile Tyr Gly Val Ile Leu
1               5                   10                  15

Thr Ala Leu Phe Leu
            20

<210> SEQ ID NO 14
<211> LENGTH: 27
<212> TYPE: PRT
<213> ORGANISM: Artificial Sequence
<220> FEATURE:
<223> OTHER INFORMATION: CD28

<400> SEQUENCE: 14

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 15
<211> LENGTH: 28
<212> TYPE: PRT
<213> ORGANISM: Artificial Sequence
<220> FEATURE:
<223> OTHER INFORMATION: CD28(M)

<400> SEQUENCE: 15

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25

<210> SEQ ID NO 16
<211> LENGTH: 22
<212> TYPE: PRT
<213> ORGANISM: Artificial Sequence
<220> FEATURE:
<223> OTHER INFORMATION: CD4

<400> SEQUENCE: 16

Met Ala Leu Ile Val Leu Gly Gly Val Ala Gly Leu Leu Leu Phe Ile
1               5                   10                  15

Gly Leu Gly Ile Phe Phe
            20

<210> SEQ ID NO 17
<211> LENGTH: 21
<212> TYPE: PRT
<213> ORGANISM: Artificial Sequence
<220> FEATURE:
<223> OTHER INFORMATION: CD8tm

<400> SEQUENCE: 17
```

```
Ile Tyr Ile Trp Ala Pro Leu Ala Gly Thr Cys Gly Val Leu Leu Leu
1               5                   10                  15

Ser Leu Val Ile Thr
            20
```

<210> SEQ ID NO 18
<211> LENGTH: 23
<212> TYPE: PRT
<213> ORGANISM: Artificial Sequence
<220> FEATURE:
<223> OTHER INFORMATION: CD8tm2

<400> SEQUENCE: 18

```
Ile Tyr Ile Trp Ala Pro Leu Ala Gly Thr Cys Gly Val Leu Leu Leu
1               5                   10                  15

Ser Leu Val Ile Thr Leu Tyr
            20
```

<210> SEQ ID NO 19
<211> LENGTH: 24
<212> TYPE: PRT
<213> ORGANISM: Artificial Sequence
<220> FEATURE:
<223> OTHER INFORMATION: CD8tm3

<400> SEQUENCE: 19

```
Ile Tyr Ile Trp Ala Pro Leu Ala Gly Thr Cys Gly Val Leu Leu Leu
1               5                   10                  15

Ser Leu Val Ile Thr Leu Tyr Cys
            20
```

<210> SEQ ID NO 20
<211> LENGTH: 27
<212> TYPE: PRT
<213> ORGANISM: Artificial Sequence
<220> FEATURE:
<223> OTHER INFORMATION: 41BB

<400> SEQUENCE: 20

```
Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25
```

<210> SEQ ID NO 21
<211> LENGTH: 112
<212> TYPE: PRT
<213> ORGANISM: Artificial Sequence
<220> FEATURE:
<223> OTHER INFORMATION: CD3

<400> SEQUENCE: 21

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80
```

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 22
<211> LENGTH: 41
<212> TYPE: PRT
<213> ORGANISM: Artificial Sequence
<220> FEATURE:
<223> OTHER INFORMATION: CD28

<400> SEQUENCE: 22

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 23
<211> LENGTH: 41
<212> TYPE: PRT
<213> ORGANISM: Artificial Sequence
<220> FEATURE:
<223> OTHER INFORMATION: CD28gg

<400> SEQUENCE: 23

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 24
<211> LENGTH: 42
<212> TYPE: PRT
<213> ORGANISM: Artificial Sequence
<220> FEATURE:
<223> OTHER INFORMATION: 4-1BB co-signaling

<400> SEQUENCE: 24

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 25
<211> LENGTH: 42
<212> TYPE: PRT
<213> ORGANISM: Artificial Sequence
<220> FEATURE:
<223> OTHER INFORMATION: OX40

<400> SEQUENCE: 25

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

```
Ala Asp Ala His Ser Thr Leu Ala Lys Ile
        35                  40

<210> SEQ ID NO 26
<211> LENGTH: 112
<212> TYPE: PRT
<213> ORGANISM: Artificial Sequence
<220> FEATURE:
<223> OTHER INFORMATION: variant IL13

<400> SEQUENCE: 26

Gly Pro Val Pro Pro Ser Thr Ala Val Arg Glu Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Arg Ile Glu Val Ala Gln Phe Val Lys
                85                  90                  95

Asp Leu Leu Asn His Leu Lys Glu Leu Phe Thr Glu Gly Gln Phe Asn
            100                 105                 110

<210> SEQ ID NO 27
<211> LENGTH: 112
<212> TYPE: PRT
<213> ORGANISM: Artificial Sequence
<220> FEATURE:
<223> OTHER INFORMATION: variant IL13

<400> SEQUENCE: 27

Gly Pro Val Pro Pro Ser Thr Ala Ala Arg Glu Leu Ile Glu Glu Leu
1               5                   10                  15

Phe Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Lys Arg
    50                  55                  60

Met Leu Ser Gly Phe Cys Pro His Lys Val Ser Ala Gly Gln Phe Pro
65                  70                  75                  80

Ser Leu His Val Lys Lys Thr Arg Ile Glu Val Ala Gln Phe Val Lys
                85                  90                  95

Asp Leu Leu Ile His Leu Arg Lys Leu Phe Lys Glu Gly Gln Phe Asn
            100                 105                 110

<210> SEQ ID NO 28
<211> LENGTH: 894
<212> TYPE: PRT
<213> ORGANISM: Artificial Sequence
<220> FEATURE:
<223> OTHER INFORMATION: IL13(C4)-IgG4(L235E,N297Q)-CD28gg-Zeta(CO)-T2A-
      CD19t

<400> SEQUENCE: 28

Met Leu Leu Leu Val Thr Ser Leu Leu Leu Cys Glu Leu Pro His Pro
1               5                   10                  15
```

-continued

Ala Phe Leu Leu Ile Pro Gly Pro Val Pro Ser Thr Ala Val Arg
            20              25              30

Glu Leu Ile Glu Glu Leu Val Asn Ile Thr Gln Asn Gln Lys Ala Pro
        35              40              45

Leu Cys Asn Gly Ser Met Val Trp Ser Ile Asn Leu Thr Ala Gly Met
 50              55              60

Tyr Cys Ala Ala Leu Glu Ser Leu Ile Asn Val Ser Gly Cys Ser Ala
 65              70              75              80

Ile Glu Lys Thr Gln Arg Met Leu Ser Gly Phe Cys Pro His Lys Val
            85              90              95

Ser Ala Gly Gln Phe Ser Ser Leu His Val Arg Asp Thr Arg Ile Glu
            100             105             110

Val Ala Gln Phe Val Lys Asp Leu Leu Asn His Leu Lys Glu Leu Phe
        115             120             125

Thr Glu Gly Gln Phe Asn Glu Ser Lys Tyr Gly Pro Pro Cys Pro Pro
 130             135             140

Cys Pro Ala Pro Glu Phe Glu Gly Gly Pro Ser Val Phe Leu Phe Pro
145             150             155             160

Pro Lys Pro Lys Asp Thr Leu Met Ile Ser Arg Thr Pro Glu Val Thr
            165             170             175

Cys Val Val Val Asp Val Ser Gln Glu Asp Pro Glu Val Gln Phe Asn
            180             185             190

Trp Tyr Val Asp Gly Val Glu Val His Asn Ala Lys Thr Lys Pro Arg
        195             200             205

Glu Glu Gln Phe Gln Ser Thr Tyr Arg Val Val Ser Val Leu Thr Val
    210             215             220

Leu His Gln Asp Trp Leu Asn Gly Lys Glu Tyr Lys Cys Lys Val Ser
225             230             235             240

Asn Lys Gly Leu Pro Ser Ser Ile Glu Lys Thr Ile Ser Lys Ala Lys
            245             250             255

Gly Gln Pro Arg Glu Pro Gln Val Tyr Thr Leu Pro Pro Ser Gln Glu
            260             265             270

Glu Met Thr Lys Asn Gln Val Ser Leu Thr Cys Leu Val Lys Gly Phe
        275             280             285

Tyr Pro Ser Asp Ile Ala Val Glu Trp Glu Ser Asn Gly Gln Pro Glu
 290             295             300

Asn Asn Tyr Lys Thr Thr Pro Pro Val Leu Asp Ser Asp Gly Ser Phe
305             310             315             320

Phe Leu Tyr Ser Arg Leu Thr Val Asp Lys Ser Arg Trp Gln Glu Gly
            325             330             335

Asn Val Phe Ser Cys Ser Val Met His Glu Ala Leu His Asn His Tyr
            340             345             350

Thr Gln Lys Ser Leu Ser Leu Ser Leu Gly Lys Met Phe Trp Val Leu
        355             360             365

Val Val Val Gly Gly Val Leu Ala Cys Tyr Ser Leu Leu Val Thr Val
    370             375             380

Ala Phe Ile Ile Phe Trp Val Arg Ser Lys Arg Ser Arg Gly Gly His
385             390             395             400

Ser Asp Tyr Met Asn Met Thr Pro Arg Arg Pro Gly Pro Thr Arg Lys
            405             410             415

His Tyr Gln Pro Tyr Ala Pro Pro Arg Asp Phe Ala Ala Tyr Arg Ser
        420             425             430

Gly Gly Gly Arg Val Lys Phe Ser Arg Ser Ala Asp Ala Pro Ala Tyr
            435                 440                 445

Gln Gln Gly Gln Asn Gln Leu Tyr Asn Glu Leu Asn Leu Gly Arg Arg
            450                 455                 460

Glu Glu Tyr Asp Val Leu Asp Lys Arg Gly Arg Asp Pro Glu Met
465                 470                 475                 480

Gly Gly Lys Pro Arg Arg Lys Asn Pro Gln Glu Gly Leu Tyr Asn Glu
                485                 490                 495

Leu Gln Lys Asp Lys Met Ala Glu Ala Tyr Ser Glu Ile Gly Met Lys
            500                 505                 510

Gly Glu Arg Arg Arg Gly Lys Gly His Asp Gly Leu Tyr Gln Gly Leu
            515                 520                 525

Ser Thr Ala Thr Lys Asp Thr Tyr Asp Ala Leu His Met Gln Ala Leu
            530                 535                 540

Pro Pro Arg Leu Glu Gly Gly Gly Glu Gly Arg Gly Ser Leu Leu Thr
545                 550                 555                 560

Cys Gly Asp Val Glu Glu Asn Pro Gly Pro Arg Met Pro Pro Arg
            565                 570                 575

Leu Leu Phe Phe Leu Leu Phe Leu Thr Pro Met Glu Val Arg Pro Glu
            580                 585                 590

Glu Pro Leu Val Val Lys Val Glu Glu Gly Asp Asn Ala Val Leu Gln
            595                 600                 605

Cys Leu Lys Gly Thr Ser Asp Gly Pro Thr Gln Gln Leu Thr Trp Ser
            610                 615                 620

Arg Glu Ser Pro Leu Lys Pro Phe Leu Lys Leu Ser Leu Gly Leu Pro
625                 630                 635                 640

Gly Leu Gly Ile His Met Arg Pro Leu Ala Ile Trp Leu Phe Ile Phe
            645                 650                 655

Asn Val Ser Gln Gln Met Gly Gly Phe Tyr Leu Cys Gln Pro Gly Pro
            660                 665                 670

Pro Ser Glu Lys Ala Trp Gln Pro Gly Trp Thr Val Asn Val Glu Gly
            675                 680                 685

Ser Gly Glu Leu Phe Arg Trp Asn Val Ser Asp Leu Gly Gly Leu Gly
            690                 695                 700

Cys Gly Leu Lys Asn Arg Ser Ser Glu Gly Pro Ser Ser Pro Ser Gly
705                 710                 715                 720

Lys Leu Met Ser Pro Lys Leu Tyr Val Trp Ala Lys Asp Arg Pro Glu
                725                 730                 735

Ile Trp Glu Gly Glu Pro Pro Cys Val Pro Arg Asp Ser Leu Asn
            740                 745                 750

Gln Ser Leu Ser Gln Asp Leu Thr Met Ala Pro Gly Ser Thr Leu Trp
            755                 760                 765

Leu Ser Cys Gly Val Pro Pro Asp Ser Val Ser Arg Gly Pro Leu Ser
770                 775                 780

Trp Thr His Val His Pro Lys Gly Pro Lys Ser Leu Leu Ser Leu Glu
785                 790                 795                 800

Leu Lys Asp Asp Arg Pro Ala Arg Asp Met Trp Val Met Glu Thr Gly
            805                 810                 815

Leu Leu Leu Pro Arg Ala Thr Ala Gln Asp Ala Gly Lys Tyr Tyr Cys
            820                 825                 830

His Arg Gly Asn Leu Thr Met Ser Phe His Leu Glu Ile Thr Ala Arg
            835                 840                 845

Pro Val Leu Trp His Trp Leu Leu Arg Thr Gly Gly Trp Lys Val Ser

```
                850                 855                 860
Ala Val Thr Leu Ala Tyr Leu Ile Phe Cys Leu Cys Ser Leu Val Gly
865                 870                 875                 880

Ile Leu His Leu Gln Arg Ala Leu Val Leu Arg Arg Lys Arg
                885                 890

<210> SEQ ID NO 29
<211> LENGTH: 525
<212> TYPE: PRT
<213> ORGANISM: Artificial Sequence
<220> FEATURE:
<223> OTHER INFORMATION: mature IL13(C4)-IgG4(L235E,N297Q)-CD28gg-
      Zeta(CO)

<400> SEQUENCE: 29

Gly Pro Val Pro Pro Ser Thr Ala Val Arg Glu Leu Ile Glu Glu Leu
1               5                   10                  15

Val Asn Ile Thr Gln Asn Gln Lys Ala Pro Leu Cys Asn Gly Ser Met
                20                  25                  30

Val Trp Ser Ile Asn Leu Thr Ala Gly Met Tyr Cys Ala Ala Leu Glu
            35                  40                  45

Ser Leu Ile Asn Val Ser Gly Cys Ser Ala Ile Glu Lys Thr Gln Arg
        50                  55                  60

Met Leu Ser Gly Phe Cys Pro His Lys Val Ser Ala Gly Gln Phe Ser
65                  70                  75                  80

Ser Leu His Val Arg Asp Thr Arg Ile Glu Val Ala Gln Phe Val Lys
                85                  90                  95

Asp Leu Leu Asn His Leu Lys Glu Leu Phe Thr Glu Gly Gln Phe Asn
                100                 105                 110

Glu Ser Lys Tyr Gly Pro Pro Cys Pro Pro Cys Pro Ala Pro Glu Phe
            115                 120                 125

Glu Gly Gly Pro Ser Val Phe Leu Phe Pro Pro Lys Pro Lys Asp Thr
        130                 135                 140

Leu Met Ile Ser Arg Thr Pro Glu Val Thr Cys Val Val Val Asp Val
145                 150                 155                 160

Ser Gln Glu Asp Pro Glu Val Gln Phe Asn Trp Tyr Val Asp Gly Val
                165                 170                 175

Glu Val His Asn Ala Lys Thr Lys Pro Arg Glu Glu Gln Phe Gln Ser
            180                 185                 190

Thr Tyr Arg Val Val Ser Val Leu Thr Val Leu His Gln Asp Trp Leu
        195                 200                 205

Asn Gly Lys Glu Tyr Lys Cys Lys Val Ser Asn Lys Gly Leu Pro Ser
    210                 215                 220

Ser Ile Glu Lys Thr Ile Ser Lys Ala Lys Gly Gln Pro Arg Glu Pro
225                 230                 235                 240

Gln Val Tyr Thr Leu Pro Pro Ser Gln Glu Glu Met Thr Lys Asn Gln
                245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
        275                 280                 285

Pro Pro Val Leu Asp Ser Asp Gly Ser Phe Phe Leu Tyr Ser Arg Leu
    290                 295                 300

Thr Val Asp Lys Ser Arg Trp Gln Glu Gly Asn Val Phe Ser Cys Ser
305                 310                 315                 320
```

```
Val Met His Glu Ala Leu His Asn His Tyr Thr Gln Lys Ser Leu Ser
            325                 330                 335

Leu Ser Leu Gly Lys Met Phe Trp Val Leu Val Val Val Gly Gly Val
            340                 345                 350

Leu Ala Cys Tyr Ser Leu Leu Val Thr Val Ala Phe Ile Ile Phe Trp
            355                 360                 365

Val Arg Ser Lys Arg Ser Arg Gly Gly His Ser Asp Tyr Met Asn Met
370                 375                 380

Thr Pro Arg Arg Pro Gly Pro Thr Arg Lys His Tyr Gln Pro Tyr Ala
385                 390                 395                 400

Pro Pro Arg Asp Phe Ala Ala Tyr Arg Ser Gly Gly Arg Val Lys
            405                 410                 415

Phe Ser Arg Ser Ala Asp Ala Pro Ala Tyr Gln Gln Gly Gln Asn Gln
            420                 425                 430

Leu Tyr Asn Glu Leu Asn Leu Gly Arg Arg Glu Glu Tyr Asp Val Leu
            435                 440                 445

Asp Lys Arg Arg Gly Arg Asp Pro Glu Met Gly Gly Lys Pro Arg Arg
450                 455                 460

Lys Asn Pro Gln Glu Gly Leu Tyr Asn Glu Leu Gln Lys Asp Lys Met
465                 470                 475                 480

Ala Glu Ala Tyr Ser Glu Ile Gly Met Lys Gly Glu Arg Arg Arg Gly
            485                 490                 495

Lys Gly His Asp Gly Leu Tyr Gln Gly Leu Ser Thr Ala Thr Lys Asp
            500                 505                 510

Thr Tyr Asp Ala Leu His Met Gln Ala Leu Pro Pro Arg
            515                 520                 525

<210> SEQ ID NO 30
<211> LENGTH: 547
<212> TYPE: PRT
<213> ORGANISM: Artificial Sequence
<220> FEATURE:
<223> OTHER INFORMATION: IL13(C4)-IgG4(L235E,N297Q)-CD28gg-Zeta(CO) with
      a signal sequence

<400> SEQUENCE: 30

Met Leu Leu Leu Val Thr Ser Leu Leu Leu Cys Glu Leu Pro His Pro
1               5                   10                  15

Ala Phe Leu Leu Ile Pro Gly Pro Val Pro Pro Ser Thr Ala Val Arg
            20                  25                  30

Glu Leu Ile Glu Glu Leu Val Asn Ile Thr Gln Asn Gln Lys Ala Pro
        35                  40                  45

Leu Cys Asn Gly Ser Met Val Trp Ser Ile Asn Leu Thr Ala Gly Met
    50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Arg Ile Glu
            100                 105                 110

Val Ala Gln Phe Val Lys Asp Leu Leu Asn His Leu Lys Glu Leu Phe
        115                 120                 125

Thr Glu Gly Gln Phe Asn Glu Ser Lys Tyr Gly Pro Pro Cys Pro Pro
    130                 135                 140

Cys Pro Ala Pro Glu Phe Glu Gly Gly Pro Ser Val Phe Leu Phe Pro
145                 150                 155                 160
```

```
Pro Lys Pro Lys Asp Thr Leu Met Ile Ser Arg Thr Pro Glu Val Thr
                165                 170                 175
Cys Val Val Val Asp Val Ser Gln Glu Asp Pro Glu Val Gln Phe Asn
            180                 185                 190
Trp Tyr Val Asp Gly Val Glu Val His Asn Ala Lys Thr Lys Pro Arg
        195                 200                 205
Glu Glu Gln Phe Gln Ser Thr Tyr Arg Val Val Ser Val Leu Thr Val
    210                 215                 220
Leu His Gln Asp Trp Leu Asn Gly Lys Glu Tyr Lys Cys Lys Val Ser
225                 230                 235                 240
Asn Lys Gly Leu Pro Ser Ser Ile Glu Lys Thr Ile Ser Lys Ala Lys
                245                 250                 255
Gly Gln Pro Arg Glu Pro Gln Val Tyr Thr Leu Pro Pro Ser Gln Glu
            260                 265                 270
Glu Met Thr Lys Asn Gln Val Ser Leu Thr Cys Leu Val Lys Gly Phe
        275                 280                 285
Tyr Pro Ser Asp Ile Ala Val Glu Trp Glu Ser Asn Gly Gln Pro Glu
    290                 295                 300
Asn Asn Tyr Lys Thr Thr Pro Pro Val Leu Asp Ser Asp Gly Ser Phe
305                 310                 315                 320
Phe Leu Tyr Ser Arg Leu Thr Val Asp Lys Ser Arg Trp Gln Glu Gly
                325                 330                 335
Asn Val Phe Ser Cys Ser Val Met His Glu Ala Leu His Asn His Tyr
            340                 345                 350
Thr Gln Lys Ser Leu Ser Leu Ser Leu Gly Lys Met Phe Trp Val Leu
        355                 360                 365
Val Val Val Gly Gly Val Leu Ala Cys Tyr Ser Leu Leu Val Thr Val
    370                 375                 380
Ala Phe Ile Ile Phe Trp Val Arg Ser Lys Arg Ser Arg Gly Gly His
385                 390                 395                 400
Ser Asp Tyr Met Asn Met Thr Pro Arg Arg Pro Gly Pro Thr Arg Lys
                405                 410                 415
His Tyr Gln Pro Tyr Ala Pro Pro Arg Asp Phe Ala Ala Tyr Arg Ser
            420                 425                 430
Gly Gly Gly Arg Val Lys Phe Ser Arg Ser Ala Asp Ala Pro Ala Tyr
        435                 440                 445
Gln Gln Gly Gln Asn Gln Leu Tyr Asn Glu Leu Asn Leu Gly Arg Arg
    450                 455                 460
Glu Glu Tyr Asp Val Leu Asp Lys Arg Arg Gly Arg Asp Pro Glu Met
465                 470                 475                 480
Gly Gly Lys Pro Arg Arg Lys Asn Pro Gln Glu Gly Leu Tyr Asn Glu
                485                 490                 495
Leu Gln Lys Asp Lys Met Ala Glu Ala Tyr Ser Glu Ile Gly Met Lys
            500                 505                 510
Gly Glu Arg Arg Arg Gly Lys Gly His Asp Gly Leu Tyr Gln Gly Leu
        515                 520                 525
Ser Thr Ala Thr Lys Asp Thr Tyr Asp Ala Leu His Met Gln Ala Leu
    530                 535                 540
Pro Pro Arg
545

<210> SEQ ID NO 31
<211> LENGTH: 789
```

```
<212> TYPE: PRT
<213> ORGANISM: Artificial Sequence
<220> FEATURE:
<223> OTHER INFORMATION: IL13(C4)-IgG4(HL-CH3)-CD4tm-41BB-Zeta(CO)-T2A-
      CD19t(BspEI)

<400> SEQUENCE: 31
```

| | | | | | | | | | | | | | | | |
|---|---|---|---|---|---|---|---|---|---|---|---|---|---|---|---|
| Met | Leu | Leu | Leu | Val | Thr | Ser | Leu | Leu | Leu | Cys | Glu | Leu | Pro | His | Pro |
| 1 | | | | 5 | | | | | 10 | | | | | 15 | |
| Ala | Phe | Leu | Leu | Ile | Pro | Gly | Pro | Val | Pro | Pro | Ser | Thr | Ala | Val | Arg |
| | | | 20 | | | | | 25 | | | | | 30 | | |
| Glu | Leu | Ile | Glu | Glu | Leu | Val | Asn | Ile | Thr | Gln | Asn | Gln | Lys | Ala | Pro |
| | | | | 35 | | | | | 40 | | | | | 45 | |
| Leu | Cys | Asn | Gly | Ser | Met | Val | Trp | Ser | Ile | Asn | Leu | Thr | Ala | Gly | Met |
| | 50 | | | | | 55 | | | | | 60 | | | | |
| Tyr | Cys | Ala | Ala | Leu | Glu | Ser | Leu | Ile | Asn | Val | Ser | Gly | Cys | Ser | Ala |
| 65 | | | | | 70 | | | | | 75 | | | | | 80 |
| Ile | Glu | Lys | Thr | Gln | Arg | Met | Leu | Ser | Gly | Phe | Cys | Pro | His | Lys | Val |
| | | | | 85 | | | | | 90 | | | | | 95 | |
| Ser | Ala | Gly | Gln | Phe | Ser | Ser | Leu | His | Val | Arg | Asp | Thr | Arg | Ile | Glu |
| | | | 100 | | | | | 105 | | | | | 110 | | |
| Val | Ala | Gln | Phe | Val | Lys | Asp | Leu | Leu | Asn | His | Leu | Lys | Glu | Leu | Phe |
| | | | | 115 | | | | | 120 | | | | | 125 | |
| Thr | Glu | Gly | Gln | Phe | Asn | Glu | Ser | Lys | Tyr | Gly | Pro | Pro | Cys | Pro | Pro |
| | 130 | | | | | 135 | | | | | 140 | | | | |
| Cys | Pro | Gly | Gly | Gly | Ser | Ser | Gly | Gly | Ser | Gly | Gly | Gln | Pro | Arg |
| 145 | | | | | 150 | | | | | 155 | | | | | 160 |
| Glu | Pro | Gln | Val | Tyr | Thr | Leu | Pro | Pro | Ser | Gln | Glu | Met | Thr | Lys |
| | | | | 165 | | | | | 170 | | | | | 175 | |
| Asn | Gln | Val | Ser | Leu | Thr | Cys | Leu | Val | Lys | Gly | Phe | Tyr | Pro | Ser | Asp |
| | | | 180 | | | | | 185 | | | | | 190 | | |
| Ile | Ala | Val | Glu | Trp | Glu | Ser | Asn | Gly | Gln | Pro | Glu | Asn | Asn | Tyr | Lys |
| | | | | 195 | | | | | 200 | | | | | 205 | |
| Thr | Thr | Pro | Pro | Val | Leu | Asp | Ser | Asp | Gly | Ser | Phe | Phe | Leu | Tyr | Ser |
| | 210 | | | | | 215 | | | | | 220 | | | | |
| Arg | Leu | Thr | Val | Asp | Lys | Ser | Arg | Trp | Gln | Glu | Gly | Asn | Val | Phe | Ser |
| 225 | | | | | 230 | | | | | 235 | | | | | 240 |
| Cys | Ser | Val | Met | His | Glu | Ala | Leu | His | Asn | His | Tyr | Thr | Gln | Lys | Ser |
| | | | | 245 | | | | | 250 | | | | | 255 | |
| Leu | Ser | Leu | Ser | Leu | Gly | Lys | Met | Ala | Leu | Ile | Val | Leu | Gly | Gly | Val |
| | | | 260 | | | | | 265 | | | | | 270 | | |
| Ala | Gly | Leu | Leu | Leu | Phe | Ile | Gly | Leu | Gly | Ile | Phe | Phe | Lys | Arg | Gly |
| | | | | 275 | | | | | 280 | | | | | 285 | |
| Arg | Lys | Lys | Leu | Leu | Tyr | Ile | Phe | Lys | Gln | Pro | Phe | Met | Arg | Pro | Val |
| | 290 | | | | | 295 | | | | | 300 | | | | |
| Gln | Thr | Thr | Gln | Glu | Glu | Asp | Gly | Cys | Ser | Cys | Arg | Phe | Pro | Glu | Glu |
| 305 | | | | | 310 | | | | | 315 | | | | | 320 |
| Glu | Glu | Gly | Gly | Cys | Glu | Leu | Gly | Gly | Gly | Arg | Val | Lys | Phe | Ser | Arg |
| | | | | 325 | | | | | 330 | | | | | 335 | |
| Ser | Ala | Asp | Ala | Pro | Ala | Tyr | Gln | Gln | Gly | Gln | Asn | Gln | Leu | Tyr | Asn |
| | | | 340 | | | | | 345 | | | | | 350 | | |
| Glu | Leu | Asn | Leu | Gly | Arg | Arg | Glu | Glu | Tyr | Asp | Val | Leu | Asp | Lys | Arg |
| | | | | 355 | | | | | 360 | | | | | 365 | |
| Arg | Gly | Arg | Asp | Pro | Glu | Met | Gly | Gly | Lys | Pro | Arg | Arg | Lys | Asn | Pro |
| | 370 | | | | | 375 | | | | | 380 | | | | |

```
Gln Glu Gly Leu Tyr Asn Glu Leu Gln Lys Asp Lys Met Ala Glu Ala
385                 390                 395                 400

Tyr Ser Glu Ile Gly Met Lys Gly Glu Arg Arg Gly Lys Gly His
            405                 410                 415

Asp Gly Leu Tyr Gln Gly Leu Ser Thr Ala Thr Lys Asp Thr Tyr Asp
            420                 425                 430

Ala Leu His Met Gln Ala Leu Pro Pro Arg Leu Glu Gly Gly Gly Glu
            435                 440                 445

Gly Arg Gly Ser Leu Leu Thr Cys Gly Asp Val Glu Glu Asn Pro Gly
            450                 455                 460

Pro Arg Met Pro Pro Arg Leu Leu Phe Phe Leu Leu Phe Leu Thr
465                 470                 475                 480

Pro Met Glu Val Arg Pro Glu Glu Pro Leu Val Val Lys Val Glu Glu
                485                 490                 495

Gly Asp Asn Ala Val Leu Gln Cys Leu Lys Gly Thr Ser Asp Gly Pro
            500                 505                 510

Thr Gln Gln Leu Thr Trp Ser Arg Glu Ser Pro Leu Lys Pro Phe Leu
            515                 520                 525

Lys Leu Ser Leu Gly Leu Pro Gly Leu Gly Ile His Met Arg Pro Leu
530                 535                 540

Ala Ile Trp Leu Phe Ile Phe Asn Val Ser Gln Gln Met Gly Gly Phe
545                 550                 555                 560

Tyr Leu Cys Gln Pro Gly Pro Pro Ser Glu Lys Ala Trp Gln Pro Gly
                565                 570                 575

Trp Thr Val Asn Val Glu Gly Ser Gly Glu Leu Phe Arg Trp Asn Val
                580                 585                 590

Ser Asp Leu Gly Gly Leu Gly Cys Gly Leu Lys Asn Arg Ser Ser Glu
            595                 600                 605

Gly Pro Ser Ser Pro Ser Gly Lys Leu Met Ser Pro Lys Leu Tyr Val
            610                 615                 620

Trp Ala Lys Asp Arg Pro Glu Ile Trp Glu Gly Glu Pro Pro Cys Val
625                 630                 635                 640

Pro Pro Arg Asp Ser Leu Asn Gln Ser Leu Ser Gln Asp Leu Thr Met
                645                 650                 655

Ala Pro Gly Ser Thr Leu Trp Leu Ser Cys Gly Val Pro Pro Asp Ser
            660                 665                 670

Val Ser Arg Gly Pro Leu Ser Trp Thr His Val His Pro Lys Gly Pro
            675                 680                 685

Lys Ser Leu Leu Ser Leu Glu Leu Lys Asp Asp Arg Pro Ala Arg Asp
            690                 695                 700

Met Trp Val Met Glu Thr Gly Leu Leu Leu Pro Arg Ala Thr Ala Gln
705                 710                 715                 720

Asp Ala Gly Lys Tyr Tyr Cys His Arg Gly Asn Leu Thr Met Ser Phe
                725                 730                 735

His Leu Glu Ile Thr Ala Arg Pro Val Leu Trp His Trp Leu Leu Arg
            740                 745                 750

Thr Gly Gly Trp Lys Val Ser Ala Val Thr Leu Ala Tyr Leu Ile Phe
            755                 760                 765

Cys Leu Cys Ser Leu Val Gly Ile Leu His Leu Gln Arg Ala Leu Val
            770                 775                 780

Leu Arg Arg Lys Arg
785
```

<210> SEQ ID NO 32
<211> LENGTH: 420
<212> TYPE: PRT
<213> ORGANISM: Artificial Sequence
<220> FEATURE:
<223> OTHER INFORMATION: mature IL13(C4)-IgG4(HL-CH3)-CD4tm-41BB-Zeta(CO)

<400> SEQUENCE: 32

```
Gly Pro Val Pro Pro Ser Thr Ala Val Arg Glu Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Arg Ile Glu Val Ala Gln Phe Val Lys
                85                  90                  95

Asp Leu Leu Asn His Leu Lys Glu Leu Phe Thr Gly Gln Phe Asn
            100                 105                 110

Glu Ser Lys Tyr Gly Pro Pro Cys Pro Pro Cys Pro Gly Gly Ser
        115                 120                 125

Ser Gly Gly Gly Ser Gly Gln Pro Arg Glu Pro Gln Val Tyr Thr
    130                 135                 140

Leu Pro Pro Ser Gln Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
                165                 170                 175

Ser Asn Gly Gln Pro Glu Asn Asn Tyr Lys Thr Thr Pro Pro Val Leu
            180                 185                 190

Asp Ser Asp Gly Ser Phe Phe Leu Tyr Ser Arg Leu Thr Val Asp Lys
        195                 200                 205

Ser Arg Trp Gln Glu Gly Asn Val Phe Ser Cys Ser Val Met His Glu
    210                 215                 220

Ala Leu His Asn His Tyr Thr Gln Lys Ser Leu Ser Leu Ser Leu Gly
225                 230                 235                 240

Lys Met Ala Leu Ile Val Leu Gly Gly Val Ala Gly Leu Leu Leu Phe
                245                 250                 255

Ile Gly Leu Gly Ile Phe Phe Lys Arg Gly Arg Lys Lys Leu Leu Tyr
            260                 265                 270

Ile Phe Lys Gln Pro Phe Met Arg Pro Val Gln Thr Thr Gln Glu Glu
        275                 280                 285

Asp Gly Cys Ser Cys Arg Phe Pro Glu Glu Glu Glu Gly Gly Cys Glu
    290                 295                 300

Leu Gly Gly Gly Arg Val Lys Phe Ser Arg Ser Ala Asp Ala Pro Ala
305                 310                 315                 320

Tyr Gln Gln Gly Gln Asn Gln Leu Tyr Asn Glu Leu Asn Leu Gly Arg
                325                 330                 335

Arg Glu Glu Tyr Asp Val Leu Asp Lys Arg Arg Gly Arg Asp Pro Glu
            340                 345                 350

Met Gly Gly Lys Pro Arg Arg Lys Asn Pro Gln Glu Gly Leu Tyr Asn
        355                 360                 365
```

Glu Leu Gln Lys Asp Lys Met Ala Glu Ala Tyr Ser Glu Ile Gly Met
        370                 375                 380

Lys Gly Glu Arg Arg Arg Gly Lys Gly His Asp Gly Leu Tyr Gln Gly
385                 390                 395                 400

Leu Ser Thr Ala Thr Lys Asp Thr Tyr Asp Ala Leu His Met Gln Ala
                405                 410                 415

Leu Pro Pro Arg
            420

<210> SEQ ID NO 33
<211> LENGTH: 442
<212> TYPE: PRT
<213> ORGANISM: Artificial Sequence
<220> FEATURE:
<223> OTHER INFORMATION: IL13(C4)-IgG4(HL-CH3)-CD4tm-41BB-Zeta(CO) with
      a signal sequence

<400> SEQUENCE: 33

Met Leu Leu Leu Val Thr Ser Leu Leu Leu Cys Glu Leu Pro His Pro
1               5                   10                  15

Ala Phe Leu Leu Ile Pro Gly Pro Val Pro Pro Ser Thr Ala Val Arg
                20                  25                  30

Glu Leu Ile Glu Glu Leu Val Asn Ile Thr Gln Asn Gln Lys Ala Pro
            35                  40                  45

Leu Cys Asn Gly Ser Met Val Trp Ser Ile Asn Leu Thr Ala Gly Met
        50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Arg Ile Glu
            100                 105                 110

Val Ala Gln Phe Val Lys Asp Leu Leu Asn His Leu Lys Glu Leu Phe
        115                 120                 125

Thr Glu Gly Gln Phe Asn Glu Ser Lys Tyr Gly Pro Pro Cys Pro Pro
130                 135                 140

Cys Pro Gly Gly Gly Ser Ser Gly Gly Ser Gly Gly Gln Pro Arg
145                 150                 155                 160

Glu Pro Gln Val Tyr Thr Leu Pro Pro Ser Gln Glu Glu Met Thr Lys
                165                 170                 175

Asn Gln Val Ser Leu Thr Cys Leu Val Lys Gly Phe Tyr Pro Ser Asp
            180                 185                 190

Ile Ala Val Glu Trp Glu Ser Asn Gly Gln Pro Glu Asn Asn Tyr Lys
        195                 200                 205

Thr Thr Pro Pro Val Leu Asp Ser Asp Gly Ser Phe Phe Leu Tyr Ser
210                 215                 220

Arg Leu Thr Val Asp Lys Ser Arg Trp Gln Glu Gly Asn Val Phe Ser
225                 230                 235                 240

Cys Ser Val Met His Glu Ala Leu His Asn His Tyr Thr Gln Lys Ser
                245                 250                 255

Leu Ser Leu Ser Leu Gly Lys Met Ala Leu Ile Val Leu Gly Gly Val
            260                 265                 270

Ala Gly Leu Leu Leu Phe Ile Gly Leu Gly Ile Phe Phe Lys Arg Gly
        275                 280                 285

Arg Lys Lys Leu Leu Tyr Ile Phe Lys Gln Pro Phe Met Arg Pro Val

```
            290                 295                 300
Gln Thr Thr Gln Glu Glu Asp Gly Cys Ser Cys Arg Phe Pro Glu Glu
305                 310                 315                 320

Glu Glu Gly Gly Cys Glu Leu Gly Gly Gly Arg Val Lys Phe Ser Arg
                325                 330                 335

Ser Ala Asp Ala Pro Ala Tyr Gln Gln Gly Gln Asn Gln Leu Tyr Asn
            340                 345                 350

Glu Leu Asn Leu Gly Arg Arg Glu Glu Tyr Asp Val Leu Asp Lys Arg
                355                 360                 365

Arg Gly Arg Asp Pro Glu Met Gly Gly Lys Pro Arg Arg Lys Asn Pro
        370                 375                 380

Gln Glu Gly Leu Tyr Asn Glu Leu Gln Lys Asp Lys Met Ala Glu Ala
385                 390                 395                 400

Tyr Ser Glu Ile Gly Met Lys Gly Glu Arg Arg Arg Gly Lys Gly His
                    405                 410                 415

Asp Gly Leu Tyr Gln Gly Leu Ser Thr Ala Thr Lys Asp Thr Tyr Asp
                420                 425                 430

Ala Leu His Met Gln Ala Leu Pro Pro Arg
            435                 440
```

<210> SEQ ID NO 34
<211> LENGTH: 894
<212> TYPE: PRT
<213> ORGANISM: Artificial Sequence
<220> FEATURE:
<223> OTHER INFORMATION: IL13(D7)-IgG4(L235E,N297Q)-CD28gg-Zeta(CO)-T2A-CD19t

<400> SEQUENCE: 34

```
Met Leu Leu Leu Val Thr Ser Leu Leu Leu Cys Glu Leu Pro His Pro
1               5                   10                  15

Ala Phe Leu Leu Ile Pro Gly Pro Val Pro Pro Ser Thr Ala Ala Arg
                20                  25                  30

Glu Leu Ile Glu Glu Leu Phe Asn Ile Thr Gln Asn Gln Lys Ala Pro
            35                  40                  45

Leu Cys Asn Gly Ser Met Val Trp Ser Ile Asn Leu Thr Ala Gly Met
50                  55                  60

Tyr Cys Ala Ala Leu Glu Ser Leu Ile Asn Val Ser Gly Cys Ser Ala
65                  70                  75                  80

Ile Glu Lys Thr Lys Arg Met Leu Ser Gly Phe Cys Pro His Lys Val
                85                  90                  95

Ser Ala Gly Gln Phe Pro Ser Leu His Val Lys Lys Thr Arg Ile Glu
            100                 105                 110

Val Ala Gln Phe Val Lys Asp Leu Leu Ile His Leu Arg Lys Leu Phe
        115                 120                 125

Lys Glu Gly Gln Phe Asn Glu Ser Lys Tyr Gly Pro Pro Cys Pro Pro
130                 135                 140

Cys Pro Ala Pro Glu Phe Glu Gly Gly Pro Ser Val Phe Leu Phe Pro
145                 150                 155                 160

Pro Lys Pro Lys Asp Thr Leu Met Ile Ser Arg Thr Pro Glu Val Thr
                165                 170                 175

Cys Val Val Val Asp Val Ser Gln Glu Asp Pro Glu Val Gln Phe Asn
            180                 185                 190

Trp Tyr Val Asp Gly Val Glu Val His Asn Ala Lys Thr Lys Pro Arg
        195                 200                 205
```

Glu Glu Gln Phe Gln Ser Thr Tyr Arg Val Val Ser Val Leu Thr Val
210                 215                 220

Leu His Gln Asp Trp Leu Asn Gly Lys Glu Tyr Lys Cys Lys Val Ser
225                 230                 235                 240

Asn Lys Gly Leu Pro Ser Ser Ile Glu Lys Thr Ile Ser Lys Ala Lys
            245                 250                 255

Gly Gln Pro Arg Glu Pro Gln Val Tyr Thr Leu Pro Pro Ser Gln Glu
            260                 265                 270

Glu Met Thr Lys Asn Gln Val Ser Leu Thr Cys Leu Val Lys Gly Phe
        275                 280                 285

Tyr Pro Ser Asp Ile Ala Val Glu Trp Glu Ser Asn Gly Gln Pro Glu
        290                 295                 300

Asn Asn Tyr Lys Thr Thr Pro Pro Val Leu Asp Ser Asp Gly Ser Phe
305                 310                 315                 320

Phe Leu Tyr Ser Arg Leu Thr Val Asp Lys Ser Arg Trp Gln Glu Gly
                325                 330                 335

Asn Val Phe Ser Cys Ser Val Met His Glu Ala Leu His Asn His Tyr
            340                 345                 350

Thr Gln Lys Ser Leu Ser Leu Ser Leu Gly Lys Met Phe Trp Val Leu
        355                 360                 365

Val Val Val Gly Gly Val Leu Ala Cys Tyr Ser Leu Leu Val Thr Val
370                 375                 380

Ala Phe Ile Ile Phe Trp Val Arg Ser Lys Arg Ser Arg Gly Gly His
385                 390                 395                 400

Ser Asp Tyr Met Asn Met Thr Pro Arg Arg Pro Gly Pro Thr Arg Lys
                405                 410                 415

His Tyr Gln Pro Tyr Ala Pro Pro Arg Asp Phe Ala Ala Tyr Arg Ser
            420                 425                 430

Gly Gly Gly Arg Val Lys Phe Ser Arg Ser Ala Asp Ala Pro Ala Tyr
        435                 440                 445

Gln Gln Gly Gln Asn Gln Leu Tyr Asn Glu Leu Asn Leu Gly Arg Arg
450                 455                 460

Glu Glu Tyr Asp Val Leu Asp Lys Arg Arg Gly Arg Asp Pro Glu Met
465                 470                 475                 480

Gly Gly Lys Pro Arg Arg Lys Asn Pro Gln Glu Gly Leu Tyr Asn Glu
                485                 490                 495

Leu Gln Lys Asp Lys Met Ala Glu Ala Tyr Ser Glu Ile Gly Met Lys
            500                 505                 510

Gly Glu Arg Arg Arg Gly Lys Gly His Asp Gly Leu Tyr Gln Gly Leu
        515                 520                 525

Ser Thr Ala Thr Lys Asp Thr Tyr Asp Ala Leu His Met Gln Ala Leu
530                 535                 540

Pro Pro Arg Leu Glu Gly Gly Gly Glu Gly Arg Gly Ser Leu Leu Thr
545                 550                 555                 560

Cys Gly Asp Val Glu Glu Asn Pro Gly Pro Arg Met Pro Pro Pro Arg
                565                 570                 575

Leu Leu Phe Phe Leu Leu Phe Leu Thr Pro Met Glu Val Arg Pro Glu
            580                 585                 590

Glu Pro Leu Val Val Lys Val Glu Gly Asp Asn Ala Val Leu Gln
        595                 600                 605

Cys Leu Lys Gly Thr Ser Asp Gly Pro Thr Gln Gln Leu Thr Trp Ser
610                 615                 620

Arg Glu Ser Pro Leu Lys Pro Phe Leu Lys Leu Ser Leu Gly Leu Pro

-continued

```
                625                 630                 635                 640
        Gly Leu Gly Ile His Met Arg Pro Leu Ala Ile Trp Leu Phe Ile Phe
                        645                 650                 655

Asn Val Ser Gln Gln Met Gly Gly Phe Tyr Leu Cys Gln Pro Gly Pro
                        660                 665                 670

Pro Ser Glu Lys Ala Trp Gln Pro Gly Trp Thr Val Asn Val Glu Gly
                        675                 680                 685

Ser Gly Glu Leu Phe Arg Trp Asn Val Ser Asp Leu Gly Gly Leu Gly
                        690                 695                 700

Cys Gly Leu Lys Asn Arg Ser Ser Glu Gly Pro Ser Ser Pro Ser Gly
        705                 710                 715                 720

Lys Leu Met Ser Pro Lys Leu Tyr Val Trp Ala Lys Asp Arg Pro Glu
                        725                 730                 735

Ile Trp Glu Gly Glu Pro Pro Cys Val Pro Pro Arg Asp Ser Leu Asn
                        740                 745                 750

Gln Ser Leu Ser Gln Asp Leu Thr Met Ala Pro Gly Ser Thr Leu Trp
                        755                 760                 765

Leu Ser Cys Gly Val Pro Pro Asp Ser Val Ser Arg Gly Pro Leu Ser
                        770                 775                 780

Trp Thr His Val His Pro Lys Gly Pro Lys Ser Leu Leu Ser Leu Glu
        785                 790                 795                 800

Leu Lys Asp Asp Arg Pro Ala Arg Asp Met Trp Val Met Glu Thr Gly
                        805                 810                 815

Leu Leu Leu Pro Arg Ala Thr Ala Gln Asp Ala Gly Lys Tyr Tyr Cys
                        820                 825                 830

His Arg Gly Asn Leu Thr Met Ser Phe His Leu Glu Ile Thr Ala Arg
                        835                 840                 845

Pro Val Leu Trp His Trp Leu Leu Arg Thr Gly Gly Trp Lys Val Ser
                        850                 855                 860

Ala Val Thr Leu Ala Tyr Leu Ile Phe Cys Leu Cys Ser Leu Val Gly
        865                 870                 875                 880

Ile Leu His Leu Gln Arg Ala Leu Val Leu Arg Arg Lys Arg
                        885                 890

<210> SEQ ID NO 35
<211> LENGTH: 525
<212> TYPE: PRT
<213> ORGANISM: Artificial Sequence
<220> FEATURE:
<223> OTHER INFORMATION: mature IL13(D7)-IgG4(L235E,N297Q)-CD28gg-
      Zeta(CO)

<400> SEQUENCE: 35

Gly Pro Val Pro Pro Ser Thr Ala Ala Arg Glu Leu Ile Glu Glu Leu
        1               5                   10                  15

Phe Asn Ile Thr Gln Asn Gln Lys Ala Pro Leu Cys Asn Gly Ser Met
                        20                  25                  30

Val Trp Ser Ile Asn Leu Thr Ala Gly Met Tyr Cys Ala Ala Leu Glu
                        35                  40                  45

Ser Leu Ile Asn Val Ser Gly Cys Ser Ala Ile Glu Lys Thr Lys Arg
                50                  55                  60

Met Leu Ser Gly Phe Cys Pro His Lys Val Ser Ala Gly Gln Phe Pro
        65                  70                  75                  80

Ser Leu His Val Lys Lys Thr Arg Ile Glu Val Ala Gln Phe Val Lys
                        85                  90                  95
```

-continued

```
Asp Leu Leu Ile His Leu Arg Lys Leu Phe Lys Glu Gly Gln Phe Asn
            100                 105                 110
Glu Ser Lys Tyr Gly Pro Pro Cys Pro Pro Cys Pro Ala Pro Glu Phe
        115                 120                 125
Glu Gly Gly Pro Ser Val Phe Leu Phe Pro Pro Lys Pro Lys Asp Thr
    130                 135                 140
Leu Met Ile Ser Arg Thr Pro Glu Val Thr Cys Val Val Val Asp Val
145                 150                 155                 160
Ser Gln Glu Asp Pro Glu Val Gln Phe Asn Trp Tyr Val Asp Gly Val
                165                 170                 175
Glu Val His Asn Ala Lys Thr Lys Pro Arg Glu Glu Gln Phe Gln Ser
            180                 185                 190
Thr Tyr Arg Val Val Ser Val Leu Thr Val Leu His Gln Asp Trp Leu
        195                 200                 205
Asn Gly Lys Glu Tyr Lys Cys Lys Val Ser Asn Lys Gly Leu Pro Ser
    210                 215                 220
Ser Ile Glu Lys Thr Ile Ser Lys Ala Lys Gly Gln Pro Arg Glu Pro
225                 230                 235                 240
Gln Val Tyr Thr Leu Pro Pro Ser Gln Glu Glu Met Thr Lys Asn Gln
                245                 250                 255
Val Ser Leu Thr Cys Leu Val Lys Gly Phe Tyr Pro Ser Asp Ile Ala
            260                 265                 270
Val Glu Trp Glu Ser Asn Gly Gln Pro Glu Asn Asn Tyr Lys Thr Thr
        275                 280                 285
Pro Pro Val Leu Asp Ser Asp Gly Ser Phe Phe Leu Tyr Ser Arg Leu
    290                 295                 300
Thr Val Asp Lys Ser Arg Trp Gln Glu Gly Asn Val Phe Ser Cys Ser
305                 310                 315                 320
Val Met His Glu Ala Leu His Asn His Tyr Thr Gln Lys Ser Leu Ser
                325                 330                 335
Leu Ser Leu Gly Lys Met Phe Trp Val Leu Val Val Val Gly Gly Val
            340                 345                 350
Leu Ala Cys Tyr Ser Leu Leu Val Thr Val Ala Phe Ile Ile Phe Trp
        355                 360                 365
Val Arg Ser Lys Arg Ser Arg Gly Gly His Ser Asp Tyr Met Asn Met
    370                 375                 380
Thr Pro Arg Arg Pro Gly Pro Thr Arg Lys His Tyr Gln Pro Tyr Ala
385                 390                 395                 400
Pro Pro Arg Asp Phe Ala Ala Tyr Arg Ser Gly Gly Gly Arg Val Lys
                405                 410                 415
Phe Ser Arg Ser Ala Asp Ala Pro Ala Tyr Gln Gln Gly Gln Asn Gln
            420                 425                 430
Leu Tyr Asn Glu Leu Asn Leu Gly Arg Arg Glu Glu Tyr Asp Val Leu
        435                 440                 445
Asp Lys Arg Arg Gly Arg Asp Pro Glu Met Gly Gly Lys Pro Arg Arg
    450                 455                 460
Lys Asn Pro Gln Glu Gly Leu Tyr Asn Glu Leu Gln Lys Asp Lys Met
465                 470                 475                 480
Ala Glu Ala Tyr Ser Glu Ile Gly Met Lys Gly Glu Arg Arg Arg Gly
                485                 490                 495
Lys Gly His Asp Gly Leu Tyr Gln Gly Leu Ser Thr Ala Thr Lys Asp
            500                 505                 510
Thr Tyr Asp Ala Leu His Met Gln Ala Leu Pro Pro Arg
```

<210> SEQ ID NO 36
<211> LENGTH: 547
<212> TYPE: PRT
<213> ORGANISM: Artificial Sequence
<220> FEATURE:
<223> OTHER INFORMATION: IL13(D7)-IgG4(L235E,N297Q)-CD28gg-Zeta(CO) with a signal sequence

<400> SEQUENCE: 36

```
Met Leu Leu Leu Val Thr Ser Leu Leu Leu Cys Glu Leu Pro His Pro
1               5                   10                  15

Ala Phe Leu Leu Ile Pro Gly Pro Val Pro Pro Ser Thr Ala Ala Arg
            20                  25                  30

Glu Leu Ile Glu Glu Leu Phe Asn Ile Thr Gln Asn Gln Lys Ala Pro
        35                  40                  45

Leu Cys Asn Gly Ser Met Val Trp Ser Ile Asn Leu Thr Ala Gly Met
    50                  55                  60

Tyr Cys Ala Ala Leu Glu Ser Leu Ile Asn Val Ser Gly Cys Ser Ala
65                  70                  75                  80

Ile Glu Lys Thr Lys Arg Met Leu Ser Gly Phe Cys Pro His Lys Val
                85                  90                  95

Ser Ala Gly Gln Phe Pro Ser Leu His Val Lys Lys Thr Arg Ile Glu
            100                 105                 110

Val Ala Gln Phe Val Lys Asp Leu Leu Ile His Leu Arg Lys Leu Phe
        115                 120                 125

Lys Glu Gly Gln Phe Asn Glu Ser Lys Tyr Gly Pro Pro Cys Pro Pro
    130                 135                 140

Cys Pro Ala Pro Glu Phe Glu Gly Gly Pro Ser Val Phe Leu Phe Pro
145                 150                 155                 160

Pro Lys Pro Lys Asp Thr Leu Met Ile Ser Arg Thr Pro Glu Val Thr
                165                 170                 175

Cys Val Val Val Asp Val Ser Gln Glu Asp Pro Glu Val Gln Phe Asn
            180                 185                 190

Trp Tyr Val Asp Gly Val Glu Val His Asn Ala Lys Thr Lys Pro Arg
        195                 200                 205

Glu Glu Gln Phe Gln Ser Thr Tyr Arg Val Val Ser Val Leu Thr Val
    210                 215                 220

Leu His Gln Asp Trp Leu Asn Gly Lys Glu Tyr Lys Cys Lys Val Ser
225                 230                 235                 240

Asn Lys Gly Leu Pro Ser Ser Ile Glu Lys Thr Ile Ser Lys Ala Lys
                245                 250                 255

Gly Gln Pro Arg Glu Pro Gln Val Tyr Thr Leu Pro Pro Ser Gln Glu
            260                 265                 270

Glu Met Thr Lys Asn Gln Val Ser Leu Thr Cys Leu Val Lys Gly Phe
        275                 280                 285

Tyr Pro Ser Asp Ile Ala Val Glu Trp Glu Ser Asn Gly Gln Pro Glu
    290                 295                 300

Asn Asn Tyr Lys Thr Thr Pro Pro Val Leu Asp Ser Asp Gly Ser Phe
305                 310                 315                 320

Phe Leu Tyr Ser Arg Leu Thr Val Asp Lys Ser Arg Trp Gln Glu Gly
                325                 330                 335

Asn Val Phe Ser Cys Ser Val Met His Glu Ala Leu His Asn His Tyr
            340                 345                 350
```

```
Thr Gln Lys Ser Leu Ser Leu Ser Leu Gly Lys Met Phe Trp Val Leu
            355                 360                 365
Val Val Val Gly Gly Val Leu Ala Cys Tyr Ser Leu Leu Val Thr Val
    370                 375                 380
Ala Phe Ile Ile Phe Trp Val Arg Ser Lys Arg Ser Arg Gly Gly His
385                 390                 395                 400
Ser Asp Tyr Met Asn Met Thr Pro Arg Arg Pro Gly Pro Thr Arg Lys
            405                 410                 415
His Tyr Gln Pro Tyr Ala Pro Pro Arg Asp Phe Ala Ala Tyr Arg Ser
        420                 425                 430
Gly Gly Gly Arg Val Lys Phe Ser Arg Ser Ala Asp Ala Pro Ala Tyr
        435                 440                 445
Gln Gln Gly Gln Asn Gln Leu Tyr Asn Glu Leu Asn Leu Gly Arg Arg
        450                 455                 460
Glu Glu Tyr Asp Val Leu Asp Lys Arg Arg Gly Arg Asp Pro Glu Met
465                 470                 475                 480
Gly Gly Lys Pro Arg Arg Lys Asn Pro Gln Glu Gly Leu Tyr Asn Glu
            485                 490                 495
Leu Gln Lys Asp Lys Met Ala Glu Ala Tyr Ser Glu Ile Gly Met Lys
            500                 505                 510
Gly Glu Arg Arg Arg Gly Lys Gly His Asp Gly Leu Tyr Gln Gly Leu
        515                 520                 525
Ser Thr Ala Thr Lys Asp Thr Tyr Asp Ala Leu His Met Gln Ala Leu
        530                 535                 540
Pro Pro Arg
545

<210> SEQ ID NO 37
<211> LENGTH: 789
<212> TYPE: PRT
<213> ORGANISM: Artificial Sequence
<220> FEATURE:
<223> OTHER INFORMATION: IL13(D7)-IgG4(HL-CH3)-CD4tm-41BB-Zeta(CO)-T2A-
      CD19t (BspEI)

<400> SEQUENCE: 37

Met Leu Leu Leu Val Thr Ser Leu Leu Leu Cys Glu Leu Pro His Pro
1               5                   10                  15
Ala Phe Leu Leu Ile Pro Gly Pro Val Pro Pro Ser Thr Ala Ala Arg
            20                  25                  30
Glu Leu Ile Glu Glu Leu Phe Asn Ile Thr Gln Asn Gln Lys Ala Pro
        35                  40                  45
Leu Cys Asn Gly Ser Met Val Trp Ser Ile Asn Leu Thr Ala Gly Met
    50                  55                  60
Tyr Cys Ala Ala Leu Glu Ser Leu Ile Asn Val Ser Gly Cys Ser Ala
65                  70                  75                  80
Ile Glu Lys Thr Lys Arg Met Leu Ser Gly Phe Cys Pro His Lys Val
                85                  90                  95
Ser Ala Gly Gln Phe Pro Ser Leu His Val Lys Lys Thr Arg Ile Glu
            100                 105                 110
Val Ala Gln Phe Val Lys Asp Leu Leu Ile His Leu Arg Lys Leu Phe
        115                 120                 125
Lys Glu Gly Gln Phe Asn Glu Ser Lys Tyr Gly Pro Pro Cys Pro Pro
    130                 135                 140
Cys Pro Gly Gly Gly Ser Ser Gly Gly Gly Ser Gly Gln Pro Arg
145                 150                 155                 160
```

-continued

Glu Pro Gln Val Tyr Thr Leu Pro Pro Ser Gln Glu Met Thr Lys
              165                 170                 175

Asn Gln Val Ser Leu Thr Cys Leu Val Lys Gly Phe Tyr Pro Ser Asp
              180                 185                 190

Ile Ala Val Glu Trp Glu Ser Asn Gly Gln Pro Glu Asn Asn Tyr Lys
              195                 200                 205

Thr Thr Pro Pro Val Leu Asp Ser Asp Gly Ser Phe Phe Leu Tyr Ser
      210                 215                 220

Arg Leu Thr Val Asp Lys Ser Arg Trp Gln Glu Gly Asn Val Phe Ser
225                 230                 235                 240

Cys Ser Val Met His Glu Ala Leu His Asn His Tyr Thr Gln Lys Ser
              245                 250                 255

Leu Ser Leu Ser Leu Gly Lys Met Ala Leu Ile Val Leu Gly Gly Val
              260                 265                 270

Ala Gly Leu Leu Leu Phe Ile Gly Leu Gly Ile Phe Phe Lys Arg Gly
              275                 280                 285

Arg Lys Lys Leu Leu Tyr Ile Phe Lys Gln Pro Phe Met Arg Pro Val
              290                 295                 300

Gln Thr Thr Gln Glu Glu Asp Gly Cys Ser Cys Arg Phe Pro Glu Glu
305                 310                 315                 320

Glu Glu Gly Gly Cys Glu Leu Gly Gly Gly Arg Val Lys Phe Ser Arg
              325                 330                 335

Ser Ala Asp Ala Pro Ala Tyr Gln Gln Gly Gln Asn Gln Leu Tyr Asn
              340                 345                 350

Glu Leu Asn Leu Gly Arg Arg Glu Glu Tyr Asp Val Leu Asp Lys Arg
              355                 360                 365

Arg Gly Arg Asp Pro Glu Met Gly Gly Lys Pro Arg Arg Lys Asn Pro
              370                 375                 380

Gln Glu Gly Leu Tyr Asn Glu Leu Gln Lys Asp Lys Met Ala Glu Ala
385                 390                 395                 400

Tyr Ser Glu Ile Gly Met Lys Gly Glu Arg Arg Arg Gly Lys Gly His
              405                 410                 415

Asp Gly Leu Tyr Gln Gly Leu Ser Thr Ala Thr Lys Asp Thr Tyr Asp
              420                 425                 430

Ala Leu His Met Gln Ala Leu Pro Pro Arg Leu Glu Gly Gly Gly Glu
              435                 440                 445

Gly Arg Gly Ser Leu Leu Thr Cys Gly Asp Val Glu Glu Asn Pro Gly
              450                 455                 460

Pro Arg Met Pro Pro Arg Leu Leu Phe Phe Leu Leu Phe Leu Thr
465                 470                 475                 480

Pro Met Glu Val Arg Pro Glu Glu Pro Leu Val Val Lys Val Glu Glu
              485                 490                 495

Gly Asp Asn Ala Val Leu Gln Cys Leu Lys Gly Thr Ser Asp Gly Pro
              500                 505                 510

Thr Gln Gln Leu Thr Trp Ser Arg Glu Ser Pro Leu Lys Pro Phe Leu
              515                 520                 525

Lys Leu Ser Leu Gly Leu Pro Gly Leu Gly Ile His Met Arg Pro Leu
              530                 535                 540

Ala Ile Trp Leu Phe Ile Phe Asn Val Ser Gln Gln Met Gly Gly Phe
545                 550                 555                 560

Tyr Leu Cys Gln Pro Gly Pro Pro Ser Glu Lys Ala Trp Gln Pro Gly
              565                 570                 575

```
Trp Thr Val Asn Val Glu Gly Ser Gly Glu Leu Phe Arg Trp Asn Val
            580                 585                 590
Ser Asp Leu Gly Gly Leu Gly Cys Gly Leu Lys Asn Arg Ser Ser Glu
        595                 600                 605
Gly Pro Ser Ser Pro Ser Gly Lys Leu Met Ser Pro Lys Leu Tyr Val
    610                 615                 620
Trp Ala Lys Asp Arg Pro Glu Ile Trp Glu Gly Glu Pro Pro Cys Val
625                 630                 635                 640
Pro Pro Arg Asp Ser Leu Asn Gln Ser Leu Ser Gln Asp Leu Thr Met
            645                 650                 655
Ala Pro Gly Ser Thr Leu Trp Leu Ser Cys Gly Val Pro Pro Asp Ser
        660                 665                 670
Val Ser Arg Gly Pro Leu Ser Trp Thr His Val His Pro Lys Gly Pro
    675                 680                 685
Lys Ser Leu Leu Ser Leu Glu Leu Lys Asp Asp Arg Pro Ala Arg Asp
690                 695                 700
Met Trp Val Met Glu Thr Gly Leu Leu Leu Pro Arg Ala Thr Ala Gln
705                 710                 715                 720
Asp Ala Gly Lys Tyr Tyr Cys His Arg Gly Asn Leu Thr Met Ser Phe
            725                 730                 735
His Leu Glu Ile Thr Ala Arg Pro Val Leu Trp His Trp Leu Leu Arg
        740                 745                 750
Thr Gly Gly Trp Lys Val Ser Ala Val Thr Leu Ala Tyr Leu Ile Phe
    755                 760                 765
Cys Leu Cys Ser Leu Val Gly Ile Leu His Leu Gln Arg Ala Leu Val
770                 775                 780
Leu Arg Arg Lys Arg
785

<210> SEQ ID NO 38
<211> LENGTH: 420
<212> TYPE: PRT
<213> ORGANISM: Artificial Sequence
<220> FEATURE:
<223> OTHER INFORMATION: mature IL13(D7)-IgG4(HL-CH3)-CD4tm-41BB-
      Zeta(CO)

<400> SEQUENCE: 38

Gly Pro Val Pro Pro Ser Thr Ala Ala Arg Glu Leu Ile Glu Glu Leu
1               5                   10                  15
Phe Asn Ile Thr Gln Asn Gln Lys Ala Pro Leu Cys Asn Gly Ser Met
            20                  25                  30
Val Trp Ser Ile Asn Leu Thr Ala Gly Met Tyr Cys Ala Ala Leu Glu
        35                  40                  45
Ser Leu Ile Asn Val Ser Gly Cys Ser Ala Ile Glu Lys Thr Lys Arg
    50                  55                  60
Met Leu Ser Gly Phe Cys Pro His Lys Val Ser Ala Gly Gln Phe Pro
65                  70                  75                  80
Ser Leu His Val Lys Lys Thr Arg Ile Glu Val Ala Gln Phe Val Lys
            85                  90                  95
Asp Leu Leu Ile His Leu Arg Lys Leu Phe Lys Glu Gly Gln Phe Asn
        100                 105                 110
Glu Ser Lys Tyr Gly Pro Pro Cys Pro Pro Cys Pro Gly Gly Gly Ser
    115                 120                 125
Ser Gly Gly Gly Ser Gly Gly Gln Pro Arg Glu Pro Gln Val Tyr Thr
130                 135                 140
```

Leu Pro Pro Ser Gln Glu Glu Met Thr Lys Asn Gln Val Ser Leu Thr
145                 150                 155                 160

Cys Leu Val Lys Gly Phe Tyr Pro Ser Asp Ile Ala Val Glu Trp Glu
            165                 170                 175

Ser Asn Gly Gln Pro Glu Asn Asn Tyr Lys Thr Thr Pro Pro Val Leu
        180                 185                 190

Asp Ser Asp Gly Ser Phe Phe Leu Tyr Ser Arg Leu Thr Val Asp Lys
    195                 200                 205

Ser Arg Trp Gln Glu Gly Asn Val Phe Ser Cys Ser Val Met His Glu
210                 215                 220

Ala Leu His Asn His Tyr Thr Gln Lys Ser Leu Ser Leu Ser Leu Gly
225                 230                 235                 240

Lys Met Ala Leu Ile Val Leu Gly Gly Val Ala Gly Leu Leu Leu Phe
                245                 250                 255

Ile Gly Leu Gly Ile Phe Phe Lys Arg Gly Arg Lys Lys Leu Leu Tyr
            260                 265                 270

Ile Phe Lys Gln Pro Phe Met Arg Pro Val Gln Thr Thr Gln Glu Glu
        275                 280                 285

Asp Gly Cys Ser Cys Arg Phe Pro Glu Glu Glu Glu Gly Gly Cys Glu
    290                 295                 300

Leu Gly Gly Gly Arg Val Lys Phe Ser Arg Ser Ala Asp Ala Pro Ala
305                 310                 315                 320

Tyr Gln Gln Gly Gln Asn Gln Leu Tyr Asn Glu Leu Asn Leu Gly Arg
                325                 330                 335

Arg Glu Glu Tyr Asp Val Leu Asp Lys Arg Arg Gly Arg Asp Pro Glu
            340                 345                 350

Met Gly Gly Lys Pro Arg Arg Lys Asn Pro Gln Glu Gly Leu Tyr Asn
        355                 360                 365

Glu Leu Gln Lys Asp Lys Met Ala Glu Ala Tyr Ser Glu Ile Gly Met
370                 375                 380

Lys Gly Glu Arg Arg Arg Gly Lys Gly His Asp Gly Leu Tyr Gln Gly
385                 390                 395                 400

Leu Ser Thr Ala Thr Lys Asp Thr Tyr Asp Ala Leu His Met Gln Ala
                405                 410                 415

Leu Pro Pro Arg
            420

<210> SEQ ID NO 39
<211> LENGTH: 442
<212> TYPE: PRT
<213> ORGANISM: Artificial Sequence
<220> FEATURE:
<223> OTHER INFORMATION: IL13(D7)-IgG4(HL-CH3)-CD4tm-41BB-Zeta(CO) with
      a signal sequence

<400> SEQUENCE: 39

Met Leu Leu Leu Val Thr Ser Leu Leu Leu Cys Glu Leu Pro His Pro
1               5                   10                  15

Ala Phe Leu Leu Ile Pro Gly Pro Val Pro Pro Ser Thr Ala Ala Arg
            20                  25                  30

Glu Leu Ile Glu Glu Leu Phe Asn Ile Thr Gln Asn Gln Lys Ala Pro
        35                  40                  45

Leu Cys Asn Gly Ser Met Val Trp Ser Ile Asn Leu Thr Ala Gly Met
    50                  55                  60

Tyr Cys Ala Ala Leu Glu Ser Leu Ile Asn Val Ser Gly Cys Ser Ala

```
                65                  70                  75                  80
Ile Glu Lys Thr Lys Arg Met Leu Ser Gly Phe Cys Pro His Lys Val
                    85                  90                  95

Ser Ala Gly Gln Phe Pro Ser Leu His Val Lys Lys Thr Arg Ile Glu
                    100                 105                 110

Val Ala Gln Phe Val Lys Asp Leu Leu Ile His Leu Arg Lys Leu Phe
                    115                 120                 125

Lys Glu Gly Gln Phe Asn Glu Ser Lys Tyr Gly Pro Pro Cys Pro Pro
                    130                 135                 140

Cys Pro Gly Gly Gly Ser Ser Gly Gly Ser Gly Gly Gln Pro Arg
145                 150                 155                 160

Glu Pro Gln Val Tyr Thr Leu Pro Pro Ser Gln Glu Met Thr Lys
                    165                 170                 175

Asn Gln Val Ser Leu Thr Cys Leu Val Lys Gly Phe Tyr Pro Ser Asp
                    180                 185                 190

Ile Ala Val Glu Trp Glu Ser Asn Gly Gln Pro Glu Asn Asn Tyr Lys
                    195                 200                 205

Thr Thr Pro Pro Val Leu Asp Ser Asp Gly Ser Phe Phe Leu Tyr Ser
        210                 215                 220

Arg Leu Thr Val Asp Lys Ser Arg Trp Gln Glu Gly Asn Val Phe Ser
225                 230                 235                 240

Cys Ser Val Met His Glu Ala Leu His Asn His Tyr Thr Gln Lys Ser
                    245                 250                 255

Leu Ser Leu Ser Leu Gly Lys Met Ala Leu Ile Val Leu Gly Gly Val
                    260                 265                 270

Ala Gly Leu Leu Leu Phe Ile Gly Leu Gly Ile Phe Phe Lys Arg Gly
                    275                 280                 285

Arg Lys Lys Leu Leu Tyr Ile Phe Lys Gln Pro Phe Met Arg Pro Val
                    290                 295                 300

Gln Thr Thr Gln Glu Glu Asp Gly Cys Ser Cys Arg Phe Pro Glu Glu
305                 310                 315                 320

Glu Glu Gly Gly Cys Glu Leu Gly Gly Gly Arg Val Lys Phe Ser Arg
                    325                 330                 335

Ser Ala Asp Ala Pro Ala Tyr Gln Gln Gly Gln Asn Gln Leu Tyr Asn
                    340                 345                 350

Glu Leu Asn Leu Gly Arg Arg Glu Glu Tyr Asp Val Leu Asp Lys Arg
                    355                 360                 365

Arg Gly Arg Asp Pro Glu Met Gly Gly Lys Pro Arg Arg Lys Asn Pro
            370                 375                 380

Gln Glu Gly Leu Tyr Asn Glu Leu Gln Lys Asp Lys Met Ala Glu Ala
385                 390                 395                 400

Tyr Ser Glu Ile Gly Met Lys Gly Glu Arg Arg Arg Gly Lys Gly His
                    405                 410                 415

Asp Gly Leu Tyr Gln Gly Leu Ser Thr Ala Thr Lys Asp Thr Tyr Asp
                    420                 425                 430

Ala Leu His Met Gln Ala Leu Pro Pro Arg
            435                 440

<210> SEQ ID NO 40
<211> LENGTH: 24
<212> TYPE: PRT
<213> ORGANISM: Artificial Sequence
<220> FEATURE:
<223> OTHER INFORMATION: ribosomal skip sequence
```

-continued

```
<400> SEQUENCE: 40

Leu Glu Gly Gly Gly Glu Gly Arg Gly Ser Leu Leu Thr Cys Gly Asp
1               5                   10                  15

Val Glu Glu Asn Pro Gly Pro Arg
                20

<210> SEQ ID NO 41
<211> LENGTH: 354
<212> TYPE: PRT
<213> ORGANISM: Artificial Sequence
<220> FEATURE:
<223> OTHER INFORMATION: truncated EGFR

<400> SEQUENCE: 41

Leu Val Thr Ser Leu Leu Leu Cys Glu Leu Pro His Pro Ala Phe Leu
1               5                   10                  15

Leu Ile Pro Arg Lys Val Cys Asn Gly Ile Gly Ile Gly Glu Phe Lys
                20                  25                  30

Asp Ser Leu Ser Ile Asn Ala Thr Asn Ile Lys His Phe Lys Asn Cys
            35                  40                  45

Thr Ser Ile Ser Gly Asp Leu His Ile Leu Pro Val Ala Phe Arg Gly
    50                  55                  60

Asp Ser Phe Thr His Thr Pro Pro Leu Asp Pro Gln Glu Leu Asp Ile
65                  70                  75                  80

Leu Lys Thr Val Lys Glu Ile Thr Gly Phe Leu Leu Ile Gln Ala Trp
                85                  90                  95

Pro Glu Asn Arg Thr Asp Leu His Ala Phe Glu Asn Leu Glu Ile Ile
                100                 105                 110

Arg Gly Arg Thr Lys Gln His Gly Gln Phe Ser Leu Ala Val Val Ser
            115                 120                 125

Leu Asn Ile Thr Ser Leu Gly Leu Arg Ser Leu Lys Glu Ile Ser Asp
    130                 135                 140

Gly Asp Val Ile Ile Ser Gly Asn Lys Asn Leu Cys Tyr Ala Asn Thr
145                 150                 155                 160

Ile Asn Trp Lys Lys Leu Phe Gly Thr Ser Gly Gln Lys Thr Lys Ile
                165                 170                 175

Ile Ser Asn Arg Gly Glu Asn Ser Cys Lys Ala Thr Gly Gln Val Cys
                180                 185                 190

His Ala Leu Cys Ser Pro Glu Gly Cys Trp Gly Pro Glu Pro Arg Asp
            195                 200                 205

Cys Val Ser Cys Arg Asn Val Ser Arg Gly Arg Glu Cys Val Asp Lys
    210                 215                 220

Cys Asn Leu Leu Glu Gly Glu Pro Arg Glu Phe Val Glu Asn Ser Glu
225                 230                 235                 240

Cys Ile Gln Cys His Pro Glu Cys Leu Pro Gln Ala Met Asn Ile Thr
                245                 250                 255

Cys Thr Gly Arg Gly Pro Asp Asn Cys Ile Gln Cys Ala His Tyr Ile
                260                 265                 270

Asp Gly Pro His Cys Val Lys Thr Cys Pro Ala Gly Val Met Gly Glu
            275                 280                 285

Asn Asn Thr Leu Val Trp Lys Tyr Ala Asp Ala Gly His Val Cys His
    290                 295                 300

Leu Cys His Pro Asn Cys Thr Tyr Gly Cys Thr Gly Pro Gly Leu Glu
305                 310                 315                 320

Gly Cys Pro Thr Asn Gly Pro Lys Ile Pro Ser Ile Ala Thr Gly Met
```

```
                         325                 330                 335
Val Gly Ala Leu Leu Leu Leu Val Val Ala Leu Gly Ile Gly Leu
                340                 345                 350
Phe Met
```

```
<210> SEQ ID NO 42
<211> LENGTH: 323
<212> TYPE: PRT
<213> ORGANISM: Artificial Sequence
<220> FEATURE:
<223> OTHER INFORMATION: truncated CD19R

<400> SEQUENCE: 42

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
                20                  25                  30

Asn Ala Val Leu Gln Cys Leu Lys Gly Thr Ser Asp Gly Pro Thr Gln
            35                  40                  45

Gln Leu Thr Trp Ser Arg Glu Ser Pro Leu Lys Pro Phe Leu Lys Leu
        50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
290                 295                 300

Cys Ser Leu Val Gly Ile Leu His Leu Gln Arg Ala Leu Val Leu Arg
305                 310                 315                 320

Arg Lys Arg
```